United States Patent
Corcoran et al.

(10) Patent No.: US 7,118,902 B2
(45) Date of Patent: Oct. 10, 2006

(54) MODIFIED ADAMTS4 MOLECULES AND METHOD OF USE THEREOF

(75) Inventors: Christopher John Corcoran, Arlington, MA (US); Carl R. Flannery, Acton, MA (US); Weilan Zeng, Waltham, MA (US); Lisa A. Racie, Acton, MA (US); Thomas McDonagh, Acton, MA (US); Bethany A. Freeman, Arlington, MA (US); Katy E. Georgiadis, Belmont, MA (US); Edward R. LaVallie, Harvard, MA (US)

(73) Assignee: Wyeth, Madison, NJ (US)

( * ) Notice: Subject to any disclaimer, the term of this patent is extended or adjusted under 35 U.S.C. 154(b) by 375 days.

(21) Appl. No.: 10/628,432

(22) Filed: Jul. 29, 2003

(65) Prior Publication Data

US 2004/0142863 A1    Jul. 22, 2004

Related U.S. Application Data

(60) Provisional application No. 60/398,721, filed on Jul. 29, 2002.

(51) Int. Cl.
*C12N 15/57* (2006.01)
*C12N 9/64* (2006.01)
*C12N 15/01* (2006.01)
*C12N 15/79* (2006.01)

(52) U.S. Cl. .................. 435/226; 435/69.1; 435/252.3; 435/320.1; 435/440

(58) Field of Classification Search ..................... None
See application file for complete search history.

(56) References Cited

U.S. PATENT DOCUMENTS

| 4,419,446 | A | 12/1983 | Howley et al. |
|---|---|---|---|
| 4,522,811 | A | 6/1985 | Eppstein et al. |
| 4,554,101 | A | 11/1985 | Hopp |
| 4,816,567 | A | 3/1989 | Cabilly et al. |
| 6,451,575 | B1 * | 9/2002 | Arner et al. ................. 435/226 |
| 6,933,369 | B1 * | 8/2005 | Mueller et al. ......... 530/388.26 |
| 2002/0090373 | A1 | 7/2002 | Buckbinder et al. |
| 2002/0151702 | A1 * | 10/2002 | Racie et al. ............... 536/23.2 |
| 2003/0073116 | A1 | 4/2003 | Ginsburg et al. |
| 2003/0105313 | A1 * | 6/2003 | Racie et al. ............... 536/23.2 |
| 2004/0175817 | A1 * | 9/2004 | Jepson et al. ............... 435/226 |

FOREIGN PATENT DOCUMENTS

| EP | 0 123 289 | 10/1984 |
|---|---|---|
| EP | 123289 A2 | 10/1984 |
| EP | 0177343 A1 | 4/1985 |
| WO | WO 86/00639 | 1/1986 |
| WO | WO 86/00639 A1 | 1/1986 |
| WO | WO 00/53774 A3 | 9/2000 |

OTHER PUBLICATIONS

Eakin, A. E., et al., 1993, "Production of crystallizable cruzain, the major cysteine protease from Trypanosoma cruzi", The Journal of Biological Chemistry, vol. 268, No. 9, pp. 6115-6118.*

(Continued)

*Primary Examiner*—Naashat T. Nashed
*Assistant Examiner*—William W. Moore
(74) *Attorney, Agent, or Firm*—Kirkpatrick & Lockhart Nicholson Graham LLP

(57) ABSTRACT

The present invention relates to modified ADAMTS4 proteins having improved stability comparing to the corresponding native, unmodified proteins. The modified ADAMTS4 proteins can be expressed and isolated in large quantities, thus allowing further characterization of the proteins, such as crystallographic and enzyme kinetic studies. The purified, stable proteins would also facilitate the production of anti-ADAMTS antibodies and the development of inhibitors to ADAMTS enzymes.

14 Claims, 3 Drawing Sheets

OTHER PUBLICATIONS

Morgunova, E., et al., 1999, "Structure of human pro-matrix metalloproteinase-2: Activation mechanism revealed", *Science*, vol. 284, pp. 1667-1670.*

Souza, D., H., F., et al., 2001, "Crystallization and preliminary X-ray analysis of jararhagin, a metalloprotease/disintegrin from Bothrops jaracara snake venom", *Acta Crystallographica Section D*, vol. D57, pp. 1135-1137.*

Ahmed, K. M. et al., Association of an intronic polymorphism in the midkine (MK) gene with human sporadic colorectal cancer, *Cancer Lett.*, 180(2):159-163, 2002.

Ahmed, K. M. et al., Genetic variations of the midkine (MK) gene in human sporadic colorectal and gastric cancers, *Int. J. Mol. Med.*, 6(3):281-287, 2000.

Aridome, K. et al., Truncated midkine as a marker of diagnosis and detection of nodal metastases in gastrointestinal carcinomas, *Br. J. Cancer*, 78(4):472-477, 1998.

Brandt, K.D. and Mankin, H.J., Pathogenesis of Osteoarthritis, in "Textbook of Rheumatology," Kelly, W.N., Harris, E.D., Ruddy, S., and Sledge, C.B. (eds), W.B. Saunders Company, Philadelphia, PA, pp. 1355-1373, 1993.

Clarkson, T. et al., Making antibody fragments using phage display libraries, *Nature*, 352:624-628, 1991.

Flannery, C.R. et al., Identification of a stromelysin cleavage site within the interglobular domain of human aggrecan. Evidence for proteolysis at this site in vivo in human articular cartilage, *J. Biol. Chem.*, 267(2):1008-1014, 1992.

Fosang, A.J. et al., Neutrophil collagenase (MMP-8) cleaves at the aggrecanase site E373-A374 in the interglobular domain of cartilage aggrecan, *Biochem. J.*, 304 (Pt 2):347-351, 1994.

Gething, M.J. and Sambrook, J., Cell-surface expression of influenza haemagglutinin from a cloned DNA copy of the RNA gene, *Nature*, 293(5834):620-625, 1981.

Harlow, E. and Lane, D., Antibodies: A Laboratory Manual, Cold Spring Harbor Laboratory Press, Cold Spring Harbor, New York (1988).

Harris, W.J., Production of humanized monoclonal antibodies for *in vivo* imaging and therapy, *Biochem. Soc. Trans.*, 23(4):1035-1038, 1995.

Ikematsu, S. et al., Serum midkine levels are increased in patients with various types of carcinomas, *Br. J. Cancer*, 83(6):701-706, 2000.

Kaname, T. et al., The expression of truncated MK in human tumors, *Biochem. Biophys. Res. Commun.*, 219(1):256-260, 1996.

Kadomatsu, K., Recent progress of midkine research on cancer, *Nippon Rinsho*, 58(6):1337-1347, 2000.

Kohler, G. and Milstein, C., Continuous cultures of fused cells secreting antibody of predefined specificity, *Nature*, 256(5517):495-497, 1975.

Laemmli, U.K., Cleavage of structural proteins during the assembly of the head of bacteriophage T4, *Nature*, 227(5259):680-685, 1970.

Lewis, A.P. and Crowe, J.S., Generation of humanized monoclonal antibodies by 'best fit' framework selection and recombinant polymerase chain reaction, *Year Immunol.*, 7:110-118, 1993.

Li, X. et al., Differential protein profile in the ear-punched tissue of regeneration and non-regeneration strains of mice: a novel approach to explore the candidate genes for soft-tissue regeneration, *Biochim. Biophys. Acta*, 1524(2-3):102-9, 2000.

Li, X. et al., Analysis of gene expression in the wound repair/regeneration process, *Mamm. Genome*, 12(1):52-59, 2001.

Lohmander, L.S. et al., The structure of aggrecan fragments in human synovial fluid. Evidence that aggrecanase mediates cartilage degradation in inflammatory joint disease, joint injury, and osteoarthritis, *Arthritis Rheum.*, 36(9):1214-1222, 1993.

Maclean, C.H. et al., Costs attributable to osteoarthritis, *J. Rheumatol.*, 25(11):2213-2218, 1998.

Maniatis, T. et al., Molecular Cloning (A Laboratory Manual), Cold Spring Harbor Laboratory Press, Cold Spring Harbor, NY, pp. 387-389, 1982.

Marks, J.D., By-passing immunization. Human antibodies from V-gene libraries displayed on phage, *J. Mol. Biol.*, 222(3):581-597, 1991.

Miyashiro, I. et al., Expression of truncated midkine in human colorectal cancers, *Cancer Lett.* 106(2):287-291, 1996.

Morrison, S. L. and Schlom, J., Recombinant chimeric monoclonal antibodies, in S. A. Rosenberg (ed.), *Important Advances in Oncology 3*, Lippincott, Philadelphia, PA, 1990.

Oakley, B. R. et al., A simplified ultrasensitive silver stain for detecting proteins in polyacrylamide gels, *Anal. Biochem.*, 105(2):361-363, 1980.

Paul, S. et al., Detection of truncated midkine in Wilms' tumor by a monoclonal antibody against human recombinant truncated midkine, *Cancer Lett.*, 163(2):245-251, 2001.

Paul, S. et al., Molecular cloning, expression and purification of truncated midkine and its growth stimulatory activity on Wilms' tumor (G401) cells, *Cancer Lett.*, 163(2):239-244, 2001.

Presta, L., Humanized Monoclonal Antibodies, in *Annual Reports in Medicinal Chemistry*, Academic Press, 1994.

Roberts, S. et al., Matrix turnover in human cartilage repair tissue in autologous chondrocyte implantation, *Arthritis Rheum.*, 44(11):2586-2598, 2001.

Sandy, J.D. et al., Analysis of the catabolism of aggrecan in cartilage explants by quantitation of peptides from the three globular domains, *J. Biol. Chem.*, 266(13):8198-8205, 1991.

Sandy, J.D. et al., The structure of aggrecan fragments in human synovial fluid. Evidence for the involvement in osteoarthritis of a novel proteinase which cleaves the Glu 373-Ala 374 bond of the interglobular domain. *J. Clin. Invest.*, 89(5):1512-1516, 1992.

Towbin, H. et al., Electrophoretic transfer of proteins from polyacrylamide gels to nitrocellulose sheets: procedure and some applications, Proc. Natl. Acad. Sci. U S A., 76(9):4350-4354, 1979.

Winter, G. and Milstein, C., Man-made antibodies, *Nature*, 349(6307):293-299, 1991.

International Search Report mailed Mar. 2, 2004, corresponding with International Application PCT/US2003/23483, 4 pages.

NCBI Annotation Project, XP_123829.midkine [Mus musc . . . [gi:20839708], National Center for Biotechnology Information, 8600 Rockville Pike, Bethesda, MD 20894, http://www.ncbi.nlm.nih.gov/entrez/viewer.fcgi?db=protein&val=20839708, May 16, 2002.

Uehara, K. et al., BAA01457.midkine [*Homo sapiens* . . . [gi:219929], National Center for Biotechnology Information, 8600 Rockville Pike, Bethesda, MD 20894, http://www.ncbi.nlm.nih.gov/entrez/viewer.fcgi?db=protein&val=219929, PRI May 29, 1992.

JAX Mice MRL/MpJ Product Specification, Stock No. 000486, The Jackson Laboratory, Bar Harbor, ME, pp. 1-5, Mar. 19, 2002.

JAX Mice B6.MRL-Tnfrsf6$^{lpr}$ Product Specification, Stock No. 000482, The Jackson Laboratory, Bar Harbor, ME, pp. 1-4, Mar. 19, 2002.

Zhang, N. and Deuel, T.F., Pleiotrophin and midkine, a family of mitogenic and angiogenic heparin-binding growth and differentiation factors, *Curr. Opin. Hematol.* 6(1):44-50, 1999.

Haynes, H. and Rumsby, M., The pleiotropin/midkine family of cytokines: role in glial-neuronal signaling, *Prog. Brain Res.*, 132:313-324, 2001.

Muramatsu, T., Midkine (MK), the product of a retinoic acid responsive gene, and pleiotrophin constitute a new protein family regulating growth and differentiation, *Int. J. Dev. Biol.*, 37(1):183-188, 1993.

Ol, et al., "*Immunoglobulin-Producing Hybrid Cell Lines*", Selected Methods in Cellular Immunology, 1980, pp. 351-372.

Cal et al., "Cloning, expression analysis, and structural characterization of seven novel human ADAMTSs, a family of metalloproteinases with disintegrain and thrombospondin-1 domains", Gene 283 (2002), pp. 49-62.

Somerville et al., "Characterization of ADAMTS-9 and ADAMTS-20 as a Distinct ADAMTS Subfamily Related to *Caenorhabditis elegans* GON-1*", J. Biol. Chem. Mar. 14, 2003, vol. 278, No. 11, pp. 9503-9513.

Kuno et al., "ADAMTS-1 Protein Anchors at the Extracellular Matrix through the Thrombospondin Type I Motifs and Its Spacing Region*", J. Biol. Chem., vol. 273, No. 22, May 29, 1998, pp. 13912-13917.

Tortorella et al., "Sites of Aggrecan Cleavage by Recombinant Human Aggrecanase-1 (ADAMTS-4)*", J. Biol. Chem., vol. 275, No. 24, Jun. 16, 2000, pp. 18566-18573.

Tortorella et al., "Purification and Cloning of Aggrecanase-1: A Member of the ADAMTS Family of Proteins", SCIENCE, vol. 284, Jun. 4, 1999, pp. 1664-1666.

Abbaszade et al., "Cloning and Characterization of ADAMTS11, an Aggrecanase from the ADAMTS Family*", J. Biol. Chem., vol. 274, No. 3, Aug. 13, 1999, pp. 23443-23450.

Matthews et al., "Brain-enriched Hyaluronan Binding (BEHAB)/Brevican Cleavage in a Glioma Cell Line Is Mediated by a Disintegrin and Metalloproteinase with Thrombospondin Motifs (ADAMTS) Family Member*", J. Biol. Chem., vol. 275, No. 30, Jul. 28, 2000, pp. 22695-22703.

Delagrave et al., "Recursive ensemble mutagenesis", Protein Engineering, vol. 6, No. 3, 1993, pp. 327-331.

Hughes et al., "Monoclonal antibodies that specifically recognize neoepitope sequences generated by 'aggrecanase' and matrix metalloproteinase cleavage of aggrecan: application to catabolism *in situ* and *in vitro*", Biochem J., 1995, pp. 799-804.

Mercuri et al., "Recombinant Human Aggrecan G1-G2 Exhibits Native Binding Properties and Substrate Specificity for Matrix Metalloproteinases and Aggrecanase*", J. Biol. Chem., vol. 274, No. 45, Nov. 5, 1999, pp. 32387-32395.

Miller et al., "An Insect Baculovirus Host-Vector System For High-Level Expression of Foreign Genes", Genetic Engineering, vol. 8, (Plenum Press 1986), pp. 277-287.

Caterson et al., "Mechanisms involved in cartilage proteoglycan catabolism", Matrix Biology, vol. 19, (2000), pp. 333-344.

Kashiwagi et al., TIMP-3 Is a Potent Inhibitor of Aggrecanase 1 (ADAM-TS4) and Aggrecanase 2 (ADAM-TS5)*, J. Biol. Chem., vol. 276, No. 16, Apr. 20, 2001, pp. 12501-12504.

Hashimoto et al., Inhibition of ADAMTS4 (aggrecanase-1) by tissue inhibitors of metalloproteinases (TIMP-1, 2, 3 and 4), FEBS Letters 494, (2001), pp. 192-195.

Little et al., "Cyclosporin A Inhibition of Aggrecanase-Mediated Proteoglycan Catabolism in Articular Cartilage", Arthritis & Rheumatism, vol. 46, No. 1, Jan. 2002, pp. 124-129.

Rodriguez-Manzaneque et al., "ADAMTS1 cleaves aggrecan at multiple sites and is differentially inhibited by metalloproteinase inhibitors", Biochemical and Biophysical Research Communications 293 (2002), pp. 501-508.

Peppard et al., Development of a High-Throughput Screening Assay for Inhibitors of Aggrecan Cleavage Using Luminescent Oxygen Channeling (AlphaScreen™), Society for Biomolecular Screening, (2003) pp. 149-156.

Gossen et al., "Tight control of gene expression in mammalian cells by tetracycline-responsive promoters", Proc. Natl. Acad. Sci. USA, vol. 89, Jun. 1992, pp. 5547-5551.

Urlaub et al., "Isolation of Chinese hamster cell mutants deficient in dihydrofolate reductase activity", Proc. Ntl. Acad. Sci. USA, vol. 77, No. 7, Jul. 1980, pp. 4216-4220.

Gill et al., "Calculation of Protein Extinction Coefficients from Amino Acid Sequence Data", Analytical Biochemistry 182, (1989) pp. 319-326.

Flannery et al., "Autocatalytic Cleavage of ADAMTS-4 (Aggrecanase-1) Reveals Multiple Blycosaminoglycan-binding Sites*", J. Biol. Chem., vol. 277, No. 45, Nov. 8, 2002, pp. 42775-42780.

Okayama et al., "High-Efficiency Cloning of Full-Length cDNA", Molecular and Cellular Biology, vol. 2, No. 2, Feb. 1982, pp. 161-170.

Gough et al., "Structure and expression of the mRNA for murine granulocyte-macrophage colony stimulating factor", EMBO Journal, vol. 4, No. 3, 1985, pp. 645-653.

Wong et al., "Human GM-CSF: Molecular Cloning of the Complementary DNA and Purification of the Natural and Recombinant Proteins", SCIENCE, vol. 228, May 17, 1985, pp. 810-815.

Kaufman, "Identification of the components necessary for adenovirus translational control and their utilization in cDNA expression vectors", Proc. Nat. Acad. Sci. USA, vol. 82, Feb. 1985, pp. 689-693.

Morinaga et al., "Improvement of Oligonucleotide-Directed Site-Specific Mutagenesis Using Double-Stranded Plasmid DNA", BIO/TECHNOLOGY, Jul. 1984, pp. 636-639.

Jang et al., "Initiation of Protein Synthesis by Internal Entry of Ribosomes into the 5' Nontranslated Region of Encephalomyocarditis Virus RNA In Vivo", J. Virology, vol. 63, No. 4, Apr. 1989, pp. 1651-1660.

Taniguchi et al., "Expression of the human fibroblast interferon gene in *Escherichia coli*\*", Proc. Natl. Acad. Sci. USA, vol. 77, No. 9, Sep. 1980, pp. 5230-5233.

Kaufman et al., "Amplification and Expression of Sequences Cotransfected with a Modular Dihydrofolate Reductase Complementary DNA Gene", J. Mol. Biol. (1982) 159, pp. 601-621.

Kaufman et al., "Construction of a Modular Dihydrofolate Reductase cDNA Gene: Analysis of Signals Utilized for Efficient Expression", Molecular and Cellular Biology, vol. 2, No. 11, Nov. 1982, pp. 1304-1319.

Littlefield et al., "Selection of Hybrids from Matings of Fibroblasts in vitro and Their Presumed Recombinants", Aug. 14, 1964, vol. 145, pp. 709.

\* cited by examiner

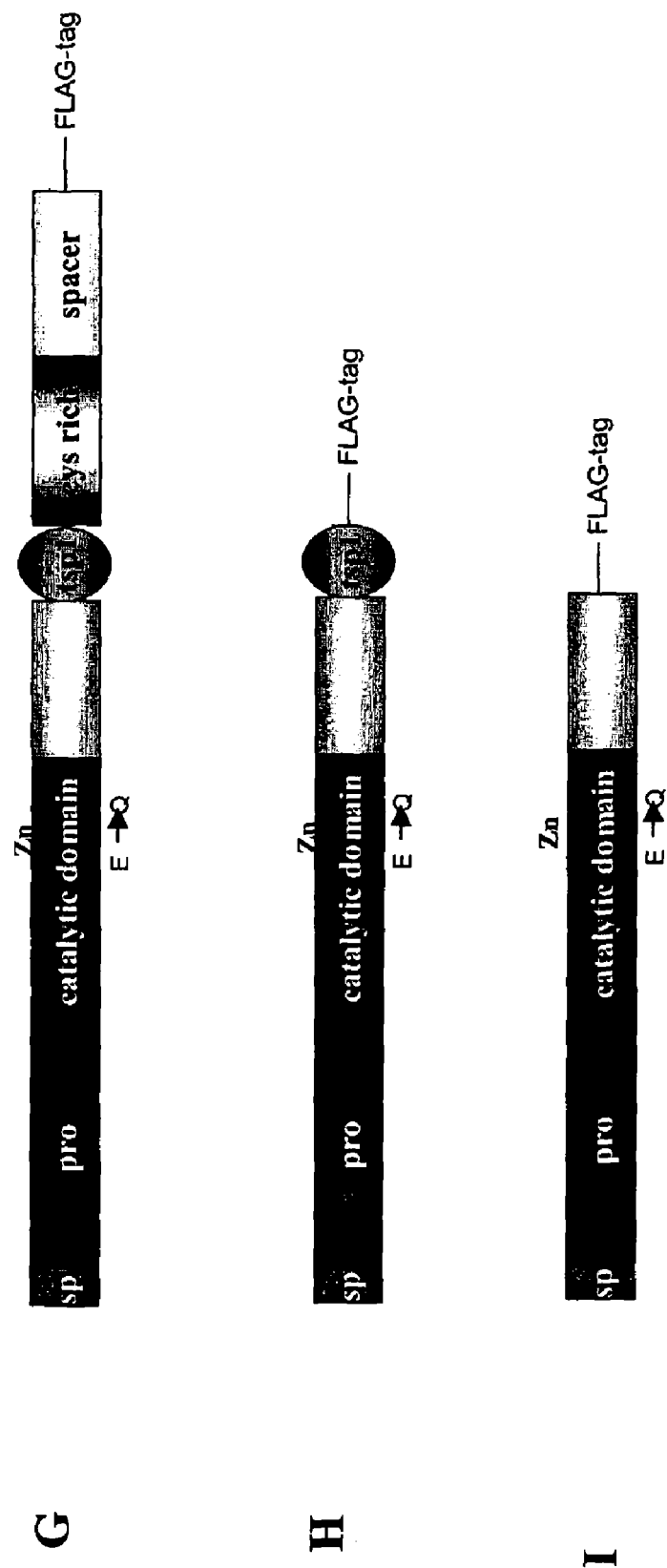
CONT. FIG. 2 und S 7,118,902 B2

SEQUENCE LISTING

<160> NUMBER OF SEQ ID NOS: 53

<210> SEQ ID NO 1
<211> LENGTH: 837
<212> TYPE: PRT
<213> ORGANISM: Homo sapiens

<400> SEQUENCE: 1

```
Met Ser Gln Thr Gly Ser His Pro Gly Arg Gly Leu Ala Gly Arg Trp
1               5                   10                  15

Leu Trp Gly Ala Gln Pro Cys Leu Leu Pro Ile Val Pro Leu Ser
            20                  25                  30

Trp Leu Val Trp Leu Leu Leu Leu Leu Ala Ser Leu Leu Pro Ser
            35                  40                  45

Ala Arg Leu Ala Ser Pro Leu Pro Arg Glu Glu Ile Val Phe Pro
        50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
                100                 105                 110

Gly Gln Ala Pro Glu Leu Leu Gly Gly Ala Glu Pro Gly Thr Tyr Leu
            115                 120                 125

Thr Gly Thr Ile Asn Gly Asp Pro Glu Ser Val Ala Ser Leu His Trp
    130                 135                 140

Asp Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Arg Pro Arg
            195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
                260                 265                 270

Gly Ser Gly Glu Glu Gly Pro Gln Val Gly Pro Ser Ala Ala Gln Thr
            275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Gly
                340                 345                 350

Leu Gln Ser Ala Phe Thr Ala Ala His Glu Leu Gly His Val Phe Asn
```

-continued

```
                355                 360                 365
Met Leu His Asp Asn Ser Lys Pro Cys Ile Ser Leu Asn Gly Pro Leu
            370                 375                 380
Ser Thr Ser Arg His Val Met Ala Pro Val Met Ala His Val Asp Pro
385                 390                 395                 400
Glu Glu Pro Trp Ser Pro Cys Ser Ala Arg Phe Ile Thr Asp Phe Leu
                405                 410                 415
Asp Asn Gly Tyr Gly His Cys Leu Leu Asp Lys Pro Glu Ala Pro Leu
            420                 425                 430
His Leu Pro Val Thr Phe Pro Gly Lys Asp Tyr Asp Ala Asp Arg Gln
            435                 440                 445
Cys Gln Leu Thr Phe Gly Pro Asp Ser Arg His Cys Pro Gln Leu Pro
450                 455                 460
Pro Pro Cys Ala Ala Leu Trp Cys Ser Gly His Leu Asn Gly His Ala
465                 470                 475                 480
Met Cys Gln Thr Lys His Ser Pro Trp Ala Asp Gly Thr Pro Cys Gly
            485                 490                 495
Pro Ala Gln Ala Cys Met Gly Gly Arg Cys Leu His Met Asp Gln Leu
            500                 505                 510
Gln Asp Phe Asn Ile Pro Gln Ala Gly Gly Trp Gly Pro Trp Gly Pro
            515                 520                 525
Trp Gly Asp Cys Ser Arg Thr Cys Gly Gly Gly Val Gln Phe Ser Ser
            530                 535                 540
Arg Asp Cys Thr Arg Pro Val Pro Arg Asn Gly Gly Lys Tyr Cys Glu
545                 550                 555                 560
Gly Arg Arg Thr Arg Phe Arg Ser Cys Asn Thr Glu Asp Cys Pro Thr
                565                 570                 575
Gly Ser Ala Leu Thr Phe Arg Glu Glu Gln Cys Ala Ala Tyr Asn His
            580                 585                 590
Arg Thr Asp Leu Phe Lys Ser Phe Pro Gly Pro Met Asp Trp Val Pro
            595                 600                 605
Arg Tyr Thr Gly Val Ala Pro Gln Asp Gln Cys Lys Leu Thr Cys Gln
610                 615                 620
Ala Arg Ala Leu Gly Tyr Tyr Tyr Val Leu Glu Pro Arg Val Val Asp
625                 630                 635                 640
Gly Thr Pro Cys Ser Pro Asp Ser Ser Ser Val Cys Val Gln Gly Arg
                645                 650                 655
Cys Ile His Ala Gly Cys Asp Arg Ile Ile Gly Ser Lys Lys Lys Phe
            660                 665                 670
Asp Lys Cys Met Val Cys Gly Gly Asp Gly Ser Gly Cys Ser Lys Gln
            675                 680                 685
Ser Gly Ser Phe Arg Lys Phe Arg Tyr Gly Tyr Asn Asn Val Val Thr
            690                 695                 700
Ile Pro Ala Gly Ala Thr His Ile Leu Val Arg Gln Gln Gly Asn Pro
705                 710                 715                 720
Gly His Arg Ser Ile Tyr Leu Ala Leu Lys Leu Pro Asp Gly Ser Tyr
                725                 730                 735
Ala Leu Asn Gly Glu Tyr Thr Leu Met Pro Ser Pro Thr Asp Val Val
            740                 745                 750
Leu Pro Gly Ala Val Ser Leu Arg Tyr Ser Gly Ala Thr Ala Ala Ser
            755                 760                 765
Glu Thr Leu Ser Gly His Gly Pro Leu Ala Gln Pro Leu Thr Leu Gln
            770                 775                 780
```

-continued

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Arg Pro
            820                 825                 830

Trp Ala Gly Arg Lys
        835

<210> SEQ ID NO 2
<211> LENGTH: 1294
<212> TYPE: DNA
<213> ORGANISM: Artificial
<220> FEATURE:
<223> OTHER INFORMATION: This is an artificial DNA sequence cloned by
      PCR amplification
<220> FEATURE:
<221> NAME/KEY: misc_feature
<222> LOCATION: (1)..(1294)
<223> OTHER INFORMATION: artificial DNA sequence

<400> SEQUENCE: 2
ccatgtccca gacaggctcg catcccggga ggggcttggc agggcgctgg ctgtggggag      60
cccaaccctg cctcctgctc cccattgtgc cgctctcctg gctggtgtgg ctgcttctgc     120
tactgctggc ctctctcctg ccctcagccc ggctggccag ccccctcccc cgggaggagg     180
agatcgtgtt tccagagaag ctcaacggca gcgtcctgcc tggctcgggc gcccctgcca     240
ggctgttgtg ccgcttgcag gcctttgggg agacgctgct actagagctg gagcaggact     300
ccggtgtgca ggtcgagggg ctgacagtgc agtacctggg ccaggcgcct gagctgctgg     360
gtggagcaga gcctggcacc tacctgactg gcaccatcaa tggagatccg gagtcggtgg     420
catctctgca ctgggatggg ggagccctgt taggcgtgtt acaatatcgg ggggctgaac     480
tccacctcca gccctggag ggaggcaccc ctaactctgc tgggggacct ggggctcaca     540
tcctacgccg gaagagtcct gccagcggtc aaggtcccat gtgcaacgtc aaggctcctc     600
ttggaagccc cagccccaga ccccgaagag ccaagcgctt tgcttcactg agtagatttg     660
tggagacact ggtggtggca gatgacaaga tggccgcatt ccacggtgcg gggctaaagc     720
gctacctgct aacagtgatg gcagcagcag ccaaggcctt caagcaccca agcatccgca     780
atcctgtcag cttggtggtg actcggctag tgatcctggg gtcaggcgag gaggggcccc     840
aagtggggcc cagtgctgcc cagaccctgc gcagcttctg tgcctggcag cggggcctca     900
acacccctga ggactcggac cctgaccact tgacacagc cattctgttt acccgtcagg     960
acctgtgtgg agtctccact tgcgacacgc tgggtatggc tgatgtgggc accgtctgtg    1020
acccggaaat gggcgaattc ccactcggag ctgtgccatt gtggaggatg atgggctcca    1080
gtcagccttc actgctgctc atgaactggg tcatgtcttc aacatgctcc atgacaactc    1140
caagccatgc atcagtttga atgggccttt gagcacctct cgccatgtca tggcccctgt    1200
gatggctcat gtggatcctg aggagccctg gtccccctgc agtgcccgct tcatcactga    1260
cttcctggac aatggctatg gcactgtctc ctta                                1294

<210> SEQ ID NO 3
<211> LENGTH: 1421
<212> TYPE: DNA
<213> ORGANISM: Artificial
<220> FEATURE:
<223> OTHER INFORMATION: This is an artificial DNA sequence cloned by

PCR

<400> SEQUENCE: 3

```
ctccaagcca tgcatcagtt tgaatgggcc tttgagcacc tctcgccatg tcatggcccc      60
tgtgatggct catgtggatc ctgaggagcc ctggtccccc tgcagtgccc gcttcatcac     120
tgacttcctg acaatggct atgggcactg tctcttagac aaaccagagg ctccattgca     180
tctgcctgtg actttccctg caaggacta tgatgctgac cgccagtgcc agctgacctt     240
cgggcccgac tcacgccatt gtccacagct gccgccgccc tgtgctgccc tctggtgctc     300
tggccacctc aatggccatg ccatgtgcca gaccaaacac tcgccctggg ccgatggcac     360
accctgcggg cccgcacagg cctgcatggg tggtcgctgc ctccacatgg accagctcca     420
ggacttcaat attccacagg ctggtggctg ggtccttgg ggaccatggg gtgactgctc     480
tcggacctgt gggggtggtg tccagttctc ctcccgagac tgcacgaggc ctgtcccccg     540
gaatggtggc aagtactgtg agggccgccg tacccgcttc cgctcctgca cactgaggagaga     600
ctgcccaact ggctcagccc tgaccttccg cgaggagcag tgtgctgcct acaaccaccg     660
caccgaccte ttcaagagct cccaggggcc catggactgg ttcctcgct acacaggcgt     720
ggcccccag gaccagtgca aactcacctg ccaggcccgg gcactgggct actactatgt     780
gctggagcca cgggtggtag atgggacccc ctgttcccccg acagctcct cggtctgtgt     840
ccagggccga tgcatccatg ctggctgtga tcgcatcatt ggctccaaga gaagtttga     900
caagtgcatg gtgtgcggag gggacggttc tggttgcagc aagcagtcag gctccttcag     960
gaaattcagg tacggataca caatgtggt cactatcccc gcggggccca cccacattct    1020
tgtccggcag cagggaaacc ctggccaccg gagcatctac ttggccctga gctgccaga    1080
tggctcctat gccctcaatg gtgaatacac gctgatgccc tcccccacag atgtggtact    1140
gcctggggca gtcagcttgc gctacagcgg ggccactgca gcctcagaga cactgtcagg    1200
ccatgggcca ctggcccagc ctttgacact gcaagtccta gtggctggca accccaggag    1260
cacacgcctc cgatacagct tcttcgtgcc ccggccgacc ccttcaacgc cacgccccac    1320
tccccaggac tggctgcacc gaagagcaca gattctggag atccttcggc ggcgcccctg    1380
ggcgggcagg aaataaccte actatgcggc cgcagtcagt c                       1421
```

<210> SEQ ID NO 4
<211> LENGTH: 4307
<212> TYPE: DNA
<213> ORGANISM: Homo sapiens

<400> SEQUENCE: 4

```
cacagacaca tatgcacgag agagacagag gaggaaagag acagagacaa aggcacagcg      60
gaagaaggca gagacagggc aggcacagaa gcggcccaga cagagtccta cagagggaga     120
ggccagagaa gctgcagaag acacaggcag ggagagacaa agatccagga aaggagggct     180
caggaggaga gtttggagaa gccagacccc tgggcacctc tcccaagccc aaggactaag     240
ttttctccat ttcctttaac ggtcctcagc ccttctgaaa actttgcctc tgaccttggc     300
aggagtccaa gccccaggc tacagagagg agctttccaa agctagggtg tggaggactt     360
ggtgccctag acgcctcag tccctcccag ctgcagtacc agtgccatgt cccagacagg     420
ctcgcatccc gggagggct tggcagggcg ctggctgtgg ggagcccaac cctgcctcct     480
gctcccccatt gtgccgctct cctggctggt gtggctgctt ctgctactgc tggcctctct     540
cctgccctca gcccggctgg ccagcccct ccccgggag gaggagatcg tgtttccaga     600
```

-continued

```
gaagctcaac ggcagcgtcc tgcctggctc gggcacccct gccaggctgt tgtgccgctt      660
gcaggccttt ggggagacgc tgctactaga gctggagcag gactccggtg tgcaggtcga      720
ggggctgaca gtgcagtacc tgggccaggc gcctgagctg ctgggtggag cagagcctgg      780
cacctacctg actggcacca tcaatggaga tccggagtcg gtggcatctc tgcactggga      840
tgggggagcc ctgttaggcg tgttacaata tcgggggct gaactccacc tccagccct       900 ggagggaggc accctaact ctgctggggg acctgggct cacatcctac gccggaagag       960
tcctgccagc ggtcaaggtc ccatgtgcaa cgtcaaggct cctcttggaa gccccagccc      1020
cagaccccga gagccaagc gctttgcttc actgagtaga tttgtggaga cactggtggt      1080
ggcagatgac aagatggccg cattccacgg tgcggggcta aagcgctacc tgctaacagt      1140
gatggcagca gcagccaagg ccttcaagca cccaagcatc cgcaatcctg tcagcttggt      1200
ggtgactcgg ctagtgatcc tggggtcagg cgaggagggg ccccaagtgg ggcccagtgc      1260
tgcccagacc ctgcgcagct tctgtgcctg gcagcgggc ctcaacaccc ctgaggactc       1320
ggaccctgac cactttgaca cagccattct gtttacccgt caggacctgt gtggagtctc      1380
cacttgcgac acgctgggta tggctgatgt gggcaccgtc tgtgacccgg ctcggagctg      1440
tgccattgtg gaggatgatg ggctccagtc agccttcact gctgctcatg aactgggtca      1500
tgtcttcaac atgctccatg acaactccaa gccatgcatc agtttgaatg ggcctttgag      1560
cacctctcgc catgtcatgg cccctgtgat ggctcatgtg gatcctgagg agccctggtc      1620
cccctgcagt gcccgcttca tcactgactt cctggacaat ggctatgggc actgtctctt      1680
agacaaacca gaggctccat tgcatctgcc tgtgactttc cctggcaagg actatgatgc      1740
tgaccgccag tgccagctga ccttcgggcc cgactcacgc cattgtccac agctgccgcc      1800
gccctgtgct gccctctggt gctctggcca cctcaatggc catgccatgt gccagaccaa      1860
acactcgccc tgggccgatg gcacaccctg cgggcccgca caggcctgca tgggtggtcg      1920
ctgcctccac atggaccagc tccaggactt caatattcca caggctggtg gctggggtcc      1980
ttggggacca tggggtgact gctctcggac ctgtgggggt ggtgtccagt tctcctcccg      2040
agactgcacg aggcctgtcc cccggaatgg tgcaagtac tgtgagggcc gccgtacccg       2100
cttccgctcc tgcaacactg aggactgcca aactggctca gccctgacct tccgcgagga      2160
gcagtgtgct gcctacaacc accgcaccga cctcttcaag agcttcccag ggcccatgga      2220
ctgggttcct cgctacacag gcgtggcccc ccaggaccag tgcaaactca cctgccaggc      2280
ccgggcactg ggctactact atgtgctgga gccacgggtg gtagatggga ccccctgttc      2340
cccggacagc tcctcggtct gtgtccaggg ccgatgcatc catgctggct gtgatcgcat      2400
cattggctcc aagaagaagt tgacaagtg catggtgtgc ggaggggacg gttctggttg       2460
cagcaagcag tcaggctcct tcaggaaatt caggtacgga tacaacaatg tggtcactat      2520
ccccgcgggg gccacccaca ttcttgtccg gcagcaggga aaccctggcc accggagcat      2580
ctacttggcc ctgaagctgc cagatggctc ctatgccctc aatggtgaat acacgctgat      2640
gccctccccc acagatgtgg tactgcctgg ggcagtcagc ttgcgctaca gcggggccac      2700
tgcagcctca gagacactgt caggccatgg ccactggcc cagcctttga cactgcaagt       2760
cctagtggct ggcaacccc aggacacacg cctccgatac agcttcttcg tgccccggcc       2820
gaccccttca acgccacgcc ccactcccca ggactggctg caccgaagag cacagattct      2880
ggagatcctt cggcggcgcc cctgggcggg caggaaataa cctcactatc ccggctgccc      2940
```

```
tttctgggca ccggggcctc ggacttagct gggagaaaga gagagcttct gttgctgcct    3000
catgctaaga ctcagtgggg aggggctgtg ggcgtgagac ctgcccctcc tctctgccct    3060
aatgcgcagg ctggccctgc cctggtttcc tgccctggga ggcagtgatg ggttagtgga    3120 tggaagggc tgacagacag ccctccatct aaactgcccc ctctgccctg cgggtcacag    3180
gagggagggg gaaggcaggg agggcctggg ccccagttgt atttatttag tatttattca    3240
cttttattta gcaccaggga aggggacaag gactagggtc ctggggaacc tgaccctga    3300 cccctcatag ccctcaccct ggggctagga atccagggt ggtggtgata ggtataagtg    3360
gtgtgtgtat gcgtgtgtgt gtgtgtgtga aaatgtgtgt gtgcttatgt atgaggtaca    3420
acctgttctg ctttcctctt cctgaatttt attttttggg aaaagaaaag tcaagggtag    3480
ggtgggcctt cagggagtga gggattatct tttttttttt ttctttcttt ctttcttttt    3540 ttttttgag acagaatctc gctctgtcgc ccaggctgga gtgcaatggc acaatctcgg    3600
ctcactgcat cctccgcctc ccgggttcaa gtgattctca tgcctcagcc tcctgagtag    3660
ctgggattac aggctcctgc caccacgccc agctaatttt tgttttgttt tgtttggaga    3720
cagagtctcg ctattgtcac cagggctgga atgatttcag ctcactgcaa ccttcgccac    3780
ctgggttcca gcaattctcc tgcctcagcc tcccgagtag ctgagattat aggcacctac    3840
caccacgccc ggctaatttt tgtattttta gtagagacgg ggtttcacca tgttggccag    3900
gctggtctcg aactcctgac cttaggtgat ccactcgcct tcatctccca aagtgctggg    3960
attacaggcg tgagccaccg tgcctggcca cgcccaacta ttttttgtat ttttagtaga    4020
gacagggttt caccatgttg gccaggctgc tcttgaactc ctgacctcag gtaatcgacc    4080
tgcctcggcc tcccaaagtg ctgggattac aggtgtgagc caccacgccc ggtacatatt    4140
ttttaaattg aattctacta tttatgtgat cctttggag tcagacagat gtggttgcat    4200
cctaactcca tgtctctgag cattagattt ctcatttgcc aataataata cctcccttag    4260
aagtttgttg tgaggattaa ataatgtaaa taaagaacta gcataac                 4307

<210> SEQ ID NO 5
<211> LENGTH: 42
<212> TYPE: DNA
<213> ORGANISM: Artificial
<220> FEATURE:
<223> OTHER INFORMATION: PCR primer

<400> SEQUENCE: 5
aaatgggcga attcccacca tgtcccagac aggctcgcat cc                       42

<210> SEQ ID NO 6
<211> LENGTH: 8
<212> TYPE: DNA
<213> ORGANISM: artificial
<220> FEATURE:
<223> OTHER INFORMATION: 8-bp tail sequence

<400> SEQUENCE: 6 aaatgggc                                                              8

<210> SEQ ID NO 7
<211> LENGTH: 6
<212> TYPE: DNA
<213> ORGANISM: Artificial
<220> FEATURE:
<223> OTHER INFORMATION: EcoRI site

<400> SEQUENCE: 7
```

```
gaattc                                                                    6

<210> SEQ ID NO 8
<211> LENGTH: 5
<212> TYPE: DNA
<213> ORGANISM: Artificial
<220> FEATURE:
<223> OTHER INFORMATION: Kozak sequence

<400> SEQUENCE: 8 ccacc                                                                     5

<210> SEQ ID NO 9
<211> LENGTH: 26
<212> TYPE: DNA
<213> ORGANISM: Artificial
<220> FEATURE:
<223> OTHER INFORMATION: PCR primer

<400> SEQUENCE: 9
taagagacag tgcccatagc cattgt                                             26

<210> SEQ ID NO 10
<211> LENGTH: 26
<212> TYPE: DNA
<213> ORGANISM: Artificial
<220> FEATURE:
<223> OTHER INFORMATION: PCR primer

<400> SEQUENCE: 10
ctccaagcca tgcatcagtt tgaatg                                             26

<210> SEQ ID NO 11
<211> LENGTH: 41
<212> TYPE: DNA
<213> ORGANISM: Artificial
<220> FEATURE:
<223> OTHER INFORMATION: PCR fragment

<400> SEQUENCE: 11
gactgactgc ggccgcatag tgaggttatt tcctgcccgc c                            41

<210> SEQ ID NO 12
<211> LENGTH: 8
<212> TYPE: DNA
<213> ORGANISM: Artificial
<220> FEATURE:
<223> OTHER INFORMATION: 8-bp tail sequence

<400> SEQUENCE: 12 gactgact                                                                  8

<210> SEQ ID NO 13
<211> LENGTH: 8
<212> TYPE: DNA
<213> ORGANISM: Artificial
<220> FEATURE:
<223> OTHER INFORMATION: NotI site

<400> SEQUENCE: 13 gcggccgc                                                                  8

<210> SEQ ID NO 14
<211> LENGTH: 2542
<212> TYPE: DNA
```

<213> ORGANISM: Artificial
<220> FEATURE:
<223> OTHER INFORMATION: PCR cloned ADAMTS4 cDNA

<400> SEQUENCE: 14

| | | | | | |
|---|---|---|---|---|---|
| gaattcccac | catgtcccag | acaggctcgc | atcccgggag | ggcttggca | gggcgctggc | 60 |
| tgtggggagc | tcaaccctgc | ctcctgctcc | ccattgtgcc | gctctcctgg | ctggtgtggc | 120 |
| tgcttctgct | actgctggcc | tctctcctgc | cctcagcccg | gctggccagc | cccctcccc | 180 |
| gggaggagga | gatcgtgttt | ccagagaagc | tcaacggcag | cgtcctgcct | ggctcgggcg | 240 |
| cccctgccag | gctgttgtgc | cgcttgcagg | cctttgggga | gacgctgcta | ctagagctgg | 300 |
| agcaggactc | cggtgtgcag | gtcgaggggc | tgacagtgca | gtacctgggc | caggcgcctg | 360 |
| agctgctggg | tggagcagag | cctggcacct | acctgactgg | caccatcaat | ggagatccgg | 420 |
| agtcggtggc | atctctgcac | tgggatgggg | agccctgtt | aggcgtgtta | caatatcggg | 480 |
| gggctgaact | ccacctccag | ccctggagg | gaggcacccc | taactctgct | ggggacctg | 540 |
| ggctcacat | cctacgccgg | aagagtcctg | ccagcggtca | aggtcccatg | tgcaacgtca | 600 |
| aggctcctct | tggaagcccc | agccccagac | ccgaagagc | caagcgcttt | gcttcactga | 660 |
| gtagatttgt | ggagacactg | tggtggcag | atgacaagat | ggccgcattc | cacggtgcgg | 720 |
| ggctaaagcg | ctacctgcta | acagtgatgg | cagcagcagc | caaggccttc | aagcacccaa | 780 |
| gcatccgcaa | tcctgtcagc | ttggtggtga | ctcggctagt | gatcctgggg | tcaggcgagg | 840 |
| aggggcccca | gtggggccc | agtgctgccc | agaccctgcg | cagcttctgt | gcctggcagc | 900 |
| ggggcctcaa | caccctgag | gactcggacc | ctgaccactt | tgacacagcc | attctgttta | 960 |
| cccgtcagga | cctgtgtgga | gtctccactt | gcgacacgct | gggtatggct | gatgtgggca | 1020 |
| ccgtctgtga | cccggctcgg | agctgtgcca | ttgtggagga | tgatgggctc | cagtcagcct | 1080 |
| tcagtgctgc | tcatcaactg | ggtcatgtct | caacatgct | ccatgacaac | tccaagccat | 1140 |
| gcatcagttt | gaatgggcct | tgagcacct | ctcgccatgt | catggcccct | gtgatggctc | 1200 |
| atgtggatcc | tgaggagccc | tggtcccct | gcagtgcccg | cttcatcact | gacttcctgg | 1260 |
| acaatggcta | tgggcactgt | ctcttagaca | accagaggc | tccattgcat | ctgcctgtga | 1320 |
| cttcccctgg | caaggactat | gatgctgacc | gccagtgcca | gctgaccttc | gggcccgact | 1380 |
| cacgccattg | tccacagctg | ccgccgccct | gtgctgccct | ctggtgctct | ggccacctca | 1440 |
| atggccatgc | catgtgccag | accaaaacact | cgccctgggc | cgatggcaca | ccctgcgggc | 1500 |
| ccgcacaggc | ctgcatgggt | ggtcgctgcc | tccacatgga | ccagctccag | gacttcaata | 1560 |
| ttccacaggc | tggtggctgg | ggtccttggg | gaccatgggg | tgactgctct | cggacctgtg | 1620 |
| ggggtggtgt | ccagttctcc | tcccgagact | gcacgaggcc | tgtcccccgg | aatggtggca | 1680 |
| agtactgtga | gggccgccgt | acccgcttcc | gctcctgcaa | cactgaggac | tgcccgactg | 1740 |
| gctcagccct | gaccttccgc | gaggagcagt | gtgctgccta | caaccaccgc | accgacctct | 1800 |
| tcaagagctt | cccagggccc | atggactggg | ttcctcgcta | cacaggcgtg | gccccccagg | 1860 |
| accagtgcaa | actcacctgc | caggcccggg | cactgggcta | ctactatgtg | ctggagccac | 1920 |
| gggtggtaga | tgggaccccc | tgttcccgg | acagctcctc | ggtctgtgtc | cagggccgat | 1980 |
| gcatccatgc | tggctgtgat | cgcatcattg | gctccaagaa | gaagtttgac | aagtgcatgg | 2040 |
| tgtgcggagg | ggacggttct | ggttgcagca | agcagtcagg | ctccttcagg | aaattcaggt | 2100 |
| acggatacaa | caatgtggtc | actatccccg | cgggggccac | ccacattctt | gtccggcagc | 2160 |
| agggaaaccc | tggccaccgg | agcatctact | ggccctgaa | gctgccagat | ggctcctatg | 2220 |

-continued

```
ccctcaatgg tgaatacacg ctgatgccct cccccacaga tgtggtactg cctggggcag    2280
tcagcttgcg ctacagcggg gccactgcag cctcagagac actgtcaggc catgggccac    2340
tggcccagcc tttgacactg caggtcctag tggctggcaa ccccaggac acacgcctcc     2400 gatacagctt cttcgtgccc cggccgaccc cttcaacgcc acgcccact ccccaggact     2460 ggctgcaccg aagagcacag attctggaga tccttcggcg gcgccctgg gcgggcagga    2520 aataacctca ctatgcggcc gc                                             2542
```

<210> SEQ ID NO 15
<211> LENGTH: 625
<212> TYPE: PRT
<213> ORGANISM: Homo sapiens

<400> SEQUENCE: 15

```
Phe Ala Ser Leu Ser Arg Phe Val Glu Thr Leu Val Val Ala Asp Asp
 1               5                  10                  15

Lys Met Ala Ala Phe His Gly Ala Gly Leu Lys Arg Tyr Leu Leu Thr
                20                  25                  30

Val Met Ala Ala Ala Lys Ala Phe Lys His Pro Ser Ile Arg Asn
            35                  40                  45

Pro Val Ser Leu Val Val Thr Arg Leu Val Ile Leu Gly Ser Gly Glu
        50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His Met Asp Gln Leu Gln Asp Phe Asn
    290                 295                 300

Ile Pro Gln Ala Gly Gly Trp Gly Pro Trp Gly Pro Trp Gly Asp Cys
```

```
              305                 310                 315                 320
        Ser Arg Thr Cys Gly Gly Val Gln Phe Ser Arg Asp Cys Thr
                        325                 330                 335
        Arg Pro Val Pro Arg Asn Gly Gly Lys Tyr Cys Glu Gly Arg Arg Thr
                        340                 345                 350
        Arg Phe Arg Ser Cys Asn Thr Glu Asp Cys Pro Thr Gly Ser Ala Leu
                        355                 360                 365
        Thr Phe Arg Glu Glu Gln Cys Ala Ala Tyr Asn His Arg Thr Asp Leu
                    370                 375                 380
        Phe Lys Ser Phe Pro Gly Pro Met Asp Trp Val Pro Arg Tyr Thr Gly
        385                 390                 395                 400
        Val Ala Pro Gln Asp Gln Cys Lys Leu Thr Cys Gln Ala Arg Ala Leu
                        405                 410                 415
        Gly Tyr Tyr Tyr Val Leu Glu Pro Arg Val Val Asp Gly Thr Pro Cys
                        420                 425                 430
        Ser Pro Asp Ser Ser Val Cys Val Gln Gly Arg Cys Ile His Ala
                    435                 440                 445
        Gly Cys Asp Arg Ile Ile Gly Ser Lys Lys Phe Asp Lys Cys Met
                450                 455                 460
        Val Cys Gly Gly Asp Gly Ser Gly Cys Ser Lys Gln Ser Gly Ser Phe
        465                 470                 475                 480
        Arg Lys Phe Arg Tyr Gly Tyr Asn Asn Val Val Thr Ile Pro Ala Gly
                        485                 490                 495
        Ala Thr His Ile Leu Val Arg Gln Gln Gly Asn Pro Gly His Arg Ser
                    500                 505                 510
        Ile Tyr Leu Ala Leu Lys Leu Pro Asp Gly Ser Tyr Ala Leu Asn Gly
                    515                 520                 525
        Glu Tyr Thr Leu Met Pro Ser Pro Thr Asp Val Val Leu Pro Gly Ala
                530                 535                 540
        Val Ser Leu Arg Tyr Ser Gly Ala Thr Ala Ala Ser Glu Thr Leu Ser
        545                 550                 555                 560
        Gly His Gly Pro Leu Ala Gln Pro Leu Thr Leu Gln Val Leu Val Ala
                        565                 570                 575
        Gly Asn Pro Gln Asp Thr Arg Leu Arg Tyr Ser Phe Phe Val Pro Arg
                    580                 585                 590
        Pro Thr Pro Ser Thr Pro Arg Pro Thr Pro Gln Asp Trp Leu His Arg
                    595                 600                 605
        Arg Ala Gln Ile Leu Glu Ile Leu Arg Arg Pro Trp Ala Gly Arg
                610                 615                 620
        Lys
        625

<210> SEQ ID NO 16
<211> LENGTH: 1875
<212> TYPE: DNA
<213> ORGANISM: Homo sapiens

<400> SEQUENCE: 16
tttgcttcac tgagtagatt tgtggagaca ctggtggtgg cagatgacaa gatggccgca      60
ttccacggtg cggggctaaa gcgctacctg ctaacagtga tggcagcagc agccaaggcc     120
ttcaagcacc caagcatccg caatcctgtc agcttggtgg tgactcggct agtgatcctg     180
gggtcaggcg aggaggggcc ccaagtgggg cccagtgctg cccagaccct gcgcagcttc     240
tgtgcctggc agcggggcct caacacccct gaggactcgg accctgacca ctttgacaca     300
```

-continued

```
gccattctgt ttacccgtca ggacctgtgt ggagtctcca cttgcgacac gctgggtatg      360
gctgatgtgg gcaccgtctg tgacccggct cggagctgtg ccattgtgga ggatgatggg      420
ctccagtcag ccttcagtgc tgctcatcaa ctgggtcatg tcttcaacat gctccatgac      480
aactccaagc catgcatcag tttgaatggg cctttgagca cctctcgcca tgtcatggcc      540
cctgtgatgg ctcatgtgga tcctgaggag ccctggtccc cctgcagtgc ccgcttcatc      600
actgacttcc tggacaatgg ctatgggcac tgtctcttag acaaaccaga ggctccattg      660
catctgcctg tgactttccc tggcaaggac tatgatgctg accgccagtg ccagctgacc      720
ttcgggcccg actcacgcca ttgtccacag ctgccgccgc cctgtgctgc cctctggtgc      780
tctggccacc tcaatggcca tgccatgtgc cagaccaaac actcgccctg gccgatggc      840
acaccctgcg ggcccgcaca ggcctgcatg ggtggtcgct gcctccacat ggaccagctc      900
caggacttca atattccaca ggctggtggc tggggtcctt ggggaccatg gggtgactgc      960
tctcggacct gtgggggtgg tgtccagttc tcctcccgag actgcacgag gcctgtcccc     1020
cggaatggtg gcaagtactg tgagggccgc cgtacccgct tccgctcctg caacactgag     1080
gactgcccga ctggctcagc cctgaccttc cgcgaggagc agtgtgctgc ctacaaccac     1140
cgcaccgacc tcttcaagag cttcccaggg cccatggact gggttcctcg ctacacaggc     1200
gtggcccccc aggaccagtg caaactcacc tgccaggccc gggcactggg ctactactat     1260
gtgctggagc cacgggtggt agatgggacc ccctgttccc cggacagctc ctcggtctgt     1320
gtccagggcc gatgcatcca tgctggctgt gatcgcatca ttggctccaa gaagaagttt     1380
gacaagtgca tggtgtgcgg aggggacggt tctggttgca gcaagcagtc aggctccttc     1440
aggaaattca ggtacggata caacaatgtg gtcactatcc ccgcggggc cacccacatt     1500
cttgtccggc agcagggaaa ccctggccac ggagcatct acttggccct gaagctgcca     1560
gatggctcct atgccctcaa tggtgaatac acgctgatgc cctcccccac agatgtggta     1620
ctgcctgggg cagtcagctt cgcctacagc ggggccactg cagcctcaga gacactgtca     1680
ggccatgggc cactggccca gccttttgaca ctgcaggtcc tagtggctgg caaccccag     1740
gacacacgcc tccgatacag cttcttcgtg ccccggccga ccccttcaac gccacgcccc     1800
actcccagg actggctgca ccgaagagca cagattctgg agatccttcg gcggcgcccc     1860
tgggcgggca ggaaa                                                      1875
```

<210> SEQ ID NO 17
<211> LENGTH: 482
<212> TYPE: PRT
<213> ORGANISM: Homo sapiens

<400> SEQUENCE: 17

```
Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
            20                  25                  30

Val Met Ala Ala Ala Ala Lys Ala Phe Lys His Pro Ser Ile Arg Asn
        35                  40                  45

Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
```

```
                    85                  90                  95
His Phe Asp Thr Ala Ile Leu Phe Thr Arg Gln Asp Leu Cys Gly Val
                100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
                180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His Met Asp Gln Leu Gln Asp Phe Asn
    290                 295                 300

Ile Pro Gln Ala Gly Gly Trp Gly Pro Trp Gly Pro Trp Gly Asp Cys
305                 310                 315                 320

Ser Arg Thr Cys Gly Gly Gly Val Gln Phe Ser Ser Arg Asp Cys Thr
                325                 330                 335

Arg Pro Val Pro Arg Asn Gly Gly Lys Tyr Cys Glu Gly Arg Arg Thr
            340                 345                 350

Arg Phe Arg Ser Cys Asn Thr Glu Asp Cys Pro Thr Gly Ser Ala Leu
        355                 360                 365

Thr Phe Arg Glu Glu Gln Cys Ala Ala Tyr Asn His Arg Thr Asp Leu
    370                 375                 380

Phe Lys Ser Phe Pro Gly Pro Met Asp Trp Val Pro Arg Tyr Thr Gly
385                 390                 395                 400

Val Ala Pro Gln Asp Gln Cys Lys Leu Thr Cys Gln Ala Arg Ala Leu
                405                 410                 415

Gly Tyr Tyr Tyr Val Leu Glu Pro Arg Val Val Asp Gly Thr Pro Cys
            420                 425                 430

Ser Pro Asp Ser Ser Val Cys Val Gln Gly Arg Cys Ile His Ala
        435                 440                 445

Gly Cys Asp Arg Ile Ile Gly Ser Lys Lys Phe Asp Lys Cys Met
    450                 455                 460

Val Cys Gly Gly Asp Gly Ser Gly Cys Ser Lys Gln Ser Gly Ser Phe
465                 470                 475                 480

Arg Lys

<210> SEQ ID NO 18
<211> LENGTH: 1446
```

<212> TYPE: DNA
<213> ORGANISM: Homo sapiens

<400> SEQUENCE: 18

| | | | | | |
|---|---|---|---|---|---|
| tttgcttcac | tgagtagatt | tgtggagaca | ctggtggtgg | cagatgacaa | gatggccgca | 60 |
| ttccacggtg | cggggctaaa | gcgctacctg | ctaacagtga | tggcagcagc | agccaaggcc | 120 |
| ttcaagcacc | caagcatccg | caatcctgtc | agcttggtgg | tgactcggct | agtgatcctg | 180 |
| gggtcaggcg | aggaggggcc | ccaagtgggg | cccagtgctg | cccagaccct | gcgcagcttc | 240 |
| tgtgcctggc | agcggggcct | caacacccct | gaggactcgg | accctgacca | ctttgacaca | 300 |
| gccattctgt | ttacccgtca | ggacctgtgt | ggagtctcca | cttgcgacac | gctgggtatg | 360 |
| gctgatgtgg | gcaccgtctg | tgacccggct | cggagctgtg | ccattgtgga | ggatgatggg | 420 |
| ctccagtcag | ccttcagtgc | tgctcatcaa | ctgggtcatg | tcttcaacat | gctccatgac | 480 |
| aactccaagc | catgcatcag | tttgaatggg | cctttgagca | cctctcgcca | tgtcatggcc | 540 |
| cctgtgatgg | ctcatgtgga | tcctgaggag | ccctggtccc | cctgcagtgc | ccgcttcatc | 600 |
| actgacttcc | tggacaatgg | ctatgggcac | tgtctcttag | acaaaccaga | ggctccattg | 660 |
| catctgcctg | tgactttccc | tggcaaggac | tatgatgctg | accgccagtg | ccagctgacc | 720 |
| ttcgggcccg | actcacgcca | ttgtccacag | ctgccgccgc | cctgtgctgc | cctctggtgc | 780 |
| tctggccacc | tcaatggcca | tgccatgtgc | cagaccaaac | actcgccctg | gccgatggcc | 840 |
| acccctgcg | ggcccgcaca | ggcctgcatg | ggtggtcgct | gcctccacat | ggaccagctc | 900 |
| caggacttca | atattccaca | ggctggtggc | tggggtcctt | ggggaccatg | gggtgactgc | 960 |
| tctcggacct | gtgggggtgg | tgtccagttc | tcctcccgag | actgcacgag | gcctgtcccc | 1020 |
| cggaatggtg | gcaagtactg | tgagggccgc | cgtacccgct | tccgctcctg | caacactgag | 1080 |
| gactgcccga | ctggctcagc | cctgaccttc | cgcgaggagc | agtgtgctgc | ctacaaccac | 1140 |
| cgcaccgacc | tcttcaagag | ctttccaggg | cccatggact | gggttcctcg | ctacacaggc | 1200 |
| gtggcccccc | aggaccagtg | caaactcacc | tgccaggccc | gggcactggg | ctactactat | 1260 |
| gtgctggagc | cacgggtggt | agatgggacc | ccctgttccc | cggacagctc | ctcggtctgt | 1320 |
| gtccagggcc | gatgcatcca | tgctggctgt | gatcgcatca | ttggctccaa | gaagaagttt | 1380 |
| gacaagtgca | tggtgtgcgg | aggggacggt | tctggttgca | gcaagcagtc | aggctccttc | 1440 |
| aggaaa | | | | | | 1446 |

<210> SEQ ID NO 19
<211> LENGTH: 369
<212> TYPE: PRT
<213> ORGANISM: Homo sapiens

<400> SEQUENCE: 19

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
            20                  25                  30

Val Met Ala Ala Ala Ala Lys Ala Phe Lys His Pro Ser Ile Arg Asn
        35                  40                  45

Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp

```
                     85                  90                  95
His Phe Asp Thr Ala Ile Leu Phe Thr Arg Gln Asp Leu Cys Gly Val
                100                 105                 110
Ser Thr Cys Asp Thr Leu Gly Met Ala Asp Val Gly Thr Val Cys Asp
            115                 120                 125
Pro Ala Arg Ser Cys Ala Ile Val Glu Asp Asp Gly Leu Gln Ser Ala
        130                 135                 140
Phe Thr Ala Ala His Glu Leu Gly His Val Phe Asn Met Leu His Asp
145                 150                 155                 160
Asn Ser Lys Pro Cys Ile Ser Leu Asn Gly Pro Leu Ser Thr Ser Arg
                165                 170                 175
His Val Met Ala Pro Val Met Ala His Val Asp Pro Glu Glu Pro Trp
            180                 185                 190
Ser Pro Cys Ser Ala Arg Phe Ile Thr Asp Phe Leu Asp Asn Gly Tyr
        195                 200                 205
Gly His Cys Leu Leu Asp Lys Pro Glu Ala Pro Leu His Leu Pro Val
    210                 215                 220
Thr Phe Pro Gly Lys Asp Tyr Asp Ala Asp Arg Gln Cys Gln Leu Thr
225                 230                 235                 240
Phe Gly Pro Asp Ser Arg His Cys Pro Gln Leu Pro Pro Cys Ala
                245                 250                 255
Ala Leu Trp Cys Ser Gly His Leu Asn Gly His Ala Met Cys Gln Thr
            260                 265                 270
Lys His Ser Pro Trp Ala Asp Gly Thr Pro Cys Gly Pro Ala Gln Ala
        275                 280                 285
Cys Met Gly Gly Arg Cys Leu His Met Asp Gln Leu Gln Asp Phe Asn
    290                 295                 300
Ile Pro Gln Ala Gly Gly Trp Gly Pro Trp Gly Pro Trp Gly Asp Cys
305                 310                 315                 320
Ser Arg Thr Cys Gly Gly Gly Val Gln Phe Ser Ser Arg Asp Cys Thr
                325                 330                 335
Arg Pro Val Pro Arg Asn Gly Gly Lys Tyr Cys Glu Gly Arg Arg Thr
            340                 345                 350
Arg Phe Arg Ser Cys Asn Thr Glu Asp Cys Pro Thr Gly Ser Ala Leu
        355                 360                 365
Thr

<210> SEQ ID NO 20
<211> LENGTH: 1107
<212> TYPE: DNA
<213> ORGANISM: Homo sapiens

<400> SEQUENCE: 20
tttgcttcac tgagtagatt tgtggagaca ctggtggtgg cagatgacaa gatggccgca    60
ttccacggtg cggggctaaa gcgctacctg ctaacagtga tggcagcagc agccaaggcc   120
ttcaagcacc caagcatccg caatcctgtc agcttggtgg tgactcggct agtgatcctg   180
gggtcaggcg aggaggggcc ccaagtgggg cccagtgctg cccagaccct gcgcagcttc   240
tgtgcctggc agcggggcct caacacccct gaggactcgg accctgacca ctttgacaca   300
gccattctgt ttacccgtca ggacctgtgt ggagtctcca cttgcgacac gctgggtatg   360
gctgatgtgg gcaccgtctg tgacccggct cggagctgtg ccattgtgga ggatgatggg   420
ctccagtcag ccttcagtgc tgctcatcaa ctgggtcatg tcttcaacat gctccatgac   480
```

-continued

```
aactccaagc catgcatcag tttgaatggg cctttgagca cctctcgcca tgtcatggcc    540
cctgtgatgg ctcatgtgga tcctgaggag ccctggtccc cctgcagtgc ccgcttcatc    600
actgacttcc tggacaatgg ctatgggcac tgtctcttag acaaaccaga ggctccattg    660
catctgcctg tgactttccc tggcaaggac tatgatgctg accgccagtg ccagctgacc    720
ttcgggcccg actcacgcca ttgtccacag ctgccgccgc cctgtgctgc cctctggtgc    780
tctggccacc tcaatggcca tgccatgtgc agaccaaac actcgccctg gccgatggc     840 acaccctgcg ggcccgcaca ggcctgcatg ggtggtcgct gcctccacat ggaccagctc    900
caggacttca atattccaca ggctggtggc tggggtcctt ggggaccatg gggtgactgc    960
tctcggacct gtggggtgg tgtccagttc tcctcccgag actgcacgag gcctgtcccc    1020
cggaatggtg gcaagtactg tgagggccgc cgtacccgct ccgctcctg caacactgag    1080 gactgcccga ctggctcagc cctgacc                                       1107
```

<210> SEQ ID NO 21
<211> LENGTH: 5
<212> TYPE: PRT
<213> ORGANISM: Artificial
<220> FEATURE:
<223> OTHER INFORMATION: Neopeptide
<220> FEATURE:
<221> NAME/KEY: MISC_FEATURE
<222> LOCATION: (4)..(5)
<223> OTHER INFORMATION: X can be any amino acid

<400> SEQUENCE: 21

Ala Arg Gly Xaa Xaa
1               5

<210> SEQ ID NO 22
<211> LENGTH: 435
<212> TYPE: PRT
<213> ORGANISM: Artificial
<220> FEATURE:
<223> OTHER INFORMATION: Original catalytic construct

<400> SEQUENCE: 22

Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
        115                 120                 125

Thr Gly Thr Ile Asn Gly Asp Pro Glu Ser Val Ala Ser Leu His Trp
    130                 135                 140

Asp Gly Gly Ala Leu Leu Gly Val Leu Gln Tyr Arg Gly Ala Glu Leu
145                 150                 155                 160

His Leu Gln Pro Leu Glu Gly Thr Pro Asn Ser Ala Gly Pro
                165                 170                 175

Gly Ala His Ile Leu Arg Arg Lys Ser Pro Ala Ser Gly Gln Gly Pro
                180                 185                 190

Met Cys Asn Val Lys Ala Pro Leu Gly Ser Pro Ser Pro Arg Pro Arg
                195                 200                 205

Arg Ala Lys Arg Phe Ala Ser Leu Ser Arg Phe Val Glu Thr Leu Val
                210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
                260                 265                 270

Gly Ser Gly Glu Glu Gly Pro Gln Val Gly Pro Ser Ala Ala Gln Thr
                275                 280                 285

Leu Arg Ser Phe Cys Ala Trp Gln Arg Gly Leu Asn Thr Pro Glu Asp
                290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
                340                 345                 350

Leu Gln Ser Ala Phe Thr Ala Ala His Glu Leu Gly His Val Phe Asn
                355                 360                 365

Met Leu His Asp Asn Ser Lys Pro Cys Ile Ser Leu Asn Gly Pro Leu
                370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu His His
                420                 425                 430

His His His
        435

<210> SEQ ID NO 23
<211> LENGTH: 6
<212> TYPE: PRT
<213> ORGANISM: Artificial
<220> FEATURE:
<223> OTHER INFORMATION: His tag

<400> SEQUENCE: 23

His His His His His His
1               5

<210> SEQ ID NO 24
<211> LENGTH: 697
<212> TYPE: PRT
<213> ORGANISM: Artificial
<220> FEATURE:
<223> OTHER INFORMATION: Truncated ADAMTS4 molecule

<400> SEQUENCE: 24

Met Ser Gln Thr Gly Ser His Pro Gly Arg Gly Leu Ala Gly Arg Trp
1               5                   10                  15

```
Leu Trp Gly Ala Gln Pro Cys Leu Leu Leu Pro Ile Val Pro Leu Ser
             20                  25                  30

Trp Leu Val Trp Leu Leu Leu Leu Leu Ala Ser Leu Leu Pro Ser
         35                  40                  45

Ala Arg Leu Ala Ser Pro Leu Pro Arg Glu Glu Ile Val Phe Pro
 50                  55                  60

Glu Lys Leu Asn Gly Ser Val Leu Pro Gly Ser Gly Ala Pro Ala Arg
 65                  70                  75                  80

Leu Leu Cys Arg Leu Gln Ala Phe Gly Glu Thr Leu Leu Glu Leu
                 85                  90                  95

Glu Gln Asp Ser Gly Val Gln Val Glu Gly Leu Thr Val Gln Tyr Leu
                100                 105                 110

Gly Gln Ala Pro Glu Leu Leu Gly Gly Ala Glu Pro Gly Thr Tyr Leu
            115                 120                 125

Thr Gly Thr Ile Asn Gly Asp Pro Glu Ser Val Ala Ser Leu His Trp
        130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430
```

```
His Leu Pro Val Thr Phe Pro Gly Lys Asp Tyr Asp Ala Asp Arg Gln
            435                 440                 445

Cys Gln Leu Thr Phe Gly Pro Asp Ser Arg His Cys Pro Gln Leu Pro
        450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
        515                 520                 525

Trp Gly Asp Cys Ser Arg Thr Cys Gly Gly Gly Val Gln Phe Ser Ser
530                 535                 540

Arg Asp Cys Thr Arg Pro Val Pro Arg Asn Gly Gly Lys Tyr Cys Glu
545                 550                 555                 560

Gly Arg Arg Thr Arg Phe Arg Ser Cys Asn Thr Glu Asp Cys Pro Thr
                565                 570                 575

Gly Ser Ala Leu Thr Phe Arg Glu Glu Gln Cys Ala Ala Tyr Asn His
            580                 585                 590

Arg Thr Asp Leu Phe Lys Ser Phe Pro Gly Pro Met Asp Trp Val Pro
        595                 600                 605

Arg Tyr Thr Gly Val Ala Pro Gln Asp Gln Cys Lys Leu Thr Cys Gln
610                 615                 620

Ala Arg Ala Leu Gly Tyr Tyr Tyr Val Leu Glu Pro Arg Val Val Asp
625                 630                 635                 640

Gly Thr Pro Cys Ser Pro Asp Ser Ser Val Cys Val Gln Gly Arg
                645                 650                 655

Cys Ile His Ala Gly Cys Asp Arg Ile Ile Gly Ser Lys Lys Lys Phe
            660                 665                 670

Asp Lys Cys Met Val Cys Gly Gly Asp Gly Ser Gly Cys Ser Gly Ser
        675                 680                 685

Ala Trp Ser His Pro Gln Phe Glu Lys
    690                 695

<210> SEQ ID NO 25
<211> LENGTH: 11
<212> TYPE: PRT
<213> ORGANISM: Artificial
<220> FEATURE:
<223> OTHER INFORMATION: Construct C tag sequence

<400> SEQUENCE: 25

Gly Ser Ala Trp Ser His Pro Gln Phe Glu Lys
1               5                   10

<210> SEQ ID NO 26
<211> LENGTH: 686
<212> TYPE: PRT
<213> ORGANISM: Artificial
<220> FEATURE:
<223> OTHER INFORMATION: Truncated ADAMTS4 construct D

<400> SEQUENCE: 26

Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30
```

```
Trp Leu Val Trp Leu Leu Leu Leu Ala Ser Leu Leu Pro Ser
        35                  40                  45

Ala Arg Leu Ala Ser Pro Leu Pro Arg Glu Glu Ile Val Phe Pro
50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
                100                 105                 110

Gly Gln Ala Pro Glu Leu Leu Gly Ala Glu Pro Gly Thr Tyr Leu
        115                 120                 125

Thr Gly Thr Ile Asn Gly Asp Pro Glu Ser Val Ala Ser Leu His Trp
        130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
                180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
        210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
                260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
        290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
        340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
        370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
                420                 425                 430

His Leu Pro Val Thr Phe Pro Gly Lys Asp Tyr Asp Ala Asp Arg Gln
        435                 440                 445
```

```
Cys Gln Leu Thr Phe Gly Pro Asp Ser Arg His Cys Pro Gln Leu Pro
    450                 455                 460
Pro Pro Cys Ala Ala Leu Trp Cys Ser Gly His Leu Asn Gly His Ala
465                 470                 475                 480
Met Cys Gln Thr Lys His Ser Pro Trp Ala Asp Gly Thr Pro Cys Gly
                485                 490                 495
Pro Ala Gln Ala Cys Met Gly Gly Arg Cys Leu His Met Asp Gln Leu
            500                 505                 510
Gln Asp Phe Asn Ile Pro Gln Ala Gly Gly Trp Gly Pro Trp Gly Pro
        515                 520                 525
Trp Gly Asp Cys Ser Arg Thr Cys Gly Gly Val Gln Phe Ser Ser
    530                 535                 540
Arg Asp Cys Thr Arg Pro Val Pro Arg Asn Gly Gly Lys Tyr Cys Glu
545                 550                 555                 560
Gly Arg Arg Thr Arg Phe Arg Ser Cys Asn Thr Glu Asp Cys Pro Thr
                565                 570                 575
Gly Ser Ala Leu Thr Phe Arg Glu Glu Gln Cys Ala Ala Tyr Asn His
            580                 585                 590
Arg Thr Asp Leu Phe Lys Ser Phe Pro Gly Pro Met Asp Trp Val Pro
        595                 600                 605
Arg Tyr Thr Gly Val Ala Pro Gln Asp Gln Cys Lys Leu Thr Cys Gln
    610                 615                 620
Ala Arg Ala Leu Gly Tyr Tyr Tyr Val Leu Glu Pro Arg Val Val Asp
625                 630                 635                 640
Gly Thr Pro Cys Ser Pro Asp Ser Ser Val Cys Val Gln Gly Arg
                645                 650                 655
Cys Ile His Ala Gly Cys Asp Arg Ile Ile Gly Ser Lys Lys Lys Phe
            660                 665                 670
Asp Lys Cys Met Val Cys Gly Gly Asp Gly Ser Gly Cys Ser
        675                 680                 685
```

<210> SEQ ID NO 27
<211> LENGTH: 858
<212> TYPE: PRT
<213> ORGANISM: Artificial
<220> FEATURE:
<223> OTHER INFORMATION: modified ADAMTS4 molecule

<400> SEQUENCE: 27

```
Met Ser Gln Thr Gly Ser His Pro Gly Arg Gly Leu Ala Gly Arg Trp
1               5                   10                  15
Leu Trp Gly Ala Gln Pro Cys Leu Leu Leu Pro Ile Val Pro Leu Ser
                20                  25                  30
Trp Leu Val Trp Leu Leu Leu Leu Ala Ser Leu Leu Pro Ser
        35                  40                  45
Ala Arg Leu Ala Ser Pro Leu Pro Arg Glu Glu Ile Val Phe Pro
    50                  55                  60
Glu Lys Leu Asn Gly Ser Val Leu Pro Gly Ser Gly Ala Pro Ala Arg
65                  70                  75                  80
Leu Leu Cys Arg Leu Gln Ala Phe Gly Glu Thr Leu Leu Glu Leu
                85                  90                  95
Glu Gln Asp Ser Gly Val Gln Val Glu Gly Leu Thr Val Gln Tyr Leu
            100                 105                 110
Gly Gln Ala Pro Glu Leu Leu Gly Gly Ala Glu Pro Gly Thr Tyr Leu
        115                 120                 125
```

```
Thr Gly Thr Ile Asn Gly Asp Pro Glu Ser Val Ala Ser Leu His Trp
    130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Gly Ser Gly
            420                 425                 430

Ser Gly Asp Asp Asp Lys Ala Pro Leu His Leu Pro Val Thr Phe
        435                 440                 445

Pro Gly Lys Asp Tyr Asp Ala Asp Arg Gln Cys Gln Leu Thr Phe Gly
    450                 455                 460

Pro Asp Ser Arg His Cys Pro Gln Leu Pro Pro Cys Ala Ala Leu
465                 470                 475                 480

Trp Cys Ser Gly His Leu Asn Gly His Ala Met Cys Gln Thr Lys His
                485                 490                 495

Ser Pro Trp Ala Asp Gly Thr Pro Cys Gly Pro Ala Gln Ala Cys Met
            500                 505                 510

Gly Gly Arg Cys Leu His Met Asp Gln Leu Gln Asp Phe Asn Ile Pro
        515                 520                 525

Gln Ala Gly Gly Trp Gly Pro Trp Gly Pro Trp Gly Asp Cys Ser Arg
    530                 535                 540

Thr Cys Gly Gly Gly Val Gln Phe Ser Ser Arg Asp Cys Thr Arg Pro
```

-continued

```
            545                 550                 555                 560

Val Pro Arg Asn Gly Gly Lys Tyr Cys Glu Gly Arg Thr Arg Phe
                        565                 570                 575

Arg Ser Cys Asn Thr Glu Asp Cys Pro Thr Gly Ser Ala Leu Thr Phe
                    580                 585                 590

Arg Glu Glu Gln Cys Ala Ala Tyr Asn His Arg Thr Asp Leu Phe Lys
                595                 600                 605

Ser Phe Pro Gly Pro Met Asp Trp Val Pro Arg Tyr Thr Gly Val Ala
            610                 615                 620

Pro Gln Asp Gln Cys Lys Leu Thr Cys Gln Ala Arg Ala Leu Gly Tyr
        625                 630                 635                 640

Tyr Tyr Val Leu Glu Pro Arg Val Val Asp Gly Thr Pro Cys Ser Pro
                        645                 650                 655

Asp Ser Ser Val Cys Val Gln Gly Arg Cys Ile His Ala Gly Cys
                    660                 665                 670

Asp Arg Ile Ile Gly Ser Lys Lys Lys Phe Asp Lys Cys Met Val Cys
                675                 680                 685

Gly Gly Asp Gly Ser Gly Cys Ser Lys Gln Ser Gly Ser Phe Arg Lys
            690                 695                 700

Phe Arg Tyr Gly Tyr Asn Asn Val Val Thr Ile Pro Ala Gly Ala Thr
        705                 710                 715                 720

His Ile Leu Val Arg Gln Gln Gly Asn Pro Gly His Arg Ser Ile Tyr
                        725                 730                 735

Leu Ala Leu Lys Leu Pro Asp Gly Ser Tyr Ala Leu Asn Gly Glu Tyr
                    740                 745                 750

Thr Leu Met Pro Ser Pro Thr Asp Val Val Leu Pro Gly Ala Val Ser
                755                 760                 765

Leu Arg Tyr Ser Gly Ala Thr Ala Ala Ser Glu Thr Leu Ser Gly His
            770                 775                 780

Gly Pro Leu Ala Gln Pro Leu Thr Leu Gln Val Leu Val Ala Gly Asn
        785                 790                 795                 800

Pro Gln Asp Thr Arg Leu Arg Tyr Ser Phe Phe Val Pro Arg Pro Thr
                        805                 810                 815

Pro Ser Thr Pro Arg Pro Thr Pro Gln Asp Trp Leu His Arg Arg Ala
                    820                 825                 830

Gln Ile Leu Glu Ile Leu Arg Arg Pro Trp Ala Gly Arg Lys Gly
                835                 840                 845

Ser Ala Trp Ser His Pro Gln Phe Glu Lys
            850                 855

<210> SEQ ID NO 28
<211> LENGTH: 10
<212> TYPE: PRT
<213> ORGANISM: Artificial
<220> FEATURE:
<223> OTHER INFORMATION: construct E insertion sequence

<400> SEQUENCE: 28

Gly Ser Gly Ser Gly Asp Asp Asp Asp Lys
1               5                   10

<210> SEQ ID NO 29
<211> LENGTH: 846
<212> TYPE: PRT
<213> ORGANISM: Artificial
<220> FEATURE:
<223> OTHER INFORMATION: ADAMTS4 with active-site mutation
```

<400> SEQUENCE: 29

```
Met Ser Gln Thr Gly Ser His Pro Gly Arg Gly Leu Ala Gly Arg Trp
1               5                   10                  15

Leu Trp Gly Ala Gln Pro Cys Leu Leu Pro Ile Val Pro Leu Ser
            20                  25                  30

Trp Leu Val Trp Leu Leu Leu Leu Ala Ser Leu Leu Pro Ser
        35                  40                  45

Ala Arg Leu Ala Ser Pro Leu Pro Arg Glu Glu Ile Val Phe Pro
    50                  55                  60

Glu Lys Leu Asn Gly Ser Val Leu Pro Gly Ser Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
                100                 105                 110

Gly Gln Ala Pro Glu Leu Leu Gly Ala Glu Pro Gly Thr Tyr Leu
            115                 120                 125

Thr Gly Thr Ile Asn Gly Asp Pro Glu Ser Val Ala Ser Leu His Trp
130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
            195                 200                 205

Arg Ala Lys Arg Phe Ala Ser Leu Ser Arg Phe Val Glu Thr Leu Val
            210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
    275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
            325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Gln Leu Gly His Val Phe Asn
    355                 360                 365

Met Leu His Asp Asn Ser Lys Pro Cys Ile Ser Leu Asn Gly Pro Leu
370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
```

-continued

```
                405                 410                 415
Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
            435                 440                 445

Cys Gln Leu Thr Phe Gly Pro Asp Ser Arg His Cys Pro Gln Leu Pro
            450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
            485                 490                 495

Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
            515                 520                 525

Trp Gly Asp Cys Ser Arg Thr Cys Gly Gly Gly Val Gln Phe Ser Ser
            530                 535                 540

Arg Asp Cys Thr Arg Pro Val Pro Arg Asn Gly Gly Lys Tyr Cys Glu
545                 550                 555                 560

Gly Arg Arg Thr Arg Phe Arg Ser Cys Asn Thr Glu Asp Cys Pro Thr
            565                 570                 575

Gly Ser Ala Leu Thr Phe Arg Glu Glu Gln Cys Ala Ala Tyr Asn His
            580                 585                 590

Arg Thr Asp Leu Phe Lys Ser Phe Pro Gly Pro Met Asp Trp Val Pro
            595                 600                 605

Arg Tyr Thr Gly Val Ala Pro Gln Asp Gln Cys Lys Leu Thr Cys Gln
            610                 615                 620

Ala Arg Ala Leu Gly Tyr Tyr Tyr Val Leu Glu Pro Arg Val Val Asp
625                 630                 635                 640

Gly Thr Pro Cys Ser Pro Asp Ser Ser Val Cys Val Gln Gly Arg
            645                 650                 655

Cys Ile His Ala Gly Cys Asp Arg Ile Ile Gly Ser Lys Lys Lys Phe
            660                 665                 670

Asp Lys Cys Met Val Cys Gly Gly Asp Gly Ser Gly Cys Ser Lys Gln
            675                 680                 685

Ser Gly Ser Phe Arg Lys Phe Arg Tyr Gly Tyr Asn Asn Val Val Thr
            690                 695                 700

Ile Pro Ala Gly Ala Thr His Ile Leu Val Arg Gln Gln Gly Asn Pro
705                 710                 715                 720

Gly His Arg Ser Ile Tyr Leu Ala Leu Lys Leu Pro Asp Gly Ser Tyr
            725                 730                 735

Ala Leu Asn Gly Glu Tyr Thr Leu Met Pro Ser Pro Thr Asp Val Val
            740                 745                 750

Leu Pro Gly Ala Val Ser Leu Arg Tyr Ser Gly Ala Thr Ala Ala Ser
            755                 760                 765

Glu Thr Leu Ser Gly His Gly Pro Leu Ala Gln Pro Leu Thr Leu Gln
            770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
            805                 810                 815

Trp Leu His Arg Arg Ala Gln Ile Leu Glu Ile Leu Arg Arg Pro
            820                 825                 830
```

Trp Ala Gly Arg Lys Val Asp Tyr Lys Asp Asp Asp Lys
            835                 840                 845

<210> SEQ ID NO 30
<211> LENGTH: 9
<212> TYPE: PRT
<213> ORGANISM: Artificial
<220> FEATURE:
<223> OTHER INFORMATION: FLAG tag sequence

<400> SEQUENCE: 30

Val Asp Tyr Lys Asp Asp Asp Asp Lys
1               5

<210> SEQ ID NO 31
<211> LENGTH: 584
<212> TYPE: PRT
<213> ORGANISM: Artificial
<220> FEATURE:
<223> OTHER INFORMATION: Truncated ADAMTS4 ASM

<400> SEQUENCE: 31

Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Ala Ser Leu Leu Pro Ser
            35                  40                  45

Ala Arg Leu Ala Ser Pro Leu Pro Arg Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
                100                 105                 110

Gly Gln Ala Pro Glu Leu Leu Gly Gly Ala Glu Pro Gly Thr Tyr Leu
            115                 120                 125

Thr Gly Thr Ile Asn Gly Asp Pro Glu Ser Val Ala Ser Leu His Trp
130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr

-continued

```
            275                 280                 285
Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
                340                 345                 350

Leu Gln Ser Ala Phe Thr Ala Ala His Gln Leu Gly His Val Phe Asn
            355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
        435                 440                 445

Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
        515                 520                 525

Trp Gly Asp Cys Ser Arg Thr Cys Gly Gly Val Gln Phe Ser Ser
    530                 535                 540

Arg Asp Cys Thr Arg Pro Val Pro Arg Asn Gly Gly Lys Tyr Cys Glu
545                 550                 555                 560

Gly Arg Arg Thr Arg Phe Arg Ser Cys Asn Thr Glu Asp Cys Pro Val
                565                 570                 575

Asp Tyr Lys Asp Asp Asp Asp Lys
            580
```

<210> SEQ ID NO 32
<211> LENGTH: 529
<212> TYPE: PRT
<213> ORGANISM: Artificial
<220> FEATURE:
<223> OTHER INFORMATION: Truncated ADAMTS4 ASM

<400> SEQUENCE: 32

```
Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
```

-continued

```
                50                  55                  60
Glu Lys Leu Asn Gly Ser Val Leu Pro Gly Ser Gly Ala Pro Ala Arg
 65                  70                  75                  80

Leu Leu Cys Arg Leu Gln Ala Phe Gly Glu Thr Leu Leu Glu Leu
                 85                  90                  95

Glu Gln Asp Ser Gly Val Gln Val Glu Gly Leu Thr Val Gln Tyr Leu
                100                 105                 110

Gly Gln Ala Pro Glu Leu Leu Gly Ala Glu Pro Gly Thr Tyr Leu
                115                 120                 125

Thr Gly Thr Ile Asn Gly Asp Pro Glu Ser Val Ala Ser Leu His Trp
    130                 135                 140

Asp Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
                180                 185                 190

Met Cys Asn Val Lys Ala Pro Leu Gly Ser Pro Ser Pro Arg Pro Arg
            195                 200                 205

Arg Ala Lys Arg Phe Ala Ser Leu Ser Arg Phe Val Glu Thr Leu Val
            210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
                260                 265                 270

Gly Ser Gly Glu Glu Gly Pro Gln Val Gly Pro Ser Ala Ala Gln Thr
            275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Gln Leu Gly His Val Phe Asn
    355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
                420                 425                 430

His Leu Pro Val Thr Phe Pro Gly Lys Asp Tyr Asp Ala Asp Arg Gln
            435                 440                 445

Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480
```

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala Val Asp Tyr Lys Asp Asp Asp
        515                 520                 525

Lys

<210> SEQ ID NO 33
<211> LENGTH: 42
<212> TYPE: DNA
<213> ORGANISM: Artificial
<220> FEATURE:
<223> OTHER INFORMATION: PCR primer

<400> SEQUENCE: 33
taaatcgaat tcccaccatg tcccagacag gctcgcatcc cg                    42

<210> SEQ ID NO 34
<211> LENGTH: 37
<212> TYPE: DNA
<213> ORGANISM: Artificial
<220> FEATURE:
<223> OTHER INFORMATION: PCR primer

<400> SEQUENCE: 34
tattatgtct actgggcagt cctcagtgtt gcaggag                          37

<210> SEQ ID NO 35
<211> LENGTH: 37
<212> TYPE: DNA
<213> ORGANISM: Artificial
<220> FEATURE:
<223> OTHER INFORMATION: PCR primer

<400> SEQUENCE: 35
tattatgtct acagcctgtg gaatattgaa gtcctgg                          37

<210> SEQ ID NO 36
<211> LENGTH: 53
<212> TYPE: DNA
<213> ORGANISM: Artificial
<220> FEATURE:
<223> OTHER INFORMATION: Flag1 sequence

<400> SEQUENCE: 36
aattcctatg ctagtgctat cgtagactac aaggatgacg atgacaagta agc         53

<210> SEQ ID NO 37
<211> LENGTH: 53
<212> TYPE: DNA
<213> ORGANISM: Artificial
<220> FEATURE:
<223> OTHER INFORMATION: Flag2 sequence

<400> SEQUENCE: 37
ggccgcttac ttgtcatcgt catccttgta gtctacgata gcactagcat agg         53

<210> SEQ ID NO 38
<211> LENGTH: 3916
<212> TYPE: DNA
<213> ORGANISM: Artificial
<220> FEATURE:
<223> OTHER INFORMATION: cloning vector

<400> SEQUENCE: 38

```
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagcttg   240
gtaccgagct cggatccact agtaacggcc gccagtgtgc tggaattcct atgctagtgc   300
tatcgtagac tacaaggatg acgatgacaa gtaagcggcc gctcgagcat gcatctagag   360
ggcccaattc gccctatagt gagtcgtatt acaattcact ggccgtcgtt ttacaacgtc   420
gtgactggga aaaccctggc gttacccaac ttaatcgcct tgcagcacat cccccttttcg  480
ccagctggcg taatagcgaa gaggcccgca ccgatcgccc ttcccaacag ttgcgcagcc   540
tgaatggcga atgggacgcg ccctgtagcg gcgcattaag cgcggcgggt gtggtggtta   600
cgcgcagcgt gaccgctaca cttgccagcg ccctagcgcc cgctcctttc gctttcttcc   660
cttcctttct cgccacgttc gccggctttc cccgtcaagc tctaaatcgg ggctcccctt   720
tagggttccg atttagagct ttacggcacc tcgaccgcaa aaaacttgat ttgggtgatg   780
gttcacgtag tgggccatcg ccctgataga cggtttttcg ccctttgacg ttggagtcca   840
cgttctttaa tagtggactc ttgttccaaa ctggaacaac actcaaccct atcgcggtct   900
attcttttga tttataaggg attttgccga tttcggccta ttggttaaaa atgagctga   960
tttaacaaat tcagggcgca agggctgcta aggaaccgg aacacgtaga aagccagtcc  1020
gcagaaacgg tgctgacccc ggatgaatgt cagctactgg gctatctgga caagggaaaa  1080
cgcaagcgca aagagaaagc aggtagcttg cagtgggctt acatggcgat agctagactg  1140
ggcggtttta tggacagcaa gcgaaccgga attgccagct ggggcgccct ctggtaaggt  1200
tgggaagccc tgcaaagtaa actggatggc tttcttgccg ccaaggatct gatgcgcag  1260
gggatcaaga tctgatcaag agacaggatg aggatcgttt cgcatgattg aacaagatgg  1320
attgcacgca ggttctccgg ccgcttgggt ggagaggcta ttcggctatg actgggcaca  1380
acagacaatc ggctgctctg atgccgccgt gttccggctg tcagcgcagg ggcgcccggt  1440
tcttttttgtc aagaccgacc tgtccggtgc cctgaatgaa ctgcaggacg aggcagcgcg  1500
gctatcgtgg ctggccacga cgggcgttcc ttgcgcagct gtgctcgacg ttgtcactga  1560
agcgggaagg gactggctgc tattgggcga agtgccgggg caggatctcc tgtcatctcg  1620
ccttgctcct gccgagaaag tatccatcat ggctgatgca atgcggcggc tgcatacgct  1680
tgatccggct acctgcccat tcgaccacca agcgaaacat cgcatcgagc gagcacgtac  1740
tcggatggaa gccggtcttg tcgatcagga tgatctggac gaagagcatc aggggctcgc  1800
gccagccgaa ctgttcgcca ggctcaaggc gcgcatgccc gacggcgagg atctcgtcgt  1860
gatccatggc gatgcctgct tgccgaatat catggtggaa aatggccgct ttctggatt   1920
caacgactgt ggccggctgg gtgtggcgga ccgctatcag acatagcgt tggatacccg  1980
tgatattgct gaagagcttg gcggcgaatg ggctgaccgc ttcctcgtgc tttacggtat  2040
cgccgctccc gattcgcagc gcatcgcctt ctatcgcctt cttgacgagt tcttctgaat  2100
tgaaaaagga agagtatgag tattcaacat ttccgtgtcg cccttattcc cttttttgcg  2160
gcattttgcc ttcctgtttt tgctcaccca gaaacgctgg tgaaagtaaa agatgctgaa  2220
gatcagttgg gtgcacgagt gggttacatc gaactggatc tcaacagcgg taagatcctt  2280
```

-continued

```
gagagttttc gccccgaaga acgttttcca atgatgagca cttttaaagt tctgctatgt      2340
catacactat tatcccgtat tgacgccggg caagagcaac tcggtcgccg ggcgcggtat      2400
tctcagaatg acttggttga gtactcacca gtcacagaaa agcatcttac ggatggcatg      2460
acagtaagag aattatgcag tgctgccata accatgagtg ataacactgc ggccaactta      2520
cttctgacaa cgatcggagg accgaaggag ctaaccgctt ttttgcacaa catgggggat      2580
catgtaactc gccttgatcg ttgggaaccg gagctgaatg aagccatacc aaacgacgag      2640
agtgacacca cgatgcctgt agcaatgcca acaacgttgc gcaaactatt aactggcgaa      2700
ctacttactc tagcttcccg gcaacaatta atagactgga tggaggcgga taaagttgca      2760
ggaccacttc tgcgctcggc ccttccggct ggctggttta ttgctgataa atctggagcc      2820
ggtgagcgtg ggtctcgcgg tatcattgca gcactggggc cagatggtaa gccctcccgt      2880
atcgtagtta tctacacgac ggggagtcag gcaactatgg atgaacgaaa tagacagatc      2940
gctgagatag gtgcctcact gattaagcat tggtaactgt cagaccaagt ttactcatat      3000
atactttaga ttgatttaaa acttcatttt taatttaaaa ggatctaggt gaagatcctt      3060
tttgataatc tcatgaccaa aatcccttaa cgtgagtttt cgttccactg agcgtcagac      3120
cccgtagaaa agatcaaagg atcttcttga gatcctttt tctgcgcgt aatctgctgc       3180
ttgcaaacaa aaaaccacc gctaccagcg gtggtttgtt tgccggatca agagctacca       3240
actcttttc cgaaggtaac tggcttcagc agagcgcaga taccaaatac tgtccttcta      3300
gtgtagccgt agttaggcca ccacttcaag aactctgtag caccgcctac atacctcgct      3360
ctgctaatcc tgttaccagt ggctgctgcc agtggcgata agtcgtgtct taccgggttg      3420
gactcaagac gatagttacc ggataaggcg cagcggtcgg gctgaacggg gggttcgtgc      3480
acacagccca gcttggagcg aacgacctac accgaactga gatacctaca gcgtgagcat      3540
tgagaaagcg ccacgcttcc cgaagggaga aaggcggaca ggtatccggt aagcggcagg      3600
gtcggaacag gagagcgcac gagggagctt ccaggggggaa acgcctggta tctttatagt      3660
cctgtcgggt ttcgccacct ctgacttgag cgtcgatttt tgtgatgctc gtcaggggg       3720
cggagcctat ggaaaaacgc cagcaacgcg gccttttac ggttcctggc cttttgctgg       3780
ccttttgctc acatgttctt tcctgcgtta tcccctgatt ctgtggataa ccgtattacc      3840
gcctttgagt gagctgatac cgctcgccgc agccgaacga ccgagcgcag cgagtcagtg      3900
agcgaggaag cggaag                                                     3916
```

<210> SEQ ID NO 39
<211> LENGTH: 5676
<212> TYPE: DNA
<213> ORGANISM: Artificial
<220> FEATURE:
<223> OTHER INFORMATION: cloning vector

<400> SEQUENCE: 39

```
aagctcgagc gcgggacgtc ctttgtttac gtcccgtcgg cgctgaatcc cgcggacgac        60
ccctctcggg gccgcttggg agtctctcgt cccttctcc gtctgccgtt ccagccgacc        120
acggggcgca cctctctttta cgcggtctcc ccgtctgtgc cttctcatct gccggtccgt      180
gtgcacttcg cttcacctct gcacgttgca tggagaccac cgtgaacgcc catcagatcc      240
tgcccaaggt cttacataag aggactcttg gactctcagc aatgtcaacg accgaccttg      300
aggcctactt caaagactgt gtgtttaagg actgggagga gctggggggag agattaggt     360
taaaggtctt tgtattagga ggctgtaggc ataaattggt ctgcgcacca gcaccatgca      420
```

-continued

| | |
|---|---|
| acttttttcac ctctgcctaa tcatctcttg tacatgtccc actgttcaag cctccaagct | 480 |
| gtgccttggg tggctttggg gcatggacat tgacccttat aaagaatttg gagctactgt | 540 |
| ggagttactc tcgtttttgc cttctgactt ctttccttcc gtcagctcga gtttaccact | 600 |
| ccctatcagt gatagagaaa agtgaaagtc gagtttacca ctccctatca gtgatagaga | 660 |
| aaagtgaaag tcgaggtcga gtttaccact ccctatcagt gatagagaaa agtgaaagtc | 720 |
| gaggtcgagt ttaccactcc ctatcagtga tagagaaaag tgaaagtcga gtttaccact | 780 |
| ccctatcagt gatagagaaa agtgaaagtc gaggtcgagt ttaccactcc ctatcagtga | 840 |
| tagaaaagtg aaagtgaaag tcgaggtcga gtcgaggggg gctataaaag ggggtggggg | 900 |
| cgcgttcgtc ctcactctct tccgcatcgc tgtctgcgag ggccagctgt tgggctcgcg | 960 |
| gttgaggaca aactcttcgc ggtctttcca gtactcttgg atcggaaacc cgtcggcctc | 1020 |
| cgaacggtac tccgccaccg agggacctga gcgagtccgc atcgaccgga tcggaaaacc | 1080 |
| tctcgactgt tggggtgagt actccctctc aaaagcgggc atgacttctg cgctaagatt | 1140 |
| gtcagtttcc aaaaacgagg aggatttgat attcacctgg cccgcggtga tgcctttgag | 1200 |
| ggtggccgcg tccatctggt cagaaaagac aatctttttg ttgtcaagct tgaggtgtgg | 1260 |
| caggcttgag atctggccat acacttgagt gacaatgaca tccactttgc ctttctctcc | 1320 |
| acaggtgtcc actcccaggt ccaactgcag acttcgaatt ctactgagtc gacacttcta | 1380 |
| gactacccgg gaatgcggcc gccgcaaatt ctaacgttac tggccgaagc cgcttggaat | 1440 |
| aaggccggtg tgcgtttgtc tatatgttat tttccaccat attgccgtct tttggcaatg | 1500 |
| tgagggcccg gaaacctggc cctgtcttct tgacgagcat tcctaggggt ctttcccctc | 1560 |
| tcgccaaagg aatgcaaggt ctgttgaatg tcgtgaagga agcagttcct ctggaagctt | 1620 |
| cttgaagaca acaacgtct gtagcgaccc tttgcaggca gcggaacccc ccacctggcg | 1680 |
| acaggtgcct ctgcggccaa aagccacgtg tataagatac acctgcaaag gcggcacaac | 1740 |
| cccagtgcca cgttgtgagt tggatagttg tggaaagagt caaatggctc tcctcaagcg | 1800 |
| tattcaacaa ggggctgaag gatgcccaga aggtacccca ttgtatggga tctgatctgg | 1860 |
| ggcctcggtg cacatgcttt acatgtgttt agtcgaggtt aaaaaacgtc taggcccccc | 1920 |
| gaaccacggg gacgtggttt tcctttgaaa acacgattg ctcgagccat catggttcga | 1980 |
| ccattgaact gcatcgtcgc cgtgtcccaa aatatgggga ttggcaagaa cggagaccta | 2040 |
| ccctggcctc cgctcaggaa cgagttcaag tacttccaaa gaatgaccac aacctcttca | 2100 |
| gtggaaggta acagaatct ggtgattatg ggtaggaaaa cctggttctc cattcctgag | 2160 |
| aagaatcgac ctttaaagga cagaattaat atagttctca gtagagaact caaagaacca | 2220 |
| ccacgaggag ctcattttct tgccaaaagt ttggatgatg ccttaagact tattgaacaa | 2280 |
| ccggaattgg caagtaaagt agacatggtt tggatagtcg gaggcagttc tgtttaccag | 2340 |
| gaagccatga atcaaccagg ccacctcaga ctctttgtga caaggatcat gcaggaattt | 2400 |
| gaaagtgaca cgttttttccc agaaattgat ttgggggaaat ataaacttct cccagaatac | 2460 |
| ccaggcgtcc tctctgaggt ccaggaggaa aaaggcatca agtataagtt tgaagtctac | 2520 |
| gagaagaaag actaacagga agatgctttc aagttctctg ctccctcct aaagctatgc | 2580 |
| atttttttata agaccatggg acttttgctg gctttagatc ataatcagcc ataccacatt | 2640 |
| tgtagaggtt ttacttgctt taaaaaacct cccacacctc cccctgaacc tgaaacataa | 2700 |
| aatgaatgca attgttgttg ttaacttgtt tattgcagct tataatggtt acaaataaag | 2760 |

```
caatagcatc acaaatttca caaataaagc attttttttca ctgcattcta gttgtggttt    2820
gtccaaactc atcaatgtat cttatcatgt ctggatcccc ggccaacggt ctggtgaccc    2880
ggctgcgaga gctcggtgta cctgagacgc gagtaagccc ttgagtcaaa gacgtagtcg    2940
ttgcaagtcc gcaccaggta ctgatcatcg atgctagacc gtgcaaaagg agagcctgta    3000
agcgggcact cttccgtggt ctggtggata aattcgcaag ggtatcatgg cggacgaccg    3060
gggttcgaac cccggatccg gccgtccgcc gtgatccatc cggttaccgc ccgcgtgtcg    3120
aacccaggtg tgcgacgtca gacaacgggg gagcgctcct tttggcttcc ttccaggcgc    3180
ggcggctgct gcgctagctt ttttggcgag ctcgaattaa ttctgcatta atgaatcggc    3240
caacgcgcgg ggagaggcgg tttgcgtatt gggcgctctt ccgcttcctc gctcactgac    3300
tcgctgcgct cggtcgttcg gctgcggcga gcggtatcag ctcactcaaa ggcggtaata    3360
cggttatcca cagaatcagg ggataacgca ggaaagaaca tgtgagcaaa aggccagcaa    3420
aaggccagga accgtaaaaa ggccgcgttg ctggcgtttt tccataggct ccgcccccct    3480
gacgagcatc acaaaaatcg acgctcaagt cagaggtggc gaaacccgac aggactataa    3540
agataccagg cgtttccccc tggaagctcc ctcgtgcgct ctcctgttcc gaccctgccg    3600
cttaccggat acctgtccgc ctttctccct tcgggaagcg tggcgctttc tcaatgctca    3660
cgctgtaggt atctcagttc ggtgtaggtc gttcgctcca agctgggctg tgtgcacgaa    3720
ccccccgttc agcccgaccg ctgcgcctta tccggtaact atcgtcttga gtccaacccg    3780
gtaagacacg acttatcgcc actggcagca gccactggta acaggattag cagagcgagg    3840
tatgtaggcg gtgctacaga gttcttgaag tggtggccta actacggcta cactagaagg    3900
acagtatttg gtatctgcgc tctgctgaag ccagttacct tcggaaaaag agttggtagc    3960
tcttgatccg gcaaacaaac caccgctggt agcggtggtt tttttgtttg caagcagcag    4020
attacgcgca gaaaaaaagg atcctttga tcttttctac ggggtctgac    4080
gctcagtgga acgaaaactc acgttaaggg attttggtca tgagattatc aaaaaggatc    4140
ttcacctaga tccttttaaa ttaaaaatga agttttaaat caatctaaag tatatatgag    4200
taaacttggt ctgacagtta ccaatgctta atcagtgagg cacctatctc agcgatctgt    4260
ctatttcgtt catccatagt tgcctgactc cccgtcgtgt agataactac gatacgggag    4320
ggcttaccat ctggccccag tgctgcaatg ataccgcgag acccacgctc accggctcca    4380
gatttatcag caataaacca gccagccgga agggccgagc gcagaagtgg tcctgcaact    4440
ttatccgcct ccatccagtc tattaattgt tgccgggaag ctagagtaag tagttcgcca    4500
gttaatagtt tgcgcaacgt tgttgccatt gctacaggca tcgtggtgtc acgctcgtcg    4560
tttggtatgg cttcattcag ctccggttcc caacgatcaa ggcgagttac atgatccccc    4620
atgttgtgca aaaaagcggt tagctccttc ggtcctccga tcgttgtcag aagtaagttg    4680
gccgcagtgt tatcactcat ggttatggca gcactgcata attctcttac tgtcatgcca    4740
tccgtaagat gcttttctgt gactggtgag tactcaacca agtcattctg agaatagtgt    4800
atgcggcgac cgagttgctc ttgcccggcg tcaatacggg ataataccgc gccacatagc    4860
agaactttaa aagtgctcat cattggaaaa cgttcttcgg ggcgaaaact ctcaaggatc    4920
ttaccgctgt tgagatccag ttcgatgtaa cccactcgtg cacccaactg atcttcagca    4980
tcttttactt tcaccagcgt ttctgggtga gcaaaaacag gaaggcaaaa tgccgcaaaa    5040
aagggaataa gggcgacacg gaaatgttga atactcatac tcttcctttt tcaatattat    5100
tgaagcattt atcagggtta ttgtctcatg agcggataca tatttgaatg tatttagaaa    5160
```

-continued

```
aataaacaaa tagggggttcc gcgcacattt ccccgaaaag tgccacctga cgtctaagaa    5220
accattatta tcatgacatt aacctataaa aataggcgta tcacgaggcc ctttcgtctc    5280
gcgcgtttcg gtgatgacgg tgaaaacctc tgacacatgc agctcccgga gacggtcaca    5340
gcttgtctgt aagcggatgc cgggagcaga caagcccgtc agggcgcgtc agcgggtgtt    5400
ggcgggtgtc ggggctggct taactatgcg gcatcagagc agattgtact gagagtgcac    5460
catatgcggt gtgaaatacc gcacagatgc gtaaggagaa ataccgcat caggcgccat     5520 tcgccattca ggctgcgcaa ctgttgggaa gggcgatcgg tgcgggcctc ttcgctatta    5580
cgccagctgg cgaaaggggg atgtgctgca aggcgattaa gttgggtaac gccagggttt    5640
tcccagtcac gacgttgtaa aacgacggcc agtgcc                              5676
```

<210> SEQ ID NO 40
<211> LENGTH: 845
<212> TYPE: PRT
<213> ORGANISM: Artificial
<220> FEATURE:
<223> OTHER INFORMATION: ADAMTS4 ASM with insertion

<400> SEQUENCE: 40

```
Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
        115                 120                 125

Thr Gly Thr Ile Asn Gly Asp Pro Glu Ser Val Ala Ser Leu His Trp
130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270
```

```
Gly Ser Gly Glu Glu Gly Pro Gln Val Gly Ser Ala Ala Gln Thr
            275                 280                 285

Leu Arg Ser Phe Cys Ala Trp Gln Arg Gly Leu Asn Thr Pro Glu Asp
        290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Gln Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
        435                 440                 445

Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Arg Cys Leu His Met Asp Gln Leu
            500                 505                 510

Gln Asp Phe Asn Ile Pro Gln Trp Ser His Pro Gln Phe Glu Lys Ala
        515                 520                 525

Gly Gly Trp Gly Pro Trp Gly Pro Trp Gly Asp Cys Ser Arg Thr Cys
530                 535                 540

Gly Gly Gly Val Gln Phe Ser Ser Arg Asp Cys Thr Arg Pro Val Pro
545                 550                 555                 560

Arg Asn Gly Gly Lys Tyr Cys Glu Gly Arg Arg Thr Arg Phe Arg Ser
                565                 570                 575

Cys Asn Thr Glu Asp Cys Pro Thr Gly Ser Ala Leu Thr Phe Arg Glu
            580                 585                 590

Glu Gln Cys Ala Ala Tyr Asn His Arg Thr Asp Leu Phe Lys Ser Phe
        595                 600                 605

Pro Gly Pro Met Asp Trp Val Pro Arg Tyr Thr Gly Val Ala Pro Gln
    610                 615                 620

Asp Gln Cys Lys Leu Thr Cys Gln Ala Arg Ala Leu Gly Tyr Tyr Tyr
625                 630                 635                 640

Val Leu Glu Pro Arg Val Val Asp Gly Thr Pro Cys Ser Pro Asp Ser
                645                 650                 655

Ser Ser Val Cys Val Gln Gly Arg Cys Ile His Ala Gly Cys Asp Arg
            660                 665                 670

Ile Ile Gly Ser Lys Lys Lys Phe Asp Lys Cys Met Val Cys Gly Gly
        675                 680                 685
```

-continued

```
Asp Gly Ser Gly Cys Ser Lys Gln Ser Gly Ser Phe Arg Lys Phe Arg
            690                 695                 700

Tyr Gly Tyr Asn Asn Val Val Thr Ile Pro Ala Gly Ala Thr His Ile
705                 710                 715                 720

Leu Val Arg Gln Gln Gly Asn Pro Gly His Arg Ser Ile Tyr Leu Ala
                725                 730                 735

Leu Lys Leu Pro Asp Gly Ser Tyr Ala Leu Asn Gly Glu Tyr Thr Leu
                740                 745                 750

Met Pro Ser Pro Thr Asp Val Val Leu Pro Gly Ala Val Ser Leu Arg
            755                 760                 765

Tyr Ser Gly Ala Thr Ala Ala Ser Glu Thr Leu Ser Gly His Gly Pro
            770                 775                 780

Leu Ala Gln Pro Leu Thr Leu Gln Val Leu Val Ala Gly Asn Pro Gln
785                 790                 795                 800

Asp Thr Arg Leu Arg Tyr Ser Phe Phe Val Pro Arg Pro Thr Pro Ser
                805                 810                 815

Thr Pro Arg Pro Thr Pro Gln Asp Trp Leu His Arg Arg Ala Gln Ile
            820                 825                 830

Leu Glu Ile Leu Arg Arg Arg Pro Trp Ala Gly Arg Lys
            835                 840                 845
```

<210> SEQ ID NO 41
<211> LENGTH: 8
<212> TYPE: PRT
<213> ORGANISM: Artificial
<220> FEATURE:
<223> OTHER INFORMATION: strep tag

<400> SEQUENCE: 41

Trp Ser His Pro Gln Phe Glu Lys
1               5

<210> SEQ ID NO 42
<211> LENGTH: 15
<212> TYPE: DNA
<213> ORGANISM: Artificial
<220> FEATURE:
<223> OTHER INFORMATION: DNA insert

<400> SEQUENCE: 42
catgggcagc tcgag                                                         15

<210> SEQ ID NO 43
<211> LENGTH: 34
<212> TYPE: DNA
<213> ORGANISM: Artificial
<220> FEATURE:
<223> OTHER INFORMATION: insert in pMT21

<400> SEQUENCE: 43
ctgcaggcga gcctgaattc ctcgagccat catg                                    34

<210> SEQ ID NO 44
<211> LENGTH: 8
<212> TYPE: DNA
<213> ORGANISM: Artificial
<220> FEATURE:
<223> OTHER INFORMATION: Cla1 linker

<400> SEQUENCE: 44 catcgatg                                                                  8

<210> SEQ ID NO 45
<211> LENGTH: 68
<212> TYPE: DNA
<213> ORGANISM: Artificial
<220> FEATURE:
<223> OTHER INFORMATION: DNA adaptor

<400> SEQUENCE: 45
cgaggttaaa aaacgtctag gcccccccgaa ccacggggac gtggttttcc tttgaaaaac    60
acgattgc                                                              68

<210> SEQ ID NO 46
<211> LENGTH: 223
<212> TYPE: PRT
<213> ORGANISM: Artificial
<220> FEATURE:
<223> OTHER INFORMATION: furin-processed construct B

<400> SEQUENCE: 46

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
            20                  25                  30

Val Met Ala Ala Ala Lys Ala Phe Lys His Pro Ser Ile Arg Asn
        35                  40                  45

Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu His His His His His His
    210                 215                 220

<210> SEQ ID NO 47
<211> LENGTH: 485
<212> TYPE: PRT
<213> ORGANISM: Artificial
<220> FEATURE:
<223> OTHER INFORMATION: furin-processed construct C

<400> SEQUENCE: 47

Phe Ala Ser Leu Ser Arg Phe Val Glu Thr Leu Val Val Ala Asp Asp
1               5                   10                  15

-continued

```
Lys Met Ala Ala Phe His Gly Ala Gly Leu Lys Arg Tyr Leu Leu Thr
         20                  25                  30

Val Met Ala Ala Ala Lys Ala Phe Lys His Pro Ser Ile Arg Asn
         35                  40                  45

Pro Val Ser Leu Val Val Thr Arg Leu Val Ile Leu Gly Ser Gly Glu
 50                  55                  60

Glu Gly Pro Gln Val Gly Pro Ser Ala Ala Gln Thr Leu Arg Ser Phe
 65                  70                  75                  80

Cys Ala Trp Gln Arg Gly Leu Asn Thr Pro Glu Asp Ser Asp Pro Asp
                 85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
                260                 265                 270

Lys His Ser Pro Trp Ala Asp Gly Thr Pro Cys Gly Pro Ala Gln Ala
            275                 280                 285

Cys Met Gly Gly Arg Cys Leu His Met Asp Gln Leu Gln Asp Phe Asn
        290                 295                 300

Ile Pro Gln Ala Gly Gly Trp Gly Pro Trp Gly Pro Trp Gly Asp Cys
305                 310                 315                 320

Ser Arg Thr Cys Gly Gly Val Gln Phe Ser Ser Arg Asp Cys Thr
                325                 330                 335

Arg Pro Val Pro Arg Asn Gly Gly Lys Tyr Cys Glu Gly Arg Arg Thr
                340                 345                 350

Arg Phe Arg Ser Cys Asn Thr Glu Asp Cys Pro Thr Gly Ser Ala Leu
            355                 360                 365

Thr Phe Arg Glu Glu Gln Cys Ala Ala Tyr Asn His Arg Thr Asp Leu
        370                 375                 380

Phe Lys Ser Phe Pro Gly Pro Met Asp Trp Val Pro Arg Tyr Thr Gly
385                 390                 395                 400

Val Ala Pro Gln Asp Gln Cys Lys Leu Thr Cys Gln Ala Arg Ala Leu
                405                 410                 415

Gly Tyr Tyr Tyr Val Leu Glu Pro Arg Val Val Asp Gly Thr Pro Cys
                420                 425                 430

Ser Pro Asp Ser Ser Ser Val Cys Val Gln Gly Arg Cys Ile His Ala
```

```
                435                 440                 445
Gly Cys Asp Arg Ile Ile Gly Ser Lys Lys Phe Asp Lys Cys Met
    450                 455                 460

Val Cys Gly Gly Asp Gly Ser Gly Cys Ser Gly Ser Ala Trp Ser His
465                 470                 475                 480

Pro Gln Phe Glu Lys
            485

<210> SEQ ID NO 48
<211> LENGTH: 474
<212> TYPE: PRT
<213> ORGANISM: Artificial
<220> FEATURE:
<223> OTHER INFORMATION: furin-processed construct D

<400> SEQUENCE: 48

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
                20                  25                  30

Val Met Ala Ala Ala Lys Ala Phe Lys His Pro Ser Ile Arg Asn
            35                  40                  45

Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His Met Asp Gln Leu Gln Asp Phe Asn
    290                 295                 300

Ile Pro Gln Ala Gly Gly Trp Gly Pro Trp Gly Pro Trp Gly Asp Cys
```

-continued

```
             305                 310                 315                 320
Ser Arg Thr Cys Gly Gly Val Gln Phe Ser Arg Asp Cys Thr
                325                 330                 335

Arg Pro Val Pro Arg Asn Gly Gly Lys Tyr Cys Glu Gly Arg Arg Thr
                340                 345                 350

Arg Phe Arg Ser Cys Asn Thr Glu Asp Cys Pro Thr Gly Ser Ala Leu
                355                 360                 365

Thr Phe Arg Glu Glu Gln Cys Ala Ala Tyr Asn His Arg Thr Asp Leu
            370                 375                 380

Phe Lys Ser Phe Pro Gly Pro Met Asp Trp Val Pro Arg Tyr Thr Gly
385                 390                 395                 400

Val Ala Pro Gln Asp Gln Cys Lys Leu Thr Cys Gln Ala Arg Ala Leu
                405                 410                 415

Gly Tyr Tyr Tyr Val Leu Glu Pro Arg Val Val Asp Gly Thr Pro Cys
                420                 425                 430

Ser Pro Asp Ser Ser Val Cys Val Gln Gly Arg Cys Ile His Ala
                435                 440                 445

Gly Cys Asp Arg Ile Ile Gly Ser Lys Lys Phe Asp Lys Cys Met
450                 455                 460

Val Cys Gly Gly Asp Gly Ser Gly Cys Ser
465                 470

<210> SEQ ID NO 49
<211> LENGTH: 646
<212> TYPE: PRT
<213> ORGANISM: Artificial
<220> FEATURE:
<223> OTHER INFORMATION: furin-processed construct E

<400> SEQUENCE: 49

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
                20                  25                  30

Val Met Ala Ala Ala Lys Ala Phe Lys His Pro Ser Ile Arg Asn
                35                  40                  45

Pro Val Ser Leu Val Val Thr Arg Leu Val Ile Leu Gly Ser Gly Glu
            50                  55                  60

Glu Gly Pro Gln Val Gly Pro Ser Ala Ala Gln Thr Leu Arg Ser Phe
65              70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
                100                 105                 110

Ser Thr Cys Asp Thr Leu Gly Met Ala Asp Val Gly Thr Val Cys Asp
            115                 120                 125

Pro Ala Arg Ser Cys Ala Ile Val Glu Asp Asp Gly Leu Gln Ser Ala
            130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
```

```
                195                 200                 205
Gly His Cys Leu Leu Asp Lys Pro Glu Ala Pro Leu His Leu Pro Val
    210                 215                 220
Gly Ser Gly Ser Gly Asp Asp Asp Lys Thr Phe Pro Gly Lys Asp
225                 230                 235                 240
Tyr Asp Ala Asp Arg Gln Cys Gln Leu Thr Phe Gly Pro Asp Ser Arg
                245                 250                 255
His Cys Pro Gln Leu Pro Pro Cys Ala Ala Leu Trp Cys Ser Gly
            260                 265                 270
His Leu Asn Gly His Ala Met Cys Gln Thr Lys His Ser Pro Trp Ala
        275                 280                 285
Asp Gly Thr Pro Cys Gly Pro Ala Gln Ala Cys Met Gly Arg Cys
    290                 295                 300
Leu His Met Asp Gln Leu Gln Asp Phe Asn Ile Pro Gln Ala Gly Gly
305                 310                 315                 320
Trp Gly Pro Trp Gly Pro Trp Gly Asp Cys Ser Arg Thr Cys Gly Gly
                325                 330                 335
Gly Val Gln Phe Ser Ser Arg Asp Cys Thr Arg Pro Val Pro Arg Asn
            340                 345                 350
Gly Gly Lys Tyr Cys Glu Gly Arg Arg Thr Arg Phe Arg Ser Cys Asn
        355                 360                 365
Thr Glu Asp Cys Pro Thr Gly Ser Ala Leu Thr Phe Arg Glu Glu Gln
    370                 375                 380
Cys Ala Ala Tyr Asn His Arg Thr Asp Leu Phe Lys Ser Phe Pro Gly
385                 390                 395                 400
Pro Met Asp Trp Val Pro Arg Tyr Thr Gly Val Ala Pro Gln Asp Gln
                405                 410                 415
Cys Lys Leu Thr Cys Gln Ala Arg Ala Leu Gly Tyr Tyr Val Leu
            420                 425                 430
Glu Pro Arg Val Val Asp Gly Thr Pro Cys Ser Pro Asp Ser Ser Ser
        435                 440                 445
Val Cys Val Gln Gly Arg Cys Ile His Ala Gly Cys Asp Arg Ile Ile
    450                 455                 460
Gly Ser Lys Lys Lys Phe Asp Lys Cys Met Val Cys Gly Gly Asp Gly
465                 470                 475                 480
Ser Gly Cys Ser Lys Gln Ser Gly Ser Phe Arg Lys Phe Arg Tyr Gly
                485                 490                 495
Tyr Asn Asn Val Val Thr Ile Pro Ala Gly Ala Thr His Ile Leu Val
            500                 505                 510
Arg Gln Gln Gly Asn Pro Gly His Arg Ser Ile Tyr Leu Ala Leu Lys
        515                 520                 525
Leu Pro Asp Gly Ser Tyr Ala Leu Asn Gly Glu Tyr Thr Leu Met Pro
    530                 535                 540
Ser Pro Thr Asp Val Val Leu Pro Gly Ala Val Ser Leu Arg Tyr Ser
545                 550                 555                 560
Gly Ala Thr Ala Ala Ser Glu Thr Leu Ser Gly His Gly Pro Leu Ala
                565                 570                 575
Gln Pro Leu Thr Leu Gln Val Leu Val Ala Gly Asn Pro Gln Asp Thr
            580                 585                 590
Arg Leu Arg Tyr Ser Phe Phe Val Pro Arg Pro Thr Pro Ser Thr Pro
        595                 600                 605
Arg Pro Thr Pro Gln Asp Trp Leu His Arg Arg Ala Gln Ile Leu Glu
    610                 615                 620
```

-continued

```
Ile Leu Arg Arg Arg Pro Trp Ala Gly Arg Lys Gly Ser Ala Trp Ser
625                 630                 635                 640

His Pro Gln Phe Glu Lys
            645

<210> SEQ ID NO 50
<211> LENGTH: 634
<212> TYPE: PRT
<213> ORGANISM: Artificial
<220> FEATURE:
<223> OTHER INFORMATION: furin-processed construct G

<400> SEQUENCE: 50

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
            20                  25                  30

Val Met Ala Ala Ala Lys Ala Phe Lys His Pro Ser Ile Arg Asn
        35                  40                  45

Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
130                 135                 140

Phe Thr Ala Ala His Gln Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His Met Asp Gln Leu Gln Asp Phe Asn
290                 295                 300

Ile Pro Gln Ala Gly Gly Trp Gly Pro Trp Gly Pro Trp Gly Asp Cys
305                 310                 315                 320

Ser Arg Thr Cys Gly Gly Gly Val Gln Phe Ser Ser Arg Asp Cys Thr
                325                 330                 335
```

```
Arg Pro Val Pro Arg Asn Gly Gly Lys Tyr Cys Glu Gly Arg Arg Thr
            340                 345                 350

Arg Phe Arg Ser Cys Asn Thr Glu Asp Cys Pro Thr Gly Ser Ala Leu
            355                 360                 365

Thr Phe Arg Glu Glu Gln Cys Ala Ala Tyr Asn His Arg Thr Asp Leu
            370                 375                 380

Phe Lys Ser Phe Pro Gly Pro Met Asp Trp Val Pro Arg Tyr Thr Gly
385                 390                 395                 400

Val Ala Pro Gln Asp Gln Cys Lys Leu Thr Cys Gln Ala Arg Ala Leu
            405                 410                 415

Gly Tyr Tyr Tyr Val Leu Glu Pro Arg Val Val Asp Gly Thr Pro Cys
            420                 425                 430

Ser Pro Asp Ser Ser Val Cys Val Gln Gly Arg Cys Ile His Ala
            435                 440                 445

Gly Cys Asp Arg Ile Ile Gly Ser Lys Lys Phe Asp Lys Cys Met
450                 455                 460

Val Cys Gly Gly Asp Gly Ser Gly Cys Ser Lys Gln Ser Gly Ser Phe
465                 470                 475                 480

Arg Lys Phe Arg Tyr Gly Tyr Asn Asn Val Val Thr Ile Pro Ala Gly
            485                 490                 495

Ala Thr His Ile Leu Val Arg Gln Gln Gly Asn Pro Gly His Arg Ser
            500                 505                 510

Ile Tyr Leu Ala Leu Lys Leu Pro Asp Gly Ser Tyr Ala Leu Asn Gly
            515                 520                 525

Glu Tyr Thr Leu Met Pro Ser Pro Thr Asp Val Val Leu Pro Gly Ala
            530                 535                 540

Val Ser Leu Arg Tyr Ser Gly Ala Thr Ala Ala Ser Glu Thr Leu Ser
545                 550                 555                 560

Gly His Gly Pro Leu Ala Gln Pro Leu Thr Leu Gln Val Leu Val Ala
            565                 570                 575

Gly Asn Pro Gln Asp Thr Arg Leu Arg Tyr Ser Phe Phe Val Pro Arg
            580                 585                 590

Pro Thr Pro Ser Thr Pro Arg Pro Thr Pro Gln Asp Trp Leu His Arg
            595                 600                 605

Arg Ala Gln Ile Leu Glu Ile Leu Arg Arg Pro Trp Ala Gly Arg
            610                 615                 620

Lys Val Asp Tyr Lys Asp Asp Asp Lys
625                 630

<210> SEQ ID NO 51
<211> LENGTH: 372
<212> TYPE: PRT
<213> ORGANISM: Artificial
<220> FEATURE:
<223> OTHER INFORMATION: furin-processed construct H

<400> SEQUENCE: 51

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
130                 135                 140

Phe Thr Ala Ala His Gln Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His Met Asp Gln Leu Gln Asp Phe Asn
290                 295                 300

Ile Pro Gln Ala Gly Gly Trp Gly Pro Trp Gly Pro Trp Gly Asp Cys
305                 310                 315                 320

Ser Arg Thr Cys Gly Gly Gly Val Gln Phe Ser Ser Arg Asp Cys Thr
                325                 330                 335

Arg Pro Val Pro Arg Asn Gly Gly Lys Tyr Cys Glu Gly Arg Arg Thr
            340                 345                 350

Arg Phe Arg Ser Cys Asn Thr Glu Asp Cys Pro Val Asp Tyr Lys Asp
        355                 360                 365

Asp Asp Asp Lys
370

<210> SEQ ID NO 52
<211> LENGTH: 317
<212> TYPE: PRT
<213> ORGANISM: Artificial
<220> FEATURE:
<223> OTHER INFORMATION: furin-processed construct I

<400> SEQUENCE: 52

Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
            20                  25                  30

Val Met Ala Ala Ala Ala Lys Ala Phe Lys His Pro Ser Ile Arg Asn
        35                  40                  45

```
Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Gln Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
                260                 265                 270

Lys His Ser Pro Trp Ala Asp Gly Thr Pro Cys Gly Pro Ala Gln Ala
            275                 280                 285

Cys Met Gly Gly Arg Cys Leu His Met Asp Gln Leu Gln Asp Phe Asn
    290                 295                 300

Ile Pro Gln Ala Val Asp Tyr Lys Asp Asp Asp Lys
305                 310                 315
```

<210> SEQ ID NO 53
<211> LENGTH: 633
<212> TYPE: PRT
<213> ORGANISM: Artificial
<220> FEATURE:
<223> OTHER INFORMATION: furin-processed construct F

<400> SEQUENCE: 53

```
Phe Ala Ser Leu Ser Arg Phe Val Glu Thr Leu Val Val Ala Asp Asp
1               5                   10                  15

Lys Met Ala Ala Phe His Gly Ala Gly Leu Lys Arg Tyr Leu Leu Thr
                20                  25                  30

Val Met Ala Ala Ala Lys Ala Phe Lys His Pro Ser Ile Arg Asn
            35                  40                  45

Pro Val Ser Leu Val Val Thr Arg Leu Val Ile Leu Gly Ser Gly Glu
    50                  55                  60

Glu Gly Pro Gln Val Gly Pro Ser Ala Ala Gln Thr Leu Arg Ser Phe
65                  70                  75                  80

Cys Ala Trp Gln Arg Gly Leu Asn Thr Pro Glu Asp Ser Asp Pro Asp
                85                  90                  95
```

```
His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Gln Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
                275                 280                 285

Cys Met Gly Gly Arg Cys Leu His Met Trp Ser His Pro Gln Phe Glu
    290                 295                 300

Lys Asp Gln Leu Gln Asp Phe Asn Ile Pro Gln Ala Gly Gly Trp Gly
305                 310                 315                 320

Pro Trp Gly Pro Trp Gly Asp Cys Ser Arg Thr Cys Gly Gly Gly Val
                325                 330                 335

Gln Phe Ser Ser Arg Asp Cys Thr Arg Pro Val Pro Arg Asn Gly Gly
            340                 345                 350

Lys Tyr Cys Glu Gly Arg Arg Thr Arg Phe Arg Ser Cys Asn Thr Glu
        355                 360                 365

Asp Cys Pro Thr Gly Ser Ala Leu Thr Phe Arg Glu Glu Gln Cys Ala
    370                 375                 380

Ala Tyr Asn His Arg Thr Asp Leu Phe Lys Ser Phe Pro Gly Pro Met
385                 390                 395                 400

Asp Trp Val Pro Arg Tyr Thr Gly Val Ala Pro Gln Asp Gln Cys Lys
                405                 410                 415

Leu Thr Cys Gln Ala Arg Ala Leu Gly Tyr Tyr Val Leu Glu Pro
            420                 425                 430

Arg Val Val Asp Gly Thr Pro Cys Ser Pro Asp Ser Ser Val Cys
        435                 440                 445

Val Gln Gly Arg Cys Ile His Ala Gly Cys Asp Arg Ile Ile Gly Ser
    450                 455                 460

Lys Lys Lys Phe Asp Lys Cys Met Val Cys Gly Gly Asp Gly Ser Gly
465                 470                 475                 480

Cys Ser Lys Gln Ser Gly Ser Phe Arg Lys Phe Arg Tyr Gly Tyr Asn
                485                 490                 495

Asn Val Val Thr Ile Pro Ala Gly Ala Thr His Ile Leu Val Arg Gln
            500                 505                 510
```

-continued

```
Gln Gly Asn Pro Gly His Arg Ser Ile Tyr Leu Ala Leu Lys Leu Pro
        515                 520                 525

Asp Gly Ser Tyr Ala Leu Asn Gly Glu Tyr Thr Leu Met Pro Ser Pro
        530                 535                 540

Thr Asp Val Val Leu Pro Gly Ala Val Ser Leu Arg Tyr Ser Gly Ala
545                 550                 555                 560

Thr Ala Ala Ser Glu Thr Leu Ser Gly His Gly Pro Leu Ala Gln Pro
                565                 570                 575

Leu Thr Leu Gln Val Leu Val Ala Gly Asn Pro Gln Asp Thr Arg Leu
                580                 585                 590

Arg Tyr Ser Phe Phe Val Pro Arg Pro Thr Pro Ser Thr Pro Arg Pro
        595                 600                 605

Thr Pro Gln Asp Trp Leu His Arg Arg Ala Gln Ile Leu Glu Ile Leu
        610                 615                 620

Arg Arg Arg Pro Trp Ala Gly Arg Lys
625                 630
```

MODIFIED ADAMTS4 MOLECULES AND METHOD OF USE THEREOF

RELATED APPLICATIONS

This application claims the benefit of priority of U.S. Provisional Patent Application Ser. No. 60/398,721, filed Jul. 29, 2002, the entire disclosure of which is incorporated by reference herein.

FIELD OF THE INVENTION

The present invention relates to modified aggrecanases, nucleotides encoding such enzymes, and processes for producing these enzymes. The invention further relates to the development of inhibitors of, as well as antibodies to, the modified aggrecanase. These inhibitors and antibodies may be useful for the treatment of various aggrecanase-associated conditions including osteoarthritis.

BACKGROUND OF THE INVENTION

Aggrecan is a major extracellular component of articular cartilage. It is a proteoglycan responsible for providing cartilage with its mechanical properties of compressibility and elasticity. The loss of aggrecan has been implicated in the degradation of articular cartilage in arthritic diseases such as osteoarthritis.

Aggrecan contains two N-terminal globular domains, G1 and G2, separated by a proteolytically-sensitive interglobular domain, followed by a glycosaminoglycan attachment region and a C-terminal globular domain, G3. At least two enzymatic cleavage sites have been identified within the interglobular domain of aggrecan. One enzymatic cleavage site within the interglobular domain of aggrecan (asn341-phe342) has been observed to be cleaved by several known metalloproteases. Cleavage at a second aggrecan cleavage site within aggrecan (glu373-ala374) has been attributed to aggrecanase activity. The cleavage site (glu373-ala374) is therefore referred to as the aggrecanase cleavage site.

A number of aggrecanases have been cloned in recent years. These enzymes belong to a subfamily of zinc metalloproteases referred to as "ADAMTS," an abbreviation for A Disintegrin-like And Metalloprotease domain with ThromboSpondin type I motifs. The ADAMTS family currently consists of 19 members that are related to one another on the basis of their common domain structure. Typical ADAMTS proteins contain a classic signal sequence upstream of a pro-sequence ending in a furin cleavage site, a metalloprotease domain that is well conserved among family members, a disintegrin-like motif whose functional relevance is still unknown, and at least one thrombospondin type I (TSP 1) domain. ADAMTS family members differ in the number of TSP-1 domains they contain, which can range from 1 to 15 (Cal et al., 2002; Somerville et al., 2003). The most diverse region of the ADAMTS sequence is the 'spacer' domain located downstream of a cysteine-rich region containing 10 structurally conserved cysteine residues. ADAMTS proteins are capable of associating with components of the extracellular matrix through interactions within the spacer domain and the TSP-1 motif(s) (Kuno and Matsushima, 1998; Tortorella et al., 2000).

ADAMTS4 (aggrecanase-1) is synthesized by IL-1 stimulated cartilage (Tortorella, et al., Science, 284:1664–1666, 1999) and is related to the degradation of aggrecan during degenerative joint diseases such as osteoarthritis (Abbaszade et al., J Biol Chem, 274: 23443–23450, 1999). ADAMTS4 is also involved in the cleavage of brain-enriched hyaluranan binding (BEHAB)/brevican, a protein that is dramatically increased in human gliomas (Matthews et al., J. Biol. Chem. 275:22695–22703, 2000). It is thus possible to ameliorate osteoarthritis and any other ADAMTS4-related diseases by inhibiting the aggrecanase activity of ADAMTS4. However, research effects on ADAMTS4 have been hampered by the instability of purified ADAMTS4 proteins.

SUMMARY OF THE INVENTION

The present invention is based on the observation that the full-length, furin-processed ADAMTS4 molecules are capable of undergoing auto-catalytic C-terminal truncation. The auto-digested ADAMTS4 molecules exhibited markedly reduced affinity of binding to sulfated glycosaminoglycans (GAGs) but retained aggrecanase activity. Further studies revealed that ADAMTS molecules with modified domain structures can be enzymatically active while having improved stability compared to the native enzyme. For example, it was found that modified ADAMTS4 molecules with truncated spacer domain or no spacer domain are biologically active and are more stable than their full-length counterparts. The modified ADAMTS proteins can be expressed and isolated in large quantities, thus allowing further characterization of the proteins, such as crystallographic and enzyme kinetic studies. The purified, stable proteins would also facilitate the production of anti-ADAMTS antibodies and the development of inhibitors to ADAMTS enzymes.

One aspect of the present invention pertains to modified ADAMTS4 (mTS4) proteins; nucleotide sequences which encode mTS4 proteins; and processes for the production of mTS4 proteins. Preferably, the mTS4 proteins of the present invention are more stable and can be expressed at levels higher than that of their full-length counterparts. More preferably, the mTS4 proteins of the present invention are more stable and biologically active.

In one embodiment, the invention provides isolated mTS4 proteins that are biologically active. The mTS4 proteins may be produced by standard recombinant DNA technology or by auto-digestion of furin-processed full-length ADAMTS4 molecules. The embodiment specifically includes mTS4 proteins having the amino acid sequences recited in SEQ ID NOS:17, 19, 22, 24, 26, 27, and 46–49, as well as variants and fragments thereof. These proteins may be used, for example, for the characterization of ADAMTS4 enzyme, production of anti-ADAMTS4 antibodies, and screening of ADAMTS4 inhibitors.

In another embodiment, the invention provides isolated mTS4 proteins that are not biologically active but are more stable than the native protein. The embodiment specifically includes mTS4 proteins having the amino acid sequences recited in SEQ ID NOS:29, 31, 32, 40 and 50–53, as well as variants and fragments thereof. These proteins may be used, for example, in crystallographic studies.

In another embodiment, the invention provides isolated mTS4 proteins comprising a ADAMTS4 portion and a non-ADAMTS4 portion. The non-ADAMTS4 portion of the mTS4 protein may serve as a tag to facilitate immune-recognition or protein purification, or as a signal sequence to enhance secretion. The non-ADAMTS4-containing mTS4 proteins can be used, for example, to produce anti-mTS4 antibodies in a subject, to purify ADAMTS4 ligands, and to identify molecules that inhibit the interaction of the ADAMTS4 protein with an ADAMTS4 substrate in screening assays.

In another embodiment, the invention features nucleic acid molecules that encode the mTS4 proteins of the present invention. The embodiment specifically includes isolated polynucleotide molecules comprising a nucleotide sequence encoding a polypeptide comprising an amino acid sequence selected from the group consisting of SEQ ID NOS:17, 19, 22, 24, 26, 27, 29, 31, 32, 40 and 46–53.

In another embodiment, the invention provides vectors comprising nucleotide sequences encoding mTS4 proteins of the present invention. These vectors may be employed in a novel process for producing mTS4 proteins of the present invention.

Another aspect of the present invention pertains to anti-mTS4 antibodies, inhibitors of mTS4, and methods for treating an aggrecanase-related disease using anti-mTS4 antibodies or inhibitors of mTS4.

In one embodiment, the mTS4 protein of the present invention are used for the development of inhibitors of aggrecanases and antibodies to aggrecanases for treatment of aggrecanase-related diseases such as osteoarthritis. The embodiment specifically includes methods for identifying and developing inhibitors of aggrecanase that block the enzyme's activity.

In another embodiment, the invention provides pharmaceutical compositions for inhibiting the activity of aggrecanases, wherein the compositions comprise an anti-mTS4 antibody and/or an inhibitor of mTS4 of the present invention, and a pharmaceutical carrier. In another embodiment, the invention provides methods for inhibiting aggrecanase activity in a mammal comprising administering to the mammal an effective amount of a pharmaceutical composition comprising an anti-mTS4 antibody and/or an inhibitor of mTS4 of the present invention.

In yet another embodiment, the invention provides methods for treating patients suffering from conditions characterized by a degradation of aggrecan or preventing such conditions. These methods entail administering to a patient needing such treatment an effective amount of a pharmaceutical composition comprising an anti-mTS4 antibody and/or an inhibitor of mTS4 of the present invention.

Additional aspects of the disclosure will be set forth in part in the description, will in part be obvious from the description, and/or may be learned from practicing the invention. The invention is set forth and particularly pointed out in the claims, and the disclosure should not be construed as limiting the scope of the claims. The following detailed description includes exemplary representations of various embodiments of the invention which are not restrictive of the invention as claimed. The accompanying figures constitute a part of this specification and, together with the description, serve to illustrate embodiments and not limit the invention.

DETAILED DESCRIPTION OF THE INVENTION

I. Definitions

Figure 1:
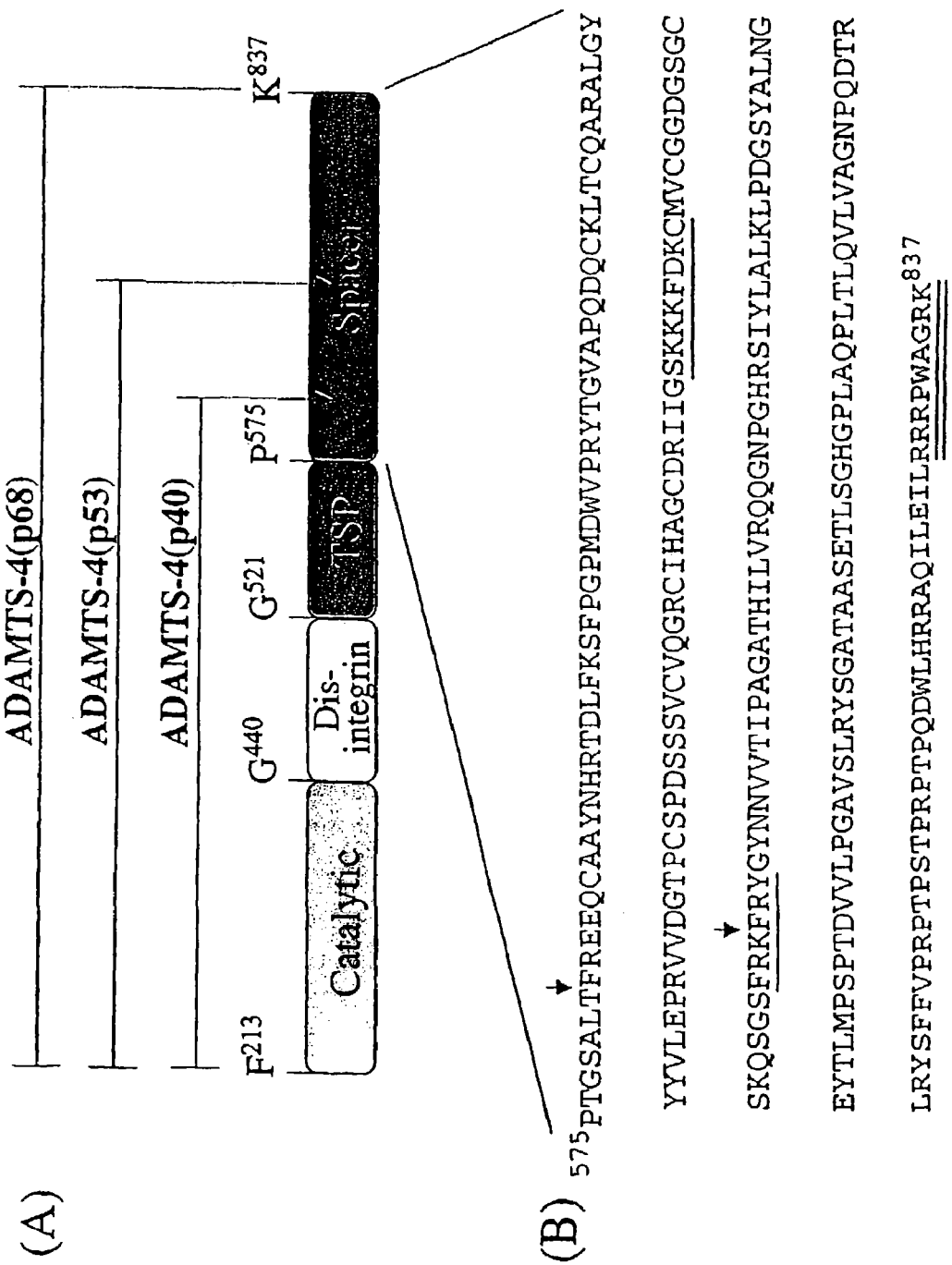
FIG. 1 is a schematic showing the auto-digested isoforms of ADAMTS4 (panel A) and the cleavage sites (panel B).

In order that the present invention may be more readily understood, certain terms are first defined. Additional definitions are set forth throughout the detailed description.

The term "aggrecanase activity" refers to at least one cellular process interrupted or initiated by an aggrecanase enzyme binding to aggrecan. Generally, aggrecanase activity refers to proteolytic cleavage of aggrecan at glu373-ala374. Aggrecanase activities include, but are not limited to, binding of aggrecanase to aggrecan and cleavage of aggrecan by aggrecanase. Aggrecanase activity can also include a biological response resulting from the binding to or cleavage of aggrecan by the modified aggrecanases of the present invention.

The term "modified aggrecanase," as used herein, refers to an aggrecanase that is altered by substitution, insertion, deletion, or modification of at least one amino acid comparing to the native aggrecanase. Modified aggrecanases of the present invention may have greater stability than the corresponding native aggrecanase molecule. Modified aggrecanases of the invention can also be expressed at higher levels both in vivo and in vitro than the corresponding native aggrecanase proteins. A modified aggrecanase is "biologically active" if it retains at least one aggrecanase activity defined in the prior paragraph. Modified aggrecanases may contain multiple alterations, such as amino acid substitutions, modifications, insertions, and deletions in different parts of the protein.

The term "stability," as used herein, generally refers to a decrease in the rate of degradation of a protein, thereby increasing its half-life, solubility and/or expression levels. Several factors affect protein stability in vitro and in vivo, for example, pH, salt concentration, temperature, protein degradation, for example by proteases, metal ions, autocatalysis of proteins, hydrophobicity etc. Conditions that make a protein more stable generally include conditions that keep the protein in a folded conformation for longer than normal, thereby preserving its biological activity for a longer period of time. An increase in stability of a protein generally increases its half-life and expression levels, thereby making it possible to purify the protein in large amounts for therapeutic purposes and for development of inhibitors.

Various aspects of the invention are described in further detail in the following subsections. The patent and scientific literature referred to herein establishes knowledge that is available to those of skill in the art. The issued U.S. patents, allowed applications, published applications (U.S. and foreign) and references, including GenBank database sequences, that are cited herein are hereby incorporated by reference to the same extent as if each was specifically and individually indicated to be incorporated by reference.

II. Modified ADAMTS4 (mTS4) Molecules and Their Utilities

The human ADAMTS4 gene, located at loci 1q21-q23 of human chromosome 1, encodes a pro-protein of 837 amino acids (SEQ ID NO:1). The protein contains an N-terminal pro-peptide (amino acid residue 1-212), a metalloproteinase catalytic domain (amino acid residue 213-436), a disintegrin-like domain (amino acid residue 437-519), a TSP-1 motif (amino acid residue 520-576), a cysteine rich domain (amino acid residue 577-685), and a spacer (amino acid residue 686-837). Unlike other proteins in the ADAMTS family, ADAMTS4 protein completely lacks a C-terminal TSP-1 motif.

The N-terminal pro-peptide of ADAMTS4 pro-protein can be cleaved by furin or related pro-protein convertase(s) within the trans-Golgi, resulting in secretion of mature enzyme lacking the pro-peptide region. The furin-processed ADAMTS4 is enzymatically active and is normally referred to as the "full-length" ADAMTS4 enzyme.

ADAMTS4 is responsible for the degradation of aggrecan, a major proteoglycan of cartilage, and of brevican, a brain-specific extracellular matrix protein. The degradation of aggrecan and brevican by ADAMTS4 suggests key roles for this enzyme in arthritic disease, in the function of the central nervous system, and potentially in the progression of glioma.

The inhibition of ADAMTS4 enzyme activity may prevent the loss of aggrecan and ameliorate cartilage degradation associated with osteoarthritis. However, efforts to develop ADAMTS4 inhibitors have been hampered by the fact that it is difficult to isolate and purify ADAMTS4 protein in large amounts due to the generally low expression levels and poor stability of the enzyme. Accordingly, there is a need to identify novel forms of ADAMTS4 and further develop ways to isolate and purify ADAMTS4 protein in large amounts in order to investigate the role of ADAMTS4 in disease states and also to develop therapies and compositions to treat diseases involving aggrecan cleavage. Modified ADAMTS4 molecules may be biologically active for the cleavage of aggrecan and can be expressed at levels higher than that of their full-length counterparts. They can be used to screen inhibitors to ADAMTS4 and other aggrecanase and to develop antibodies to ADAMTS4. The more stable mTS4 molecules also allow better biochemical and biophysical characterization of the ADAMTS4 protein though enzyme kinetic and crystallographic studies.

As used hereinafter, the modified ADAMTS4 (mTS4) molecules of the present invention include both isolated polypeptides and isolated polynucleotides.

Isolated Polypeptides

One aspect of the invention pertains to isolated mTS4 proteins. In one embodiment, the mTS4 proteins have an aggrecanase activity and can be used to screen inhibitors for aggrecanase. In another embodiment, the mTS4 proteins are used to develop antibodies to aggrecanase. Modified ADAMTS4 proteins may be produced using standard molecular biology and cell biology techniques. Modified ADAMTS4 proteins having aggrecanase activity can be identified by screening combinatorial libraries of ADAMTS4 fragments. Libraries of fragments of ADAMTS4 coding sequence can be used to generate a variegated population of ADAMTS4 fragments for screening and subsequent selection of modified ADAMTS4. In one embodiment, a library of coding sequence fragments can be generated by treating a double-stranded PCR fragment of ADAMTS4 coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, an expression library can be derived which encodes N-terminal, C-terminal and internal fragments of various sizes of the ADAMTS4 protein.

Several techniques are known in the art for screening gene products of combinatorial libraries made by truncation, and for screening cDNA libraries for gene products having a selected property. The most widely used techniques, which are amenable to high-throughput analysis for screening large gene libraries, typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify mTS4 mutants (DeLagrave et al., Protein Engineering, 6:327–331, 1993).

Portions of the ADAMTS4 protein having less than about 100 amino acids, and generally less than about 50 amino acids, may also be generated by synthetic means, using techniques well-known to those of ordinary skill in the art. For example, such polypeptides may be synthesized using any of the commercially available solid-phase techniques, such as the Merrifield solid-phase synthesis method, where amino acids are sequentially added to a growing amino acid chain.

The invention also provides mTS4 fusion protein. An mTS4 fusion protein contains an ADAMTS4-related polypeptide and a non-ADAMTS4 polypeptide fused in-frame to each other. The ADAMTS4-related polypeptide corresponds to all or a portion of the modified ADAMTS4 protein or its variant.

A peptide linker sequence may be employed to separate the ADAMTS4-related polypeptide from non-ADAMTS4 polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that can interact with functional epitopes on the ADAMTS4-related polypeptide and non-ADAMTS4 polypeptide; and (3) the lack of hydrophobic or charged residues that might react with the polypeptide functional epitopes. Preferred peptide linker sequences contain gly, asn and ser residues. Other near neutral amino acids, such as thr and ala, may also be used in the linker sequence. Amino acid sequences which may be usefully employed as linkers are well known in the art. The linker sequence may generally be from 1 to about 50 amino acids in length. Linker sequences are not required when the ADAMTS4-related polypeptide and non-ADAMTS4 polypeptide have non-essential N-terminal amino acid regions that can be used to separate the functional domains and prevent steric interference.

The mTS4 protein may contain a peptide tag to facilitate the identification and/or purification of the mTS4 protein. The peptide tags are short pieces of well-defined peptides (e.g., Poly-His, Flag-epitope, strep-tag, c-myc epitope, HA-tag) or small proteins (bacterial glutathione s-transferase (GST), maltose binding protein (MBP), thioredoxin, β-galactosidase, VSV-glycoprotein etc.). The tag sequence may be placed anywhere in the protein sequence. Preferably, the tag sequence is placed at the C-terminal of the protein or is inserted between two domain structures of the protein. The tag sequences are often cloned along with the target gene and are expressed as part of the fusion proteins. Generally, antibodies to these fusion-tags are already available to monitor fusion protein expression and purification. Therefore, fusion-tags serve as universal tags much like secondary antibodies. Many tags have their own characteristics. Poly-His-fusion proteins (6×His) can bind to Nickel-Sepharose or Nickel-HRP. GST-fusion proteins can bind to glutathione-Sepharose. Therefore, a high degree of purification of fusion protein can be achieved in just one affinity purification step. Purity of fusion proteins can be followed by Tag-antibodies. Very often, fusion proteins are directly injected into animals to generate antibodies. Some fusion tags can be removed later by treatment with enzymes to generate tag-free recombinant proteins.

Preferably, an mTS4 fusion protein of the present invention is produced by standard recombinant DNA techniques. The fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence. Moreover, many expression vectors are commercially available that already encode a fusion moiety (e.g., a GST polypeptide). An ADAMTS4-related polynucleotide can be cloned into such an expression vector such that the fusion moiety is linked in-frame to the ADAMTS4-related polypeptide.

A signal sequence can be used to facilitate secretion and isolation of mTS4 or mTS4 fusion proteins of the present invention. Signal sequences are typically characterized by a core of hydrophobic amino acids that are generally cleaved from the mature protein during secretion in one or more cleavage events. Such signal peptides contain processing sites that allow cleavage of the signal sequence from the mature proteins as they pass through the secretory pathway.

The invention further includes fragments and variants of the modified ADAMTS4 proteins. It is known, for example, that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine, arginine and histidine; amino acids with acidic side chains, such as aspartic acid and glutamic acid; amino acids with uncharged polar side chains, such as asparagine, glutamine, serine, threonine, and tyrosine; and amino acids with non-polar side chains, such as alanine, glycine, valine, leucine, isoleucine, proline, phenylalanine, methionine, tryptophan and cysteine. Thus, these modifications and deletions of the original mTS4 protein may be employed as biologically-active substitutes for the original mTS4 protein. It can be readily determined whether a given variant of an mTS4 or mTS4 fusion protein maintains the biological activity of the original protein by subjecting both proteins (the original protein and the variant) to the biological activity assays described in the examples.

Substitution of like amino acids can also be made on the basis of hydrophilicity, particularly where the biological functional equivalent polypeptide or polypeptide fragment is intended for use in immunological embodiments. U.S. Pat. No. 4,554,101, incorporated hereinafter by reference, states that the greatest local average hydrophilicity of a polypeptide, as governed by the hydrophilicity of its adjacent amino acids, correlates with its immunogenicity and antigenicity, i.e., with a biological property of the polypeptide. It is understood that an amino acid can be substituted for another having a similar hydrophilicity value and still obtain a biologically equivalent, and, in particular, an immunologically equivalent polypeptide.

In one embodiment, active site mutations are introduced into an mTS4 molecule to intentionally block the catalytic activity of the enzyme. This approach is especially useful for the purposes of crystallization and structural determination of mTS4 protein and subsequently to identify and develop inhibitors of mTS4. Increased stability of active-site mutant of mTS4 of the present invention makes it possible to purify and isolate large amounts of mTS4 molecules for subsequent use in the development of inhibitors for treatment of diseases. For example, the E362Q mutation makes the mTS4 biologically inactive, thereby enabling purification of the inactive protein in large amounts for crystallization.

Desired amino acid substitutions (whether conservative or nonconservative) can be determined by those skilled in the art at the time such substitutions are desired. For example, amino acid substitutions can be used to identify important amino acid residues of the proteins or polypeptides of the invention or to increase or decrease the activity of the aggrecanases of the invention described. Exemplary amino acid substitutions are set forth in Table 1.

TABLE 1

Amino Acid Substitutions

| Original Residues | Exemplary Substitutions | More Conservative Substitutions |
|---|---|---|
| ala (A) | val, leu, ile | val |
| arg (R) | lys, gln, asn | lys |
| asn (N) | gln | gln |
| asp (D) | glu | glu |
| cys (C) | ser, ala | ser |
| gln (Q) | asn | asn |
| his (H) | asn, gln, lys, arg | arg |
| ile (I) | leu, val, met, ala, phe, norleucine | leu |
| leu (L) | norleucine, ile, val, met, ala, phe | ile |
| lys (K) | arg, 1, 4 diamino-butyric acid, gln, asn | arg |
| met (M) | leu, phe, ile | leu |
| phe (F) | leu, val, ile, ala, tyr | leu |
| pro (P) | ala | gly |
| ser (S) | thr, ala, cys | thr |
| thr (T) | ser | ser |
| trp (W) | tyr, phe | tyr |
| tyr (Y) | trp, phe, thr, ser | phe |
| val (V) | ile, met, leu, phe, ala, norleucine | leu |

In certain embodiments, conservative amino acid substitutions also encompass non-naturally-occurring amino acid residues which are typically incorporated by chemical peptide synthesis rather than by synthesis in biological systems.

Other specific mutations of the sequences of aggrecanase proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of aggrecanase-related protein will also result in production of a non-glycosylated protein, even if the glycosylation sites are left unmodified.

Isolated Polynucleotides

Another aspect of the invention pertains to isolated polynucleotides that encode an mTS4 protein. A polynucleotide molecule comprising the nucleotide sequence of an mTS4 molecule can be prepared using standard molecular biology techniques and the sequence information provided herein as well as sequence information known in the art. The native or modified ADAMTS4 gene sequences can be amplified using cDNA, mRNA or alternatively, genomic DNA as a template, and appropriate oligonucleotide primers according to standard PCR amplification techniques. The polynucleotide so amplified can be cloned into an appropriate vector and characterized by DNA sequence analysis. Furthermore, oligonucleotides corresponding to the native or modified ADAMTS4 sequences can be prepared by standard synthetic techniques, e.g., using an automated DNA synthesizer. In one embodiment, the mTS4 sequence may include a modified Kozak sequence to improve translation efficiency.

It will be appreciated by those of ordinary skill in the art that, as a result of the degeneracy of the genetic code, there are many polynucleotide variants that encode the same polypeptide. Some of these polynucleotide variants bear minimal sequence homology to the original polynucleotide. Nonetheless, polynucleotides that vary due to differences in codon usage are specifically contemplated by the present invention.

The invention also pertains to polynucleotides encoding variants of the mTS4 proteins. An isolated polynucleotide molecule encoding a variant of an mTS4 protein can be created by introducing one or more nucleotide substitutions, additions or deletions into the nucleotide sequence of the polynucleotide, such that one or more amino acid substitutions, additions or deletions are introduced into the encoded protein. Such techniques are well-known in the art. Mutations can be introduced into an mTS4 protein by standard techniques, such as site-directed mutagenesis and PCR-mediated mutagenesis. Alternatively, mutations can be introduced randomly along all or part of a coding sequence of an mTS4 protein, such as by saturation mutagenesis, and the resultant mutants can be screened for biological activity to identify mutants that are capable of inhibiting wild-type protein activity (the dominant negative mutant). Following mutagenesis, the encoded protein can be expressed recombinantly and the activity of the protein can be determined.

A polynucleotide may be further modified to increase stability in vivo. Possible modifications include, but are not limited to, the addition of flanking sequences at the 5' and/or 3' ends; the use of phosphorothioate or 2-o-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

III. Expression Vectors

Another aspect of the present invention includes vectors for use in a method of expression of mTS4 proteins. Preferably, vectors of the present invention contain a DNA sequence described above which encodes an mTS4 or an active site mutant of an mTS4. Vectors may contain appropriate expression control sequences permitting expression of the modified ADAMTS4 protein of the invention.

In one embodiment, the vector of the invention is an expression vector comprising a polynucleotide encoding an mTS4 in a form suitable for expression of the polynucleotide in a host cell. The vectors generally have one or more regulatory sequences, selected on the basis of the host cells to be used for expression, which is operatively linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by polynucleotides as described herein The expression vectors of the invention can be designed for expression of the mTS4 in prokaryotic or eukaryotic cells. For example, the mTS4 can be expressed in bacterial cells such as E. coli, insect cells (using baculovirus expression vectors), yeast cells or mammalian cells. Alternatively, the expression vector can be transcribed and translated in vitro, for example, using T7 promoter regulatory sequences and T7 polymerase.

The expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Piscataway, N.J.), pMAL (New England Biolabs, Beverly, Mass.) and pRITS (Pharmacia, Piscataway, N.J.) which fuse GST, MBP, or protein A, respectively, to the target recombinant protein.

Examples of suitable inducible non-fusion E. coli expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase Is supplied by host strains BL21(DE3) or HSLE174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein. Another strategy is to alter the polynucleotide sequence of the polynucleotide to be inserted into an expression vector so that the individual codons for each amino acid are those preferentially utilized in E. coli. Such alteration of polynucleotide sequences of the invention can be carried out by standard DNA synthesis techniques.

In another embodiment, the mTS4 expression vector is a yeast expression vector. Examples of vectors for expression in yeast S. cerevisiae include pYepSec1, pMFa, pJRY88, pYES2 (Invitrogen Corporation, San Diego, Calif.), and picZ (Invitrogen Corp, San Diego, Calif.).

Alternatively, an mTS4 can be expressed in insect cells using baculovirus expression vectors. Baculovirus vectors available for expression of proteins in cultured insect cells (e.g., Sf9 cells) include the pAc series and the pVL series.

In yet another embodiment, an mTS4 is expressed in mammalian cells using a mammalian expression vector. Examples of mammalian expression vectors include pCDM8, pMT2PC and pHTop. When used in mammalian cells, the expression vector's control functions are often provided by viral regulatory elements. For example, commonly used promoters are derived from polyoma, adenovirus 2, cytomegalovirus and Simian Virus 40. Alternatively, the expression vector's control functions may be provided by the native ADAMTS4 promoter or a tissue-specific regulatory elements.

The invention further provides gene delivery vehicles for the delivery of polynucleotides to cells, tissue, or a mammal for expression. For example, a polynucleotide sequence of the invention can be administered either locally or systemically in a gene delivery vehicle. These constructs can utilize viral or non-viral vector approaches in in vivo or ex vivo modality. Expression of such coding sequences can be induced using endogenous mammalian or heterologous promoters. Expression of the coding sequence in vivo can be either constituted or regulated. The invention includes gene delivery vehicles capable of expressing the contemplated polynucleotides. The gene delivery vehicle is preferably a viral vector and, more preferably, a retroviral, lentiviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector.

Delivery of the mTS4 constructs of the present invention into cells is not limited to the above-mentioned viral vectors. Other delivery methods and media may be employed such as, for example, nucleic acid expression vectors, polycationic condensed DNA linked or unlinked to killed adenovirus alone, liposomes, ligand linked DNA, eukaryotic cell delivery vehicles, deposition of photopolymerized hydrogel materials, handheld gene transfer particle gun, ionizing radiation, nucleic charge neutralization or fusion with cell membranes. Particle mediated gene transfer may be employed. For example, the sequence can be inserted into conventional vectors that contain conventional control sequences for high-level expression, and then be incubated with synthetic gene transfer molecules such as polymeric DNA-binding cations like polylysine, protamine, and albumin, linked to cell targeting ligands such as asialoorosomucoid, insulin, galactose, lactose or transferrin. Naked DNA may also be employed. The uptake efficiency of the naked DNA may be improved using biodegradable latex beads.

IV. Production of Aggrecanase Proteins

Modified ADAMTS4 protein of the invention may be produced by culturing a cell transformed or infected with an expression vector described above. The protein may be purified with standard protein purification techniques. Purified mTS4 proteins are substantially free from other proteinaceous materials with which they are co-produced, as well as from other contaminants. A recovered purified protein is contemplated to exhibit proteolytic aggrecanase activity by cleaving aggrecan. Thus, proteins of the invention may be further characterized by their ability to demonstrate aggrecan proteolytic activity in an assay which determines the presence of an aggrecan-degrading molecule. These assays or the development thereof is within the knowledge of one skilled in the art. Such assays may involve contacting an aggrecan substrate with the aggrecanase molecule and monitoring the production of aggrecan fragments (See, for example, Hughes et al., Biochem. J. 305:799–804, 1995; Mercuri et al, J. Bio. Chem. 274:32387–32395, 1999).

Suitable cells or cell lines may be mammalian cells, such as Chinese hamster ovary cells (CHO). The selection of suitable mammalian host cells and methods for transformation, culture, amplification, screening, product production, and purification are known in the art. Another suitable mammalian cell line, which is described in the accompanying examples, is the monkey COS-1 cell line. The mammalian cell line CV-1 may also be suitable.

Bacterial cells may also be suitable hosts. For example, the various strains of *E. coli* (e.g., HB101, MC1061) are well-known as host cells in the field of biotechnology. Various strains of *B. subtilis, Pseudomonas*, other bacilli and the like may also be employed in this method. For expression of mTS4 proteins of the invention in bacterial cells, DNA encoding the pro-peptide of an aggrecanase is generally not necessary.

Many strains of yeast cells known to those skilled in the art may also be available as host cells for expression of polypeptides of the present invention. Additionally, where desired, insect cells may be utilized as host cells in the method of the present invention. See, e.g. Miller et al., Genetic Engineering, 8:277–298 (Plenum Press 1986) and references cited therein.

Modified ADAMTS4 proteins produced in host cells can be isolated from the host cells by an appropriate purification scheme using standard protein purification techniques. Standard purification methods include electrophoretic, molecular, immunological and chromatographic techniques, including ion exchange, hydrophobic, affinity, and reverse-phase HPLC chromatography, and chromatofocusing. For example, the mTS4 protein may be purified using an anti-mTS4 antibody column. Ultrafiltration and diafiltration techniques, in conjunction with protein concentration, are also useful. The degree of purification necessary will vary depending on the use of the modified ADAMTS4 protein. In some instances no purification will be necessary.

V. Generation of Antibodies

In accordance with another aspect of the present invention, antibodies specific to mTS4 ADAMTS4, or other ADAMTS4-related proteins are prepared Anti-mTS4 antibodies include both antibodies that block aggrecanase activity of mTS4 and antibodies that do not. Anti-mTS4 antibodies also include "neoepitope antibodies" which refer to antibodies that specifically recognizes a new N- or C-terminal amino acid sequence exposed by proteolytic cleavage of ADAMTS4 or mTS4, but does not bind to such an epitope on the original (uncleaved) molecule. The anti-mTS4 antibodies may be useful for detection and/or purification of aggrecanase or related proteins, or for inhibiting or preventing the effects of aggrecanase.

An mTS4 protein, or an antigenic fragment of the mTS4 protein can be used as an immunogen. The antigenic peptide of the mTS4 protein comprises at least 8 amino acid residues of the mTS4 amino acid sequence, and encompasses an epitope of the mTS4 protein such that an antibody raised against the peptide forms a specific immune complex with the mTS4 protein. Preferably, the antigenic peptide comprises at least 8 amino acid residues, more preferably at least 12 amino acid residues, even more preferably at least 16 amino acid residues, and most preferably at least 20 amino acid residues.

An mTS4 immunogen (e.g., the mTS4 protein, a fragment thereof, or an mTS4 fusion protein) typically is used to prepare antibodies by immunizing a suitable subject, (e.g., rabbit, goat, mouse or other mammal) with the immunogen. An appropriate immunogenic preparation can contain, for example, recombinantly expressed mTS4 immunogen or a chemically synthesized mTS4 immunogen. The preparation can further include an adjuvant, such as Freund's complete or incomplete adjuvant, or similar immunostimulatory agent. Immunization of a suitable subject with the immunogenic preparation induces an anti-mTS4 antibody response. Techniques for preparing, isolating and using monoclonal and polyclonal anti-mTS4 antibodies are well known in the art.

Accordingly, another aspect of the invention pertains to monoclonal or polyclonal anti-mTS4 antibodies. The invention provides polyclonal and monoclonal antibodies that bind to mTS4 protein.

An anti-mTS4 antibody can be used to isolate the mTS4 protein or mTS4-related protein by standard techniques, such as affinity chromatography or immunoprecipitation. An anti-mTS4 antibody can facilitate the purification of an mTS4 protein or mTS4-related proteins, such as full-length ADAMTS4 protein, mTS4-fusion protein, or variants and mutants thereof, from cells. Moreover, an anti-mTS4 antibody can be used to detect an mTS4 protein or an mTS4-related protein in order to evaluate the abundance and pattern of expression of the protein. Anti-mTS4 antibodies that cross-react with ADAMTS4 protein can be used diagnostically to monitor ADAMTS4 protein levels in tissue as part of a clinical testing procedure to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$ and $^{3}H$.

Anti-mTS4 antibodies that cross-react with ADAMTS4 protein are also useful for targeting a therapeutic to a cell or tissue having elevated ADAMTS4 expression. For example, a therapeutic such as a small molecule ADAMTS4 antagonist can be linked to the anti-modified ADAMTS4 antibody in order to target the therapeutic to the cell or tissue having elevated ADAMTS4 expression.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues.

Where a therapeutic agent is more potent when free from the antibody portion of the immunoconjugates of the present invention, it may be desirable to use a linker group that is cleavable during or upon internalization into a cell. A number of different cleavable linker groups have been described. The mechanisms for the intracellular release of an agent from these linker groups include cleavage by reduction of a disulfide bond, by irradiation of a photolabile bond, by hydrolysis of derivatized amino acid side chains, by serum complement-mediated hydrolysis, and acid-catalyzed hydrolysis.

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

VI. Development of Inhibitors

The mTS4 protein of the present invention may be used for the development of inhibitors to ADAMTS4 and other aggrecanases. The aggrecanase inhibitors may be used in the treatment for aggrecanase-related diseases. For example, increased breakdown of aggrecan is associated with the development of osteoarthritis. Two cartilage aggrecanases, ADAMTS4 and ADAMTS5, are primarily responsible for the catabolism and loss of aggrecan from articular cartilage in the early stages of arthritic joint diseases that precede overt collagen catabolism and disruption of the tissue integrity (Caterson et al., Matrix Biol. 19:333–44, 2000). Inhibiting ADAMTS4 and ADAMTS5 activity is therefore a potential treatment for osteoarthritis.

Various efforts have been made to develop inhibitors to aggrecanase. The N-terminal inhibitory domain of endogenous tissue inhibitors of metalloproteases 3 (TIMP-3) is a strong inhibitor of human ADAMTS4 and ADAMTS5, with K(i) values in the subnanomolar range (Kashiwagi et al. J. Biol. Chem. 276:12501–12504, 2001). Further studies revealed that other TIMPs may also inhibit ADAMTS4 activity. For example, TIMP-3 inhibited ADAMTS4 activity most efficiently with an IC(50) value of 7.9 nM, which was at least 44-fold lower than that of TIMP-1 (350 nM) and TIMP-2 (420 nM) and at least 250-fold less than that of TIMP-4 (2 uM for 35% inhibition) (Hashimoto et al., FEBS Lett. 494:192–195, 2001).

There is evidence that cyclosporin A can inhibit IL-1-induced aggrecanase-mediated proteoglycan catabolism in articular cartilage explants (Little et al., Arthritis Rheum. 46:124–129, 2002). Suppression of ADAMTS1 activity was also accomplished with a specific monoclonal antibody and some metalloprotease inhibitors, including TIMP-2 and 3 (Rodriguez-Manzaneque et al., Biochem. Biophys. Res. Commun. 293:501–508, 2002).

Modified ADAMTS4 proteins with increased stability and expression levels make it possible to generate aggrecanase molecules in large amounts in order to develop inhibitors to aggrecanases. Accordingly, the invention also provides methods (also referred to herein as "screening assays") for identifying aggrecanase inhibitors. Such methods typically comprise a reaction between the mTS4 protein and one or more test components. The other components may be either the test compound itself, or a combination of the test compound and a binding partner of the mTS4 protein.

One aspect of the present invention provides methods for screening compounds that interfere with binding of an mTS4 protein and its binding partner, e.g. aggrecan and brevican. In one embodiment, a scintillation proximity assay is used. In this assay, the mTS4 protein is labeled with an isotope such as $^{125}I$. The binding partner is labeled with a scintillant, which emits light when proximal to radioactive decay (i.e., when the mTS4 protein is bound to its binding partner). A reduction in light emission will indicate that a compound has interfered with the binding of the two proteins.

Alternatively a fluorescence energy transfer (FRET) assay could be used. In an FRET assay, a fluorescence energy donor is comprised of one protein (e.g., an mTS4 protein and a fluorescence energy acceptor is comprised on a second protein (e.g., a binding partner of the mTS4 protein). If the absorption spectrum of the acceptor molecule overlaps with the emission spectrum of the donor fluorophore, the fluorescent light emitted by the donor is absorbed by the acceptor. The donor molecule can be a fluorescent residue on the protein (e.g., intrinsic fluorescence such as a tryptophan or tyrosine residue), or a fluorophore which is covalently conjugated to the protein (e.g., fluorescein isothiocyanate, FITC). An appropriate donor molecule is then selected with the above acceptor/donor spectral requirements in mind.

Thus, in this example, an mTS4 protein is labeled with a fluorescent molecule (i.e., a donor fluorophore) and its binding partner is labeled with a quenching molecule (i.e., an acceptor). When the mTS4 protein and its binding partner are bound, fluorescence emission will be quenched or reduced relative to the mTS4 protein alone. Similarly, a compound which can dissociate the interaction of the mTS4 protein-partner complex will result in an increase in fluorescence emission. The increase in fluoresce emission indicates that the compound has interfered with the binding of the mTS4 protein to its binding partner.

In another embodiment, a FRET peptide that constitute an aggrecanase-susceptible protein sequence is used substrates of aggrecanase. When aggrecanase cleaves the peptide, the fluor is released from the quencher on the same peptide and fluorescence results. Inhibition of this generation of fluorescence by compounds is judged a positive result.

Another assay to detect binding or dissociation of two proteins is fluorescence polarization or anisotropy. In this assay, the investigated protein (e.g., mTS4 protein) is labeled with a fluorophore with an appropriate fluorescence lifetime. The protein sample is then excited with vertically polarized light. The value of anisotropy is then calculated by determining the intensity of the horizontally and vertically polarized emission light. Next, the labeled protein (the mTS4 protein) is mixed with an mTS4 protein binding partner and the anisotropy is measured again. Because fluorescence anisotropy intensity is related to the rotational freedom of the labeled protein, the more rapidly a protein rotates in solution, the smaller the anisotropy value. Thus, if the labeled mTS4 protein is part of a complex (e.g., mTS4 protein-partner), the mTS4 protein rotates more slowly in solution (relative to free, unbound mTS4 protein) and the anisotropy intensity increases. Subsequently, a compound which can dissociate the interaction of the mTS4 protein-partner complex will result in a decrease in anisotropy (i.e., the labeled mTS4 protein rotates more rapidly), which indicates the compound has interfered with the binding of mTS4 protein to its binding partner.

A more traditional assay would involve labeling the mTS4 protein-binding partner with an isotope such as $^{125}$I, incubating with the mTS4 protein, then immunoprecipitating the mTS4 protein. Compounds that increase the free mTS4 protein will decrease the precipitated counts. To avoid using radioactivity, the mTS4 protein-binding partner could be labeled with an enzyme-conjugated antibody instead.

Alternatively, the mTS4 protein-binding partner could be immobilized on the surface of an assay plate and the mTS4 protein could be labeled with a radioactive tag. A rise in the number of counts would identify compounds that had interfered with binding of the mTS4 protein and its binding partner.

Evaluation of binding interactions may further be performed using Biacore technology, wherein the mTS4 protein or its binding partner is bound to a micro chip, either directly by chemical modification or tethered via antibody-epitope association (e.g., antibody to the mTS4 protein), antibody directed to an epitope tag (e.g., His tagged) or fusion protein (e.g., GST). A second protein or proteins is/are then applied via flow over the "chip" and the change in signal is detected. Finally, test compounds are applied via flow over the "chip" and the change in signal is detected.

The test compounds of the present invention are generally either small molecules or biomolecules. Small molecules include, but are not limited to, inorganic molecules and small organic molecules. Biomolecules include, but are not limited to, naturally-occurring and synthetic compounds that have a bioactivity in mammals, such as lipids, steroids, polypeptides, polysaccharides, and polynucleotides. In one preferred embodiment, the test compound is a small molecule. In another preferred embodiment, the test compound is a biomolecule.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds. As used herein, the term "binding partner" refers to a molecule which serves as either a substrate for an mTS4 protein, or alternatively, as a ligand having binding affinity to the mTS4 protein.

In another embodiment, the assay involves determining the level of aggrecanase expression in a cell or a tissue before and after exposing the cell/tissue to a test compound. The aggrecanase expression may be determined on the protein level or RNA level using standard techniques such as ELISA, western blot, Northern blot, RT-PCR, and real-time PCR.

The invention provides methods of conducting high-throughput screening for test compounds capable of inhibiting activity or expression of an mTS4 protein of the present invention. In one embodiment, the method of high-throughput screening involves combining test compounds and the mTS4 protein and detecting the effect of the test compound on the mTS4 protein.

A variety of high-throughput functional assays well-known in the art may be used in combination to screen and/or study the reactivity of different types of activating test compounds. Since the coupling system is often difficult to predict, a number of assays may need to be configured to detect a wide range of coupling mechanisms. A variety of fluorescence-based techniques are well-known in the art and are capable of high-throughput and ultra high throughput screening for activity, including but not limited to BRET® or FRET® (both by Packard Instrument Co., Meriden, Conn.). The ability to screen a large volume and a variety of test compounds with great sensitivity permits analysis of the therapeutic targets of the invention to further provide potential inhibitors of aggrecanase.

By combining test compounds with modified ADAMTS4 proteins of the invention and determining the binding activity between them, diagnostic analysis can be performed to elucidate the coupling systems. Generic assays using cytosensor microphysiometer may also be used to measure metabolic activation, while changes in calcium mobilization can be detected by using the fluorescence-based techniques such as FLIPR® (Molecular Devices Corp, Sunnyvale, Calif.). In addition, the presence of apoptotic cells may be determined by TUNEL assay, which utilizes flow cytometry to detect free 3-OH termini resulting from cleavage of genomic DNA during apoptosis. As mentioned above, a variety of functional assays well-known in the art may be used in combination to screen and/or study the reactivity of different types of activating test compounds. Preferably, the high-throughput screening assay of the present invention utilizes label-free plasmon resonance technology as provided by BIACORE® systems (Biacore International AB, Uppsala, Sweden). Plasmon free resonance occurs when surface plasmon waves are excited at a metal/liquid interface. By reflecting directed light from the surface as a result of contact with a sample, the surface plasmon resonance causes a change in the refractive index at the surface layer. The refractive index change for a given change of mass concentration at the surface layer is similar for many bioactive agents (including proteins, peptides, lipids and polynucleotides), and since the BIACORE® sensor surface can be functionalized to bind a variety of these bioactive agents, detection of a wide selection of test compounds can thus be accomplished.

A high-throughput screening assay for inhibitors of aggrecan cleavage using luminescent oxygen channeling was recently developed by Peppard et al. (Peppard et al., J. Biomol. Screen. 8:149–156, 2003). The assay utilizes the AlphaScreen™ technology. In this technology, a "donor" bead and an "acceptor" bead are brought into proximity by a specific biological interaction and are stimulated with laser light generate a signal through luminescent oxygen tunneling. The screening assay uses specific antibodies to the carbohydrate side chains of aggrecan to create a scaffold whereby aggrecan could form a cross-link between donor and acceptor beads, thus bringing the beads into proximity to produce a signal upon illumination with laser light. Digested aggrecan will fail to form such a cross-link and generate no signal. The inhibitors of the digestion can be detected as a restoration of signal.

An assay for identification and development of aggrecanase inhibitors may also involve, for example, contacting a mixture of aggrecan and an inhibitor with an mTS4 protein followed by measurement of the degree of aggrecanase activity inhibition; for instance, by detection and measurement of aggrecan fragments produced by cleavage at an aggrecanase susceptible site. Inhibitors may be proteins, peptides, antibodies, or chemical compounds. In one embodiment, inhibitors are peptide molecules that bind an active site on aggrecanase molecules. For example, active site mutants of mTS4 molecules can be used for the development of peptide inhibitors.

VII. Disease Treatment and Diagnosis

Inhibitors of aggrecanase and antibodies that block aggrecanase activity may be used in the treatment of aggrecanase-related diseases. Various diseases that are contemplated as being treatable by using inhibitors of aggrecanases or antibodies of the present invention include, but are not limited to, osteoarthritis, glioma, cancer, inflammatory joint disease, rheumatoid arthritis, septic arthritis, periodontal diseases, corneal ulceration, proteinuria, coronary thrombosis from atherosclerotic plaque rupture, aneurysmal aortic disease, inflammatory bowel disease, Crohn's disease, emphysema, acute respiratory distress syndrome, asthma, chronic obstructive pulmonary disease, Alzheimer's disease, brain and hematopoietic malignancies, osteoporosis, Parkinson's disease, migraine, depression, peripheral neuropathy, Huntington's disease, multiple sclerosis, ocular angiogenesis, macular degeneration, aortic aneurysm, myocardial infarction, autoimmune disorders, degenerative cartilage loss following traumatic joint injury, head trauma, dystrophobic epidermolysis bullosa, spinal cord injury, acute and chronic neurodegenerative diseases, osteopenias, tempero mandibular joint disease, demyelating diseases of the nervous system, organ transplant toxicity and rejection, cachexia, allergy, tissue ulcerations, restenosis, and other diseases characterized by altered aggrecanase activity or altered aggrecanase level.

Inhibitors and antibodies of the present invention that inhibit activity of aggrecanases and/or compounds that lower expression of aggrecanases may be used in the treatment of any disease in a mammal that involves degradation of the extracellular matrix. An effective amount of an anti-aggrecanase antibody, or an aggrecanase inhibitor, or both, can be used for treatment of diseases, such as osteoarthritis, or other diseases disclosed which are characterized by degradation of matrix proteins, such as aggrecan, by aggrecanases and aggrecanase-related proteins.

VIII. Pharmaceutical Compositions

Another aspect of the present invention provides a pharmaceutical composition comprising (1) an mTS4 inhibitor or an anti-mTS4 antibody and (2) a pharmaceutically acceptable carrier. The composition of the present invention may be used in the treatment of diseases characterized by the degradation of aggrecan by an aggrecanase enzyme or a protein with aggrecanase-like activity.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary agents can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, such as sodium chloride, sugars, polyalcohols (e.g., manitol, sorbitol, etc.) in the composition. Prolonged absorption of the injectable compositions can be brought about by including in the composition an agent which delays absorption, for example, aluminum monostearate and gelatin.

Sterile injectable solutions can be prepared by incorporating the aggrecanase inhibitor or anti-aggrecanase antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser that contains a suitable propellant, e.g., a gas such as carbon dioxide, or a nebulizer.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

IX. Administration

The present invention includes methods for treating patients suffering from conditions characterized by a degradation of aggrecan. These methods entail administering, to a patient needing such treatment, an effective amount of a composition comprising an aggrecanase inhibitor or an anti-aggrecanase antibody that inhibits the proteolytic activity. It is contemplated that aggrecanase inhibitors of the present invention may function either by inhibiting aggrecanase activity or simply by regulating levels of aggrecanases in a disease state.

Anti-aggrecanase antibodies and aggrecanase inhibitors of the present invention are useful to diagnose or treat various medical disorders in humans or animals. In one embodiment, the antibodies of the invention can be used to inhibit or reduce at least one activity associated with an aggrecanase protein, relative to an aggrecanase protein not bound by the same antibody. Generally, compositions of the present invention are administered to a patient so that antibodies or their binding fragments are administered at a dose ranging from about 1 µg/kg to about 100 mg/kg, about 1 µg/kg to about 10 mg/kg, about 1 µg/kg to about 1 mg/kg, about 10 µg/kg to about 1 mg/kg, about 10 µg/kg to about 100 µg/kg, or about 100 µg to about 1 mg/kg. Antibodies are administered as a bolus dose, to maximize the interval of time that the antibodies can circulate in the patient's body following their administration to the patient. Continuous infusion may also be used after an initial bolus dose.

In another embodiment, the invention is directed to administration of inhibitors of aggrecanases, such as biomolecules and chemical compounds. The effective amount of an inhibitor is a dosage which is useful for reducing activity of aggrecanases to achieve a desired biological outcome. Generally, appropriate therapeutic dosages for administering an inhibitor may range, for example, from about 1 ng/kg to about 100 mg/kg, about 1 ng/kg to about 1 µg/kg, about 1 µg/kg to about 1 mg/kg, or about 1 mg/kg to about 100 mg/kg. Inhibitors can be administered in one dose, or at intervals such as once daily, once weekly, or once monthly. Dosage schedules for administration of an aggrecanase inhibitor can be adjusted based on, for example, the affinity of the inhibitor for its aggrecanase target, the half-life of the inhibitor, and the severity of the patient's condition. Generally, inhibitors are administered as a bolus dose, to maximize their circulating levels. Continuous infusions may also be used after the bolus dose.

Toxicity and therapeutic efficacy of such compounds can be determined by standard pharmaceutical procedures in cell culture or experimental animal models, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Inhibitors that exhibit large therapeutic indices are generally preferred.

The data obtained from cell culture assays and animal studies can be used in formulating a range of dosages for use in humans. The dosage of such compounds may lie within a range of circulating concentrations that exhibit an ED50 with little or no toxicity. The dosage may vary within this range depending upon the dosage form employed and the route of administration utilized. For any inhibitor used according to the present invention, a therapeutically effective dose can be estimated initially from cell culture assays. A dose may be formulated in animal models to achieve a circulating plasma concentration range that exhibits an IC50

(i.e., the concentration of the test antibody which achieves a half-maximal inhibition of symptoms) as determined by cell culture assays. Levels in plasma may be measured, for example, by high performance liquid chromatography. The effects of any particular dosage can be monitored by suitable bioassays. Examples of suitable bioassays include assays for measuring aggrecanase activity such as monitoring synovial fluid for the presence or reduction in aggrecan neoepitopes using antibody reagents such as BC-3 (Roberts et al., Arthritis Rheum. 44:2586–98, 2001) as well as assays described in Example 7, DNA replication assays, transcription-based assays, and immunological assays.

Therapeutic methods of the invention include administering an aggrecanase inhibitor composition topically, systemically, or locally as an implant or a device. The dosage regimen for the administration of composition will be determined by the attending physician based on various factors which modify the action of the aggrecanase protein, the site of pathology, the severity of disease, the patient's age, sex, and diet, the severity of any inflammation, time of administration and other clinical factors. Generally, systemic or injectable administration will be initiated at a dose which is minimally effective, and the dose will be increased over a pre-selected time course until a positive effect is observed. Subsequently, incremental increases in dosage will be made limiting to levels that produce a corresponding increase in effect, while taking into account any adverse affects that may appear. The addition of other known factors, to a final composition, may also affect the dosage.

Progress can be monitored by periodic assessment of disease progression. The progress can be monitored, for example, by X-rays, MRI or other imaging modalities, synovial fluid analysis, and/or clinical-examination.

X. Assays and Methods of Detection.

The inhibitors and antibodies of the present invention can be used in assays and methods of detection to determine the presence or absence of, or quantify aggrecanase in a sample. The inhibitors and antibodies of the present invention may be used to detect aggrecanase proteins, in vivo or in vitro. By correlating the presence or level of these proteins with a disease, one of skill in the art can diagnose the associated disease or determine its severity. Diseases that may be diagnosed by the presently disclosed inhibitors and antibodies are set forth above.

Detection methods for use with antibodies are well known in the art and include ELISA, radioimmunoassay, immunoblot, western blot, immunofluorescence, immuno-precipitation, and other comparable techniques. The antibodies may further be provided in a diagnostic kit that incorporates at least one of these techniques to detect a protein (e.g., an aggrecanase protein). Such a kit may contain other components, packaging, instructions, or other material to aid the detection of an aggrecanase protein, and instructions regarding use of the kit. When protein inhibitors, for example, peptide inhibitors, are used in such diagnostic assays, protein-protein interaction assays can be employed.

Where inhibitors are intended for diagnostic purposes, it may be desirable to modify them; for example, with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetra methyl benzidine (TMB) to a blue pigment, quantifiable with a spectrophotometer. Other suitable binding partners include biotin and avidin or streptavidin, IgG and protein A, and the numerous receptor-ligand couples known in the art.

The following examples illustrate practice of the present invention in expressing, isolating and characterizing ADAMTS4 and mTS4 proteins.

XI. EXAMPLES

Example 1

Cloning and Purification of Full-length Human ADAMTS4

Human ADAMTS4 cDNA was cloned using a PCR strategy. Two sets of oligonucleotide primers were designed to amplify overlapping portions of the 5'- and 3'-halves of the cDNA. Of the seven human multiple-tissue cDNA libraries that were used as PCR templates, only the uterus cDNA library resulted in PCR products of the appropriate size (5'-amplimer of 1294 bp (SEQ ID NO:2) and 3'-amplimer of 1421 bp (SEQ ID NO:3)). PCR-amplified fragments were digested with EcoRI and BamHI (5'-product) or BamHI and NotI (3'-product), ligated into EcoRI- and NotI-digested COS expression vector pED6-dpc2, and transformed into ElectroMAX DH10B cells (Invitrogen). Cloned PCR fragments of ADAMTS4 were sequenced and found to have three silent changes as compared with the published nucleotide sequence for ADAMTS4 cDNA (SEQ ID NO:4) (Tortorella et al., Science 284:1664–1666, 1999). These changes were C to T at base pair 466, A to G at base pair 2131, and A to G at base pair 2758 of SEQ ID NO:4. The 5'-primer set was 5'-AAATGGGCGAATTCCCACCAT-GTCCCAGACAGGCTCGCATCC-3' (SEQ ID NO:5)(this primer incorporated an 8-bp tail (AAATGGGC)(SEQ ID NO:6), an EcoRI site (GAATTC)(SEQ ID NO:7), and an optimized Kozak sequence (CCACC)(SEQ ID NO:8) upstream of the ATG start codon) and 5'-TAAGAGACAGT-GCCCATAGCCATTGT-3' (SEQ ID NO:9). The 3'-primer set was 5'-CTCCAAGCCATGCATCAGTTTGAATG-3' (SEQ ID NO:10) and 5'-GACTGACTGCGGCCGCAT-AGTGAGGTTATTTCCTGCCCGCC-3'(SEQ ID NO:11) (this primer incorporated an 8-bp tail (GACTGACT) (SEQ ID NO:12) and a NotI site (GCGGCCGC) (SEQ ID NO:13) downstream of the TAA stop codon for ADAMTS4).

The EcoRI-NotI fragment (SEQ ID NO:14) containing the intact ADAMTS4 coding sequence was subcloned into pHTop. This plasmid was derived from pED (Kaufman et al., Nucleic Acids Res. 19:4485–4490, 1991) by removing the majority of the adenovirus major late promoter and inserting six repeats of the tet operator (Gossen et al., Proc. Natl. Acad. Sci. USA 89:5547–5551, 1992). A CHO cell line stably expressing ADAMTS4 was obtained by transfecting pHTop/ADAMTS4 into CHO/A2 cells and selecting clones in 0.05 µM methotrexate. The CHO/A2 cell line was derived from CHO DUKX B11 cells (Urlaub et al., Proc. Natl. Acad. Sci. USA 77:4216–4220, 1980) by stably integrating a transcriptional activator, a fusion between the tet repressor and the herpesvirus VP 16 transcription activation domain (Gossen et al., Proc. Natl. Acad. Sci. USA 89:5547–5551, 1992).

The CHO cell-conditioned medium was harvested and diluted 3-fold with buffer A (20 mM Tris (pH 7.2), 5 mM CaCl$_2$, and 10 µM ZnCl$_2$) and applied to a 50µ Poros HQ column (PE Biosystems, Foster City, Calif.). The column was washed with buffer B (20 mM Tris (pH 7.2), 50 mM NaCl, 5 mM CaCl$_2$, and 10 µM ZnCl$_2$), and the protein was eluted with a linear gradient of buffer B containing 50 mM to 1.0M NaCl. The ADAMTS4-containing fraction was further purified by application to a 50µ Poros HS column after a 10-fold dilution with buffer C (20 mM Tris (pH 6.8), 50 mM NaCl, 5 mM CaCl$_2$, and 10 µM ZnCl$_2$), and the column was washed with 10 column volumes. Protein was eluted from the column with a linear gradient of buffer C containing 50 mM to 1.0M NaCl, and the calculated extinction coefficient at 280 nm was used for protein concentration determination as outlined by Gill and von Hippel (Gill and von Hippel, Anal. Biochem. 182:319–326, 1989).

Example 2

Generation of Truncated ADAMTS4 Molecules by Auto-digestion

Purified recombinant human ADAMTS4 migrated on SDS-PAGE gels predominantly as a 68 kD band, together with a small amount (<5% of total protein) of 53 kD material. Autocatalytic digestions were performed at 37° C. by incubating purified ADAMTS4 at concentrations ranging from 10 pg/ml to 569 pg/ml in 50 mM Tris-acetate, pH 7.3 containing 5 mM $CaCl_2$ and 0.1–1.0M NaCl. Auto-digested products were visualized by Coomassie blue staining, by silver staining, or by Western immunoblot analysis with the L9026 antibody.

Following incubation at 37° C. for various times up to 16 h, ADAMTS4 was detected as isoforms of 68 kD (ADAMTS4 (p68)), 53 kDa (ADAMTS4(p53)) and 40 kD (ADAMTS4(p40)). Results from incubations performed using ADAMTS4 at concentrations ranging from 10 pg/ml to 569 pg/ml, and at salt concentrations up to 1.0M, were essentially identical. Incubation of ADAMTS4 ASM under the same condition resulted in no detectable isoforms, thus confirming that the processing of ADAMTS4 was autocatalytic (Flannery et al., J. Biol. Chem. 277:42775–42780).

Example 3

Amino Acid Sequencing and Mass Spectrometry Analyses of Auto-digested ADAMTS4 Isoforms For N-terminal sequence analysis, aliquots of auto-digested ADAMTS4 isoforms were separated on 10% Bis-Tris NuPage SDS-PAGE gels and transferred to PVDF membranes which were stained with Coomassie blue. Excised bands corresponding to ADAMTS4(p68), ADAMTS4(p53) and ADAMTS4(p40) were subjected to automated sequencing on a PE-Biosystems 491A Pulsed-Liquid Sequencer on-line with a PE-Biosystems 140S PTH Analyzer (Procise-HT).

For C-terminal sequence analysis, auto-digested ADAMTS4 isoforms were separated by fractionation on a column of Poros HQ. Unbound ADAMTS4(p53) and ADAMTS4(p40) were subsequently fractionated on a column of Poros HS eluted using an isocratic gradient of 0.05–1.0 M NaCl in 25 mM HEPES, pH 6.8, 5 mM $CaCl_2$ and 5 pM $ZnCl_2$. Mass spectrometry analyses were performed using a Micromass LCT (LC-TOF-MS) analyzer (Micromass UK, Ltd, Manchester, U.K.). Samples were concentrated and desalted using ABI ProSorb cartridges. C-terminal sequence analyses were performed at the Mayo Protein Core Facility, Rochester, Minn., on an ABI Procise C instrument using thiohydantoin derivitization chemistry.

FIG. 1 shows a schematic representation of the structure of furin-processed full-length ADAMTS4 mature enzyme (ADAMTS4(p68)) and the auto-digested isoforms ADAMTS4(p53) and ADAMTS4(p40). The full-length ADAMTS4 mature enzyme contains 625 amino acids (phe213-lys837, SEQ ID NO:15, which is encoded by a nucleotide sequence (SEQ ID NO:16) corresponding to position 648-2522 of SEQ ID NO:14. The auto-digested isoform ADAMTS4(p53) contains 482 amino acids (phe213-lys694, SEQ ID NO:17, which is encoded by a nucleotide sequence (SEQ ID NO:18) corresponding to position 648-2093 of SEQ ID NO: 14). The auto-digested isoform ADAMTS4(p40) contains 369 amino acids (phe213-thr581, SEQ ID NO:19, which is encoded by a nucleotide sequence (SEQ ID NO:20) corresponding to position 648-1754 of SEQ ID NO:14).

The sequence for ADAMTS4(p68) contains no consensus attachment sites for Winked oligosaccharides, and it is apparent that the recombinant ADAMT4 used in this study was indeed non-glycoslyated. Consequently, the measured mass of 52,356 dalton for ADAMTS4(p53) (determined by LC-TOF-MS) was consistent with the detected C-terminal sequence of -Phe-Arg-Lys694-OH, indicating an auto-catalytic cleavage of the Lys694-Phe695 peptide bond. Similarly, the C-terminal sequence -Ser-Ala-Leu-Thr581-OH detected for ADAMTS-4(p40) indicates auto-catalytic cleavage at Thr581-Phe582, and the calculated mass for Phe213-Thr581 (39,757 dalton) is in good agreement with the mass of 40,040 dalton measured by LC-TOF-MS.

Example 4

Affinity of Auto-catalytically Generated ADAMTS4 Isoforms for Sulfated GAGs

Purified ADAMTS4 and auto-catalytic ADAMTS4 isoforms were separated by SDS-PAGE under non-reducing conditions and transferred to nitrocellulose membranes. Affinity blotting with biotinylated heparin (bHep), a commercially available (labeled) sulfated GAG, was performed by incubating the membrane with bHep (Calbiochem, San Diego, Calif., 0.05 pg/ml) in 20 mM Tris, pH 7.4, containing 0.5M NaCl. For binding-competition experiments, membranes were pre-incubated for 1 h with unlabelled heparin (0.5–50 pg/ml). Additional competition experiments were performed using bovine articular cartilage D1 aggrecan prepared from 4M guanidine HC1 extracts fractionated by equilibrium density centrifugation in cesium chloride as previously described and treated with or without chondroitinase ABC, keratanase and keratanase II as previously described. ADAMTS4 auto-catalytic isoforms were also separated using a heparinsepharose affinity column (Amersham Pharmacia Biotech) eluted with a step-wise gradient of 0.1–1.0M NaCl in 10 mM sodium phosphate, pH 7.0.

The affinity blotting experiments revealed that whereas ADAMTS4(p68) bound biotinylated heparin in the presence of 0.5M NaCl, no such binding was observed for ADAMTS4(p53) or ADAMTS4(p40). Likewise, the ADAMTS4 ASM C-terminal deletion mutant (Met1-phe575), lacking the "spacer" domain, did not bind bHep under these conditions (Flannery et al., J. Biol. Chem. 277:42775–42780). The auto-catalytic ADAMTS4 isoforms also showed reduced binding to heparin-sepharose. Compared to ADAMTS4(p68), which was eluted from the heparin-sepharose column in the presence of 0.8M NaCl, ADAMTS4(p53) and ADAMTS4(p40) were eluted at 0.3M NaCl and 0.4M NaCl, respectively. In binding-competition experiments, pre-incubation of affinity blots with unlabelled heparin blocked binding of bHep to ADAMTS4(p68) in a dose-dependent manner. In addition, bovine aggrecan also blocked binding of bHep to ADAMTS4(p68), and this binding-competition was dependent on the presence of aggrecan GAGs (Flannery et al., J. Biol. Chem. 277:42775–42780). Since both of the truncated isoforms retain the TSP-1 motif (see FIG. 1), it is evident that additional sites located within the ADAMTS4 "spacer" domain contribute to GAG binding and interaction with glycosylated aggrecan (Flannery et al., J. Biol. Chem. 277: 42775–42780).

Example 5

Aggrecanase Activity of Auto-catalytially Generated ADAMTS4 Isoforms

The aggrecanase activity of the auto-catalytically generated ADAMTS4 isoforms, ADAMTS4(p53) and ADAMTS4(p40), were determined using methods described in Example 7. Briefly, bovine aggrecan was incubated with purified ADAMTS4(p53) and ADAMTS4(p40) for 16 h at 37° C. Digestion products were deglycoslyated with chondroitinase ABC and keratanases, separated by SDS-PAGE, and visualized by Western blot using monoclonal antibody BC-3, which specifically detects the neoepitope sequences $_{374}$ARGXX (SEQ ID NO:21) generated by aggrecanase cleavage of the glu373-ala374 peptide bond within the aggrecan interglobular domain. The result showed that both isoforms have aggrecanase activity (Flannery et al., J. Biol. Chem. 277:42775–42780).

Example 6

Generation and Purification of Modified Human ADAMTS4 Molecules

Figure 2:
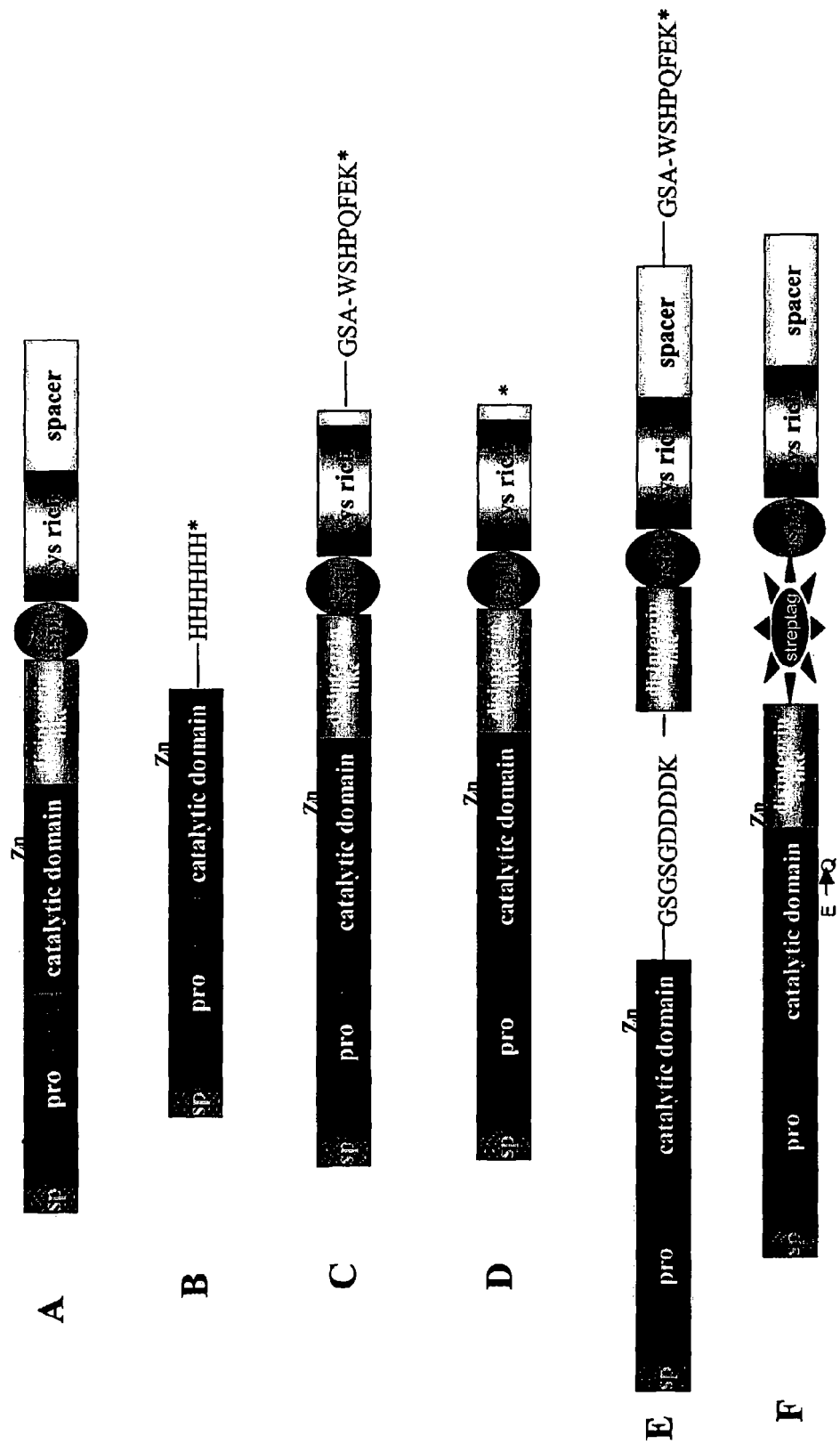
FIG. 2 is a schematic showing various embodiments of modified mTS4 molecules (constructs B-I).

FIG. 2 shows schematics of the native, unprocessed ADAMTS4 molecule (construct A) and various modified human ADAMTS4 molecules (constructs B-I). As shown in construct A, the unprocessed pro-protein of ADAMTS4 (SEQ ID NO:1) contains a signal peptide (sp), a pro-peptide (pro), a catalytic domain, a disintegrin-like domain, a TSP-1 domain, a cysteine-rich domain, and a spacer domain.

Constructs B–D are truncated ADAMTS4 constructs generated using standard molecular biology techniques. Construct B (SEQ ID NO.22) is a truncated ADAMTS4 molecule lacking the disintegrin-like domain, the TSP-1 motif, the cystein rich domain and the spacer, but containing a His tag (HHHHHH, SEQ ID NO:23). The furin-processed protein from this construct is enzymatically inactive (SEQ ID NO:46). Construct C (SEQ ID NO:24) contains a tag sequence (GSAWSHPQFEK, SEQ ID NO:25) and a C-terminal deletion that removed most of the spacer region. Construct D (SEQ ID NO:26) is an untagged version of construct C. Both constructs C and D can be expressed in CHO cells. The furin-processed mature proteins of construct C and D (SEQ ID NOS:47 and 48, respectively) have aggrecanase activity.

Construct E (SEQ ID NO:27) was made by inserting, in frame, coding sequence for the amino acids -GSGSGD-DDDK- (SEQ ID NO:28) between the catalytic domain and the disintegrin-like domain of ADAMTS4, along with a Strep-tag on the C-terminus. The -GSGSG- constitutes a flexible amino acid spacer and the -DDDDK- constitutes a recognition site for the highly specific protease enterokinase. This construct was prepared after results obtained with construct B in FIG. 2 showed that removal of coding sequence for the C-terminal domains following the catalytic domain resulted in a protein that was inactive. Protein derived from construct B was appropriately processed (furin cleavage of the pro-domain), but the pro-peptide remained associated with the catalytic domain. It is possible that the presence of the C-terminal disintegrin-like, TSP-1, cys-rich, and spacer domains might facilitate folding of the catalytic domain and/or displacement of the cleaved pro-peptide to generate active enzyme. The intent of construct E was to allow the full-length ADAMTS4 protein to be translated and fold, to be purified by virtue of the C-terminal tag (GSAW-SHPQFEK, SEQ ID NO:25), and then cleaved with exogenously added enterokinase to produce intact catalytic domain, amenable to activity assays and structural determinations.

Constructs F–I are modified ADAMTS4 molecules carrying an active-site mutation (ASM). The full-length ASM construct G (SEQ ID NO:29) was created by introducing a single basepair change (G to C at position 1084) into the wild-type ADAMTS4 using the Quick Change Site Directed Mutagenesis Kit (Stratagene, La Jolla, Calif.). The nucleotide change resulted in a single amino acid change from glu to gln at position 362 ($E_{362}Q$). Construct G, which also contains a FLAG tag (VDYKDDDDK, SEQ ID NO:30) was expressed in CHO cells and purified as described in Example 1. The $E_{362}Q$ mutation abolished the aggrecanase activity of the mature protein (SEQ ID NO:50) of construct G. The mature protein, however, is more stable than the native ADAMTS4 protein.

Truncated ASM constructs H (SEQ ID NO:31) and I (SEQ ID NO:32) were generated by PCR amplification of part of construct G using PCR primers with incorporated restriction sites. Construct H lacks the spacer domain and contains a C-terminal FLAG epitope tag. Construct I lacks the spacer and the TSP-1 domain and contains a C-terminal FLAG epitope tag. For construct H, the 5'-primer was: Ag1B1F: 5' TAAATCGAATTCCCACCATGTCCCAGA-CAGGCTCGCATCCCG 3' (SEQ ID NO:33). The 3'-primer was Ag1B2R: 5' TATTATGTCTACTGGGCAGTCCT-CAGTGTTGCAGGAG 3' (SEQ ID NO:34). For construct I, the 5'-primer was: Ag1B1F: 5' TAAATCGAATTCCCAC-CATGTCCCAGACAGGCTCGCATCCCG 3' (SEQ ID NO:33). The 3'-primer was Ag1B1R: 5' TATTATGTCTA-CAGCCTGTGGAATATTGAAGTCCTGG 3' (SEQ ID NO:35).

The PCR amplification was performed using standard conditions described by BD Biosciences BD Advantage™-GC 2 Polymerase Mix. The amplified products, which contained the unique restriction sites EcoRI at 5' end and AccI at 3' end, were subcloned in two steps to end up in pHTop with a C-terminal FLAG tag. Briefly, the PCR products were digested using standard conditions with the restriction enzymes EcoR1 and AccI. The digested products were fractionated on an agarose gel and bands corresponding to the predicted size were excised from the gel. DNA was recovered from the gel utilizing a Prep-A-Gene kit from BioRad according to the manufacture directions. The recovered DNA was directionally cloned (EcoRI-AccI) into the intermediate vector pTAdv-FLAG, which was constructed by annealing the two synthetic oligonucleotides Flag1 5' AATTCCTATGCTAGTGCTATCGTAGAC-TACAAGGATGACGATGACAAGTAAGC 3' (SEQ ID NO:36), and Flag2 5' GGCCGCTTACTTGTCATCGT-CATCCTTGTAGTCTACGATAGCACTAGCATAGG 3' (SEQ ID NO:37) together and cloning directionally (EcoRI-NotI) into Clontech pTAdv vector. The complete nucleotide sequence of the pTAdv-FLAG cloning vector is recited in SEQ ID NO:38.

Sequence confirmed recombinant plasmids were then amplified using standard techniques and digested with the restriction enzymes EcoRI and NotI. The EcoRI-NotI fragments were then gel purified as described above and cloned directionally into the pHTop vector (SEQ ID NO:39).

The two constructs were expressed in CHO/A2 cells, and purified from conditioned media using anti-FLAG agarose affinity gel (Sigma-Aldrich, St. Louis, Mo.). Polyclonal rabbit anti-human ADAMTS4 antisera L9026, generated using an immunizing mixture of eight distinct synthetic peptides derived from all domains of the enzyme, was purified on a HiTrap Protein G HP affinity column (Amersham Pharmacia Biotech, Piscataway, N.J.). Following protein separation on 10% SDS-PAGE gels (Invitrogen, Carlsbad, Calif.), the antibody was used at a concentration of 1.5 pg/ml for Western immunoblotting and detection on Hybond nitrocellulose membranes with ECL reagents (Amersham Pharmacia Biotech). Furin-processed construct H (SEQ ID NO:51) and construct I (SEQ ID NO:52) lack aggrecanase activity but are more stable than the wild-type ADAMTS4 protein.

A full-length ADAMTS4 ASM construct with an insertion was also created (construct F, SEQ ID NO:40). The construct contains a strep tag (WSHPQFEK, SEQ ID NO:41) inserted between the disintegrin-like domain and the TSP-1 motif. Construct F was designed in an attempt to solve the problems that we encountered with poor yield of purified full-length ADAMTS4. C-terminal tagging of ADAMTS4 proved to be sub-optimal due to loss of the tag by autocatalytic C-terminal processing. In construct F, the Strep tag was moved internally, between the disintegrin-like and Tsp domains. In this position, any auto-catalysis within the cys-rich and spacer domains would not release the Strep tag.

Example 7

Biological Activity of Expressed Aggrecanase

The biological activity of the expressed aggrecanase proteins, such as the modified aggrecanases of the present invention, may be assayed in accordance with the following assays:

Fluorescent peptide assay: Expressed protein is incubated with a synthetic peptide which encompasses amino acids at the aggrecanase cleavage site of aggrecan. Either the N-terminus or the C-terminus of the synthetic peptide is labeled with a flourophore and the other terminus includes a quencher. Cleavage of the peptide separates the flourophore and quencher and elicits flourescence. From this assay it is determined that the expressed aggrecanase protein can cleave aggrecan at the aggrecanase site, and relative fluorescence is a determination the relative activity of the expressed protein.

Neoepitope western blot: Expressed aggrecanase protein is incubated with intact aggrecan. After several biochemical manipulations of the resulting sample (dialysis, chondroitinase treatment, lyophilization and reconstitution) the sample is run on an SDS-PAGE gel. The gel is incubated with an antibody that is specific to a site on aggrecan which is only exposed after aggrecanase cleavage. The gel is transferred onto nitrocellulose paper and developed using a secondary antibody (called a western assay) which subsequently results in a banding pattern indicative of products with a molecular weight consistent with aggrecanase generated cleavage products of aggrecan. This assay results in the finding that the expressed aggrecanase protein cleaved native aggrecan at the aggrecanase cleavage site, and also gives the molecular weight of the cleavage products. Relative density of the bands can give an indication of relative aggrecanase activity.

In one embodiment, bovine articular cartilage aggrecan was incubated with purified ADAMTS4 or modified ADAMTS4 protein for 16 h at 37° C. in 50 mM Tris, pH 7.3, containing 100 mM NaCl and 5 mM $CaCl_2$. Digestion products were deglycosylated by incubation for 2 h at 37° C. in the presence of chondroitinase ABC (Seikagaku America, Falmouth, Mass.; 1 mU/µg aggrecan), keratanase (Seikagaku; 1 mU/µg aggrecan) and keratanase II (Seikagaku; 0.02 mU/µg aggrecan). Digestion products were separated on 4–12% Bis-Tris NuPAGE SDS PAGE gels (Invitrogen, Carlsbad, Calif.) and then electrophoretically transferred to nitrocellulose. Immunoreactive products were detected by Western blotting with monoclonal antibody (MAb) AGG-C1 (0.04 µg/ml) or MAb BC-3 (generously provided by Dr. C. Hughes and Prof. B. Caterson, Cardiff University, UK; 1:100 of hybridoma culture supernatant). Alkaline-phosphatase-conjugated secondary goat anti-mouse IgG (Promega Corp., Madison, Wis.; 1:7500) was subsequently incubated with the membranes, and NBT/BCIP substrate (Promega) was used to visualize immunoreactive bands. All antibody incubations were performed for 1 h at room temperature, and the immunoblots were incubated with the substrate for 5–15 min at room temperature to achieve optimum color development.

Aggrecan ELISA: Expressed protein is incubated with intact aggrecan which had been previously adhered to plastic wells. The wells are washed and then incubated with an antibody that detects aggrecan. The wells are developed with a secondary antibody. If the original amount of aggrecan remains in the wells, the antibody staining is dense. If aggrecan was digested by aggrecanase activity of the expressed aggrecanase protein, the aggrecan comes off the plate and the subsequent staining of the aggrecan-coated wells by the antibody is reduced. This assay tells whether an expressed protein is capable of cleaving aggrecan (anywhere in the protein, not only at the aggrecanase site) and can further determine relative aggrecan cleavage.

Briefly, microtiter plates (Costar) were coated with hyaluronic acid (ICN), followed by chondroitinase (Seikagaku Chemicals)-treated bovine aggrecan. Conditioned medium from CHO cells expressing modified aggrecanase was added to the aggrecan-coated plates. Aggrecan cleaved at the glu373-ala374 within the interglobular domain was washed away. The remaining uncleaved aggrecan was detected with the 3B3 monoclonal antibody (ICN), followed by anti-mouse IgM-HRP secondary antibody (Southern Biotechnology). Final color development was with 3,3", 5,5" tetramethylbenzidine (TMB, BioFx Laboratories). Alternatively, modified aggrecanase can be synthesized in the inactive pro-form and can be processed by furin to yield the mature species.

Example 8

Construction of Expression Vectors for Modified Aggrecanase

One skilled in the art can construct expression vectors for modified aggrecanase by inserting sequences encoding modified aggrecanase into known mammalian expression vectors, such as pCD (Okayama et al., Mol. Cell Biol. 2:161–170, 1982), pJL3, pJL4 (Gough et al., EMBO J. 4:645–653, 1985) and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a Xho1 site for insertion of cDNA clones. The functional elements of pMT2 CXM have been described (Kaufman, et al., Proc. Natl. Acad. Sci. USA 82:689693, 1985) and include the adenovirus VA genes, the SV40 origin of replication including the 72 by enhancer, the adenovirus major late promoter including a 5' splice site and the majority of the adenovirus tripartite leader sequence present on adenovirus late mRNAs, a 3' splice acceptor site, a dihydrofolate reductase (DHFR) insert, the SV40 early polyadenylation site (SV40), and pBR322 sequences needed for propagation in E. coli.

Plasmid pMT2 CXM is obtained by EcoR1 digestion of pMT2-VWF, which has been deposited with the American Type Culture Collection (ATCC, Rockville, Md., USA) under accession number ATCC 67122. EcoR1 digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis (Morinaga, et al., Biotechnology 84: 636, 1984). This removes bases 1075 to 1145 relative to the Hind III site near the SV40 origin of replication and enhancer sequences of pMT2. In addition it inserts the following sequence: 5'-CATGGGCAGCTCGAG-3' (SEQ ID NO:42) at nucleotide 1145. This sequence contains the recognition site for the restriction endonuclease Xho I. A derivative of pMT2CXM, termed pMT23, contains recognition sites for the restriction endonucleases Pst1, EcoR1, Sa11 and Xho1. Plasmid pMT2 CXM and pMT23 DNA may be prepared by conventional methods.

pEMC281 derived from pMT21 may also be suitable in practice of the invention. pMT21 is derived from pMT2 which is derived from pMT2-VWF. As described above EcoR1 digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a Xho1 site is inserted to obtain the following sequence immediately upstream from DHFR:

instance, a cDNA encoding an aggrecanase can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of aggrecanase or aggrecanase-like proteins. Additionally, the aggrecanase sequences can be manipulated to express an aggrecanase or aggrecanase-like protein by deleting aggrecanase encoding pro-peptide sequences and replacing them with sequences encoding the complete pro-peptides of other aggrecanase proteins. It is also possible to replace a protein domain in a modified aggrecanase (e.g., a modified ADAMTS4) with the corresponding domain from a different aggrecanase (e.g., a modified ADAMTS5).

One skilled in the art can also manipulate the sequences of expression vectors by eliminating or replacing the mammalian regulatory sequences flanking the coding sequence with bacterial sequences to create bacterial vectors for intracellular or extracellular expression of modified aggrecanase molecules. For example, the coding sequences could be further manipulated (e.g. ligated to other known linkers or modified by deleting non-coding sequences therefrom or altering nucleotides therein by other known techniques). A

```
5' CTGCAGGCGAGCCTGAATTCCTCGAGCCATCATG 3'    (SEQ ID NO:43)
       Pst1          EcoR1 Xho1
```

Second, a unique C1a1 site is introduced by digestion with EcoRV and Xba1, treatment with Klenow fragment of DNA polymerise I, and ligation to a ClaI linker (CATCGATG, SEQ ID NO:44). This deletes a 250 by segment from the adenovirus associated RNA (VAI) region but does not interfere with VAI RNA gene expression or function. pMT21 is digested with EcoR1 and Xho1, and used to derive the vector pEMC2B 1.

A portion of the EMCV leader is obtained from pMT2-ECATI (S. K. Jung, et al, J. Virol. 63:1651–1660, 1989) by digestion with EcoR1 and Pst1, resulting in a 2752 by fragment. This fragment is digested with Taq1 yielding an EcoRI-Taq1 fragment of 508 by which is purified by electrophoresis on low melting agarose gel. A 68 by adapter and its complementary strand are synthesized with a 5' Taq1 protruding end and a 3' Xho1 protruding end which has the following sequence:

modified aggrecanase encoding sequence could then be inserted into a known bacterial vector using procedures such as described by Taniguchi et al., (Taniguchi et al., Proc. Natl Acad. Sci. USA, 77:5230–5233, 1980). This exemplary bacterial vector could then be transformed into bacterial host cells to express an aggrecanase protein of the invention. For a strategy for producing extracellular expression of aggrecanase-related proteins in bacterial cells, see, e.g. European patent application EP 177,343.

Similar manipulations can be performed for construction of an insect vector (see, e.g., procedures described in published European patent application EP 155,476) for expression in insect cells. A yeast vector could also be constructed employing yeast regulatory sequences for intracellular or extracellular expression of the factors of the present invention by yeast cells. (See, e.g., procedures described in

```
5' CGAGGTTAAAAAACGTCTAGGCCCCCCGAACCACGGGGACGTGGTTTTCCTTTGAAAAACACGATTGC 3'   (SEQ ID NO:46)
   Taq1                                                                Xho1
```

This sequence matches the EMC virus leader sequence from nucleotides 763 to 827. It also changes the ATG at position 10 within the EMC virus leader to an ATT and is followed by a Xho1 site. A three way ligation of the pMT21 EcoRI-16 hol fragment, the EMC virus EcoR1-Tag1 fragment, and the 68 by oligonucleotide adapter Tag1-16 hol adapter results in the vector pEMC2/61.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and Q-lactamase markers and an EMC sequence, in appropriate relationships to direct the high level expression of the desired cDNA in mammalian cells.

The construction of expression vectors may involve modification of the aggrecanase-related DNA sequences. For published PCT application WO86/00639 and European patent application EP 123,289).

A method for producing high levels of an aggrecanase-related protein of the invention in mammalian, bacterial, yeast or insect host cell systems may involve the construction of cells containing multiple copies of the heterologous aggrecanase-related gene. The heterologous gene is linked to an amplifiable marker e.g., the dihydrofolate reductase (DHFR) gene for which cells containing increased gene copies can be selected for propagation in increasing concentrations of methotrexate (MTX) (Kaufinan and Sharp, J. Mol. Biol., 159:601–629, 1982). This approach can be employed with a number of different cell types.

For example, an expression plasmid containing coding sequence of a modified aggrecanase and the DHFR expression plasmid pAdA26SV(A)3 (Kaufman and Sharp, Mol. Cell. Biol., 2:1304, 1982) can be co-introduced into DHFR-deficient CHO cells, DUKX-1311, by various methods including calcium phosphate co-precipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 pM MTX) (Kaufinan et al. Mol. Cell Biol., 5:1750, 1983). Transformants are cloned, and biologically active modified aggrecanase expression is monitored by at least one of the assays described above. Aggrecanase protein expression should increase with increasing levels of MTX resistance. Modified aggrecanase polypeptides are characterized using standard techniques known in the art such as pulse labeling with 35S methionine or cysteine and polyacrylamide gel electrophoresis. Similar procedures can be followed to produce other modified aggrecanases or aggrecanase-like proteins.

Example 9

Preparation of Antibodies

An antibody against a modified aggrecanase of the present invention is prepared. To develop an antibody capable of inhibiting aggrecanase activity, a group of mice are immunized every two weeks with a modified aggrecanase protein mixed in Freunds complete adjuvant for the first two immunizations, and incomplete Freunds adjuvant thereafter. Throughout the immunization period, blood is sampled and tested for the presence of circulating antibodies. At week 9, an animal with circulating antibodies is selected, immunized for three consecutive days, and sacrificed. The spleen is removed and homogenized into cells. The spleen cells are fused to a myeloma fusion partner (line P3-x63-Ag8.653) using 50% PEG 1500 by an established procedure (Oi and Herzenberg, Selected Methods in Cellular Immunology, W. J. Freeman Co., San Francisco, Calif., 351, 1980). The fused cells are plated into 96-well microtiter plates at a density of $2 \times 10^5$ cells/well. After 24 hours, the cells are subjected to HAT selection (Littlefleld et al., Science, 145:709, 1964) effectively killing any unfused and unproductively fused myeloma cells.

Successfully fused hybridoma cells secreting anti-aggrecanase antibodies are identified by solid and solution phase ELISAs. The modified aggrecanase protein is prepared from CHO cells as described above and coated on polystyrene (for solid phase assays) or biotinylated (for a solution based assay). Neutralizing assays are also employed where aggrecan is coated on a polystyrene plate and aggrecanase activity is inhibited by the addition of hybridoma supernatant. Hybridomas expressing aggrecanase antibodies are cultured and expanded for further study. Selected hybridomas are cloned by limiting dilution and cryopreserved. Isotypes of the antibodies produced by the hybridomas are determined using a mouse immunoglobulin isotyping kit (ZymedTm Laboratories, Inc., San Francisco, Calif.).

Example 10

Method of Treating a Patient with an Anti-aggrecanase Antibody

The antibody developed according to Example 10 can be administered to patients suffering from a disease or disorder related to the loss of aggrecan, or excess aggrecanase activity. Patients take the composition one time or at intervals, such as once daily, and the symptoms and signs of their disease or disorder improve. For example, loss of aggrecan would decrease or cease and degradation of articular cartilage would decrease or cease. Symptoms of osteoarthritis would be reduced or eliminated. This shows that the composition of the invention is useful for the treatment of diseases or disorders related to the loss of aggrecan, or excess aggrecanase activity. The antibodies can also be used with patients susceptible to osteoarthritis, such as those who have a family history or markers of the disease, but have not yet begun to suffer its effects. A tentative experimental design is shown in Table 2.

TABLE 2

Treating osteoarthritis with anti-aggrecanase antibody

| Patient's Condition | Route of Administration | Dosage | Frequency | Predicted Results |
|---|---|---|---|---|
| Osteoarthritis | Subcutaneous | 500 µg/kg | Daily | Decrease in symptoms |
| " | " | 1 mg/kg | Weekly | " |
| " | Intramuscular | 500 µg/kg | Daily | " |
| " | " | 1 mg/kg | Weekly | " |
| " | Intravenous | 500 µg/kg | Daily | " |
| " | " | 1 mg/kg | Weekly | " |
| Family History of Osteoarthritis | Subcutaneous | 500 µg/kg | Daily | Prevention of condition |
| Family History of Osteoarthritis | Intramuscular | 500 µg/kg | Daily | " |
| Family History of Osteoarthritis | Intravenous | 500 µg/kg | Daily | " |

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto. All of the documents cited in this application are incorporated by reference in their entirety. Additionally, all sequences cited in databases and all references disclosed are incorporated by reference in their entirety.

We claim:

1. An isolated, modified, human ADAMTS4 protein comprising
   (a) an ADAMTS4 catalytic domain wherein the glutamate at the position corresponding to position 362 of SEQ ID NO:1 is substituted with a glutamine, and
   (b) a disintegrin domain.

2. An isolated, modified, human ADAMTS4 protein of claim 1, wherein said protein comprises a peptide tag.

3. The isolated, modified, human ADAMTS4 protein of claim 1, further comprising a deletion of all or a portion of an ADAMTS4 spacer domain.

4. The isolated, modified, human ADAMTS4 protein of claim 1, said modified ADAMTS4 protein comprising the amino acid sequence of SEQ ID NO: 29.

5. The isolated, modified, human ADAMTS4 protein of claim 1, said modified ADAMTS4 protein comprising the amino acid sequence of SEQ ID NO: 31.

6. The isolated, modified, human ADAMTS4 protein of claim 1, said modified ADAMTS4 protein comprising the amino acid sequence of SEQ ID NO: 32.

7. The isolated, modified, human ADAMTS4 protein of claim 1, said modified ADAMTS4 protein comprising the amino acid sequence of SEQ ID NO:40.

8. The isolated, modified, human ADAMTS4 protein of claim 1, said modified ADAMTS4 protein comprising the amino acid sequence of SEQ ID NO:50.

9. The isolated, modified, human ADAMTS4 protein of claim 1, said modified ADAMTS4 protein comprising the amino acid sequence of SEQ ID NO:51.

10. The isolated, modified, human ADAMTS4 protein of claim 1, said modified ADAMTS4 protein comprising the amino acid sequence of SEQ ID NO:52.

11. The isolated, modified, human ADAMTS4 protein of claim 1, said modified ADAMTS4 protein comprising the amino acid sequence of SEQ ID NO: 53.

12. The isolated, modified, human ADAMTS4 protein of claim 1, said modified ADAMTS4 protein further comprising a TSP-1 domain.

13. The isolated, modified, human ADAMTS4 protein of claim 1, said modified ADAMTS4 protein further comprising a cysteine-rich domain.

14. The isolated, modified, human ADAMTS4 protein of claim 1, said modified ADAMTS4 protein further comprising an amino acid substitution at a glycosylation recognition site.

* * * * *

UNITED STATES PATENT AND TRADEMARK OFFICE
CERTIFICATE OF CORRECTION

PATENT NO. : 7,118,902 B2
APPLICATION NO. : 10/628432
DATED : October 10, 2006
INVENTOR(S) : Corcoran et al.

It is certified that error appears in the above-identified patent and that said Letters Patent is hereby corrected as shown below:

Col. 123, Line 32
Claim 2, line 1, delete "An" and replace with --The--.

Signed and Sealed this

Twenty-seventh Day of March, 2007

JON W. DUDAS
*Director of the United States Patent and Trademark Office*